United States Patent
Yang et al.

(10) Patent No.: US 10,106,647 B2
(45) Date of Patent: *Oct. 23, 2018

(54) BIOELASTOMERS AND APPLICATIONS THEREOF

(71) Applicant: The Penn State Research Foundation, University Park, PA (US)

(72) Inventors: Jian Yang, State College, PA (US); Jinshan Guo, State College, PA (US)

(73) Assignee: The Penn State Research Foundation, University Park, PA (US)

(*) Notice: Subject to any disclaimer, the term of this patent is extended or adjusted under 35 U.S.C. 154(b) by 169 days.

This patent is subject to a terminal disclaimer.

(21) Appl. No.: 14/916,140

(22) PCT Filed: Sep. 4, 2014

(86) PCT No.: PCT/US2014/054049
§ 371 (c)(1),
(2) Date: Mar. 2, 2016

(87) PCT Pub. No.: WO2015/035020
PCT Pub. Date: Mar. 12, 2015

(65) Prior Publication Data
US 2016/0199541 A1  Jul. 14, 2016

Related U.S. Application Data

(60) Provisional application No. 61/935,968, filed on Feb. 5, 2014, provisional application No. 61/874,287, filed on Sep. 5, 2013.

(51) Int. Cl.
*C08G 63/52* (2006.01)
*C08G 63/12* (2006.01)
(Continued)

(52) U.S. Cl.
CPC ............ *C08G 63/52* (2013.01); *A61L 27/34* (2013.01); *A61L 27/46* (2013.01); *A61L 27/56* (2013.01);
(Continued)

(58) Field of Classification Search
CPC ........ C08G 63/52; C08G 63/12; C08G 18/68; C08G 18/4615; C08G 18/73;
(Continued)

(56) References Cited

U.S. PATENT DOCUMENTS 8,927,682 B2   1/2015  Baker et al.

FOREIGN PATENT DOCUMENTS

EP        2014308 A2     1/2009
WO    WO2006012569   *  2/2006  ............... B05D 3/10
(Continued)

OTHER PUBLICATIONS

Diaz et al, Strength Enhancement of Nanostructured Organogels through Inclusion of Phthalocyanine-Containing Complementary Organogelator Structures and In Situ Cross-Linking by Click Chemistry, 2008, Chem. Eur. J., 14, 9261-9273. (Year: 2008).*
(Continued)

*Primary Examiner* — Trevor Love
(74) *Attorney, Agent, or Firm* — McCarter & English, LLP

(57) ABSTRACT

In one aspect, compositions are described herein. In some embodiments, a composition described herein comprises the reaction product of (i) citric acid, a citrate, or an ester of citric acid with (ii) a polyol, and (iii) a monomer comprising one or more alkyne moieties and/or azide moieties. The reaction product, in some instances, comprises a polymer. Further, in some cases, a composition described herein comprises a plurality of polymers. In some embodiments, the polymers are selected to be reactive with one another
(Continued)

through a click chemistry reaction scheme to form a polymer network. In another aspect, medical implants and medical devices are described herein, the implants and devices comprising a polymer or polymer network described herein.

32 Claims, 32 Drawing Sheets

(51) Int. Cl.
    *A61L 27/34*    (2006.01)
    *C08G 18/68*    (2006.01)
    *C08G 18/73*    (2006.01)
    *C08G 18/46*    (2006.01)
    *A61L 27/46*    (2006.01)
    *C08G 63/685*   (2006.01)
    *A61L 27/56*    (2006.01)

(52) U.S. Cl.
    CPC ......... *C08G 18/4615* (2013.01); *C08G 18/68* (2013.01); *C08G 18/73* (2013.01); *C08G 63/12* (2013.01); *C08G 63/6852* (2013.01); *C08G 63/6858* (2013.01); *A61L 2420/04* (2013.01); *A61L 2430/02* (2013.01)

(58) Field of Classification Search
    CPC . C08G 63/6858; C08G 53/6852; A61L 27/34; A61L 27/46; A61L 24/56; A61L 2430/02; A61L 2420/04
    See application file for complete search history.

(56) References Cited

FOREIGN PATENT DOCUMENTS

| WO | WO 2009/061854 A2 | 5/2009 | | |
|----|----|----|----|----|
| WO | WO 2009/136853 A1 | 11/2009 | | |
| WO | WO 2012/116250 A1 | 8/2012 | | |
| WO | WO2012116250 | * | 8/2012 | ........... C07D 319/12 |

OTHER PUBLICATIONS

Goldberg et al, Kinetics of modularly functionalized anatase nanoparticle attachment to humic acids, 2012, 243rd ACS National Meeting & Exposition Mar. 25-29, 2012, San Diego, California, 1 page (Abstract). (Year: 2012).*
Zhang et al, Preparation of Azido Polycarbonates and Their Functionalization via Click Chemistry, 2011, Macromolecules, 44, 1755-1759. (Year: 2011).*
Guo, Jinshan et al., Click Chemistry Plays a Dual Role in Biodegradable Polymer Design, Advanced Materials, vol. 26, No. 12, pp. 1906-1911, (2013).
PCT International Search Report and Written Opinion for PCT/US2014/054049 dated Nov. 26, 2014.
PCT/US2014/054049, Sep. 4, 2014, WO 2015/035020 A1.
U.S. Appl. No. 61/874,287, filed Sep. 5, 2013.
U.S. Appl. No. 61/935,968, filed Feb. 5, 2014.

* cited by examiner

Figure 7

| Samples | Density (g/cm³) | Tensile strength (MPa) | Young's modulus (MPa) | Elongation (%) | N (mol/m³) | Mc (g/mol) |
|---|---|---|---|---|---|---|
| POC | 1.24±0.01 | 6.66±0.84 | 5.39±0.51 | 207.81±24.03 | 718±128 | 1763±331 |
| POC-N₃-Al-1 (1/1) | 1.24±0.04 | 18.30±3.95 | 16.61±1.29 | 323.88±52.59 | 587±34 | 2111±151 |
| POC-N₃-Al-2 (1/1) | 1.24±0.01 | 28.33±1.22 | 43.89±5.54 | 289.87±26.67 | 7225±911 | 173±22 |
| POC-N₃-Al-3 (1/1) | 1.27±0.01 | 41.32±2.67 | 275.93±49.71 | 77.99±25.43 | 34307±1995 | 35±6 |
| CUPE | 1.20±0.01 | 27.68±2.63 | 13.70±1.09 | 443.70±80.11 | 1902±143 | 631±53 |
| CUPE-N₃-Al | 1.22±0.02 | 36.55±5.41 | 36.52±2.26 | 661.79±112.08 | 5003±351 | 244±19 |
| cBPLP-Ser | 1.22±0.01 | 11.33±1.33 | 7.99±0.44 | 274.22±44.16 | 1120±48 | 1093±42 |
| cBPLP-Ser-N₃-Al | 1.23±0.02 | 20.17±1.23 | 17.78±1.83 | 241.42±13.67 | 2536±192 | 486±36 |

BIOELASTOMERS AND APPLICATIONS THEREOF

CROSS REFERENCE TO RELATED APPLICATIONS

This application claims priority pursuant to 35 U.S.C. § 119 to U.S. Provisional Patent Application Ser. No. 61/874,287, filed on Sep. 5, 2013, and to U.S. Provisional Patent Application Ser. No. 61/935,968, filed on Feb. 5, 2014, each of which is hereby incorporated by reference in its entirety.

STATEMENT REGARDING FEDERALLY SPONSORED RESEARCH

This invention was made with government support under contract EB012575 awarded by the National Institute of Health and under Grant No. DMR 1313553, awarded by the National Science Foundation. The Government has certain rights in the invention.

FIELD

This invention relates to polymeric compositions and methods of making and using polymeric compositions and, in particular, to compositions comprising a citrate-containing polymer or oligomer and/or a clickable moiety.

BACKGROUND

In recent years, elastomeric polymers have found wide application in tissue engineering applications, in part due to the ability of some elastomeric polymers to mimic the elastic nature of many human soft tissues, such as heart valves, blood vessels, tendons, cartilage, and the bladder. However, many existing elastomeric polymers exhibit poor mechanical strength. In addition, the mechanical strength of some elastomeric polymers can be further reduced when the polymers are molded into porous scaffolds and/or used in vivo in a wet state, significantly limiting these materials' utility for some tissue engineering applications. Further, many previous polymers cannot effectively reduce or prevent microbial proliferation or bacterial infection in vivo. Separately formulated antibiotics or other antimicrobial materials must therefore often be coated onto, encapsulated within, or otherwise associated with such polymers. Moreover, some polymeric compositions treated in this manner can have limited antimicrobial effectiveness and/or exhibit degraded mechanical performance.

In addition, the repair of large segmental bone defects remains one of the most relevant challenges in reconstructive orthopedic surgery, but the management and treatment of such bone defects have presented various challenges in recent years. Bone is a relatively rigid and lightweight organ optimized to withstand external loads, and some previous bioengineered materials have been unable to match native bone composition and/or performance for various biomedical applications. For example, many previous materials are unable to provide adequate mechanical strength, minimize inflammatory responses, promote bone regeneration, and/or fully integrate with the surrounding tissue. In addition, some previous materials can include only a limited amount of bioceramic or other inorganic material without becoming too brittle for many load bearing applications.

Therefore, improved bioengineering polymer compositions and methods for treating conditions such as segmental bone defects are needed.

SUMMARY

In one aspect, compositions are described herein which, in some embodiments, may provide one or more advantages compared to some other compositions. For example, in some instances, a composition described herein can comprise a citrate-containing polymer or polymer network that can be used for various biomedical and/or bioengineering applications, including applications requiring the use of an elastomeric and/or high strength material. In some cases, a polymer or polymer network described herein can be used as a substitute for the native extracellular matrix (ECM) of a target tissue or organ. Further, in some such embodiments, the polymer or polymer network can provide the same or similar mechanical stability, structural integrity, and communication functions as native EMC or tissue. A polymer or polymer network described herein can also have a high cross-linking density. Additionally, in some cases, a composition described herein can comprise a tissue scaffold that is mechanically soft and elastic and that exhibits other mechanical properties that match the mechanical properties of a target tissue or organ. A composition described herein can also be biocompatible and/or amenable to surface modification by bioactive molecules such as cell-binding peptides, growth factors, or signaling molecules. In this manner, cell and tissue responses can be mediated by a composition described herein.

Moreover, in some embodiments, a composition described herein can be used to treat one or more diseases, injuries, or defects in a patient. For instance, in some cases, a composition described herein can be used to treat segmental bone defects. In some embodiments, a biphasic scaffold formed from a composition described herein can provide an osteoconductive surface for bone regeneration and tissue integration, while also mimicking the hierarchical organization of cancellous and cortical bone.

In some embodiments, a composition described herein comprises the reaction product of (i) citric acid, a citrate, or an ester of citric acid, such as triethyl citrate or another methyl or ethyl ester of citric acid, with (ii) a polyol such as a diol and (iii) a monomer comprising an alkyne moiety and/or an azide moiety. For example, in some cases, a composition described herein comprises a polymer formed from one or more monomers of Formula (A) hereinbelow; one or more monomers of Formula (B1), (B2), or (B3) hereinbelow; and one or more monomers comprising one or more alkyne moieties and/or one or more azide moieties. In some instances, the polymer is formed from monomers having a plurality of alkyne and/or azide moieties.

In addition, in some instances, a composition described herein comprises a plurality of polymers described herein, such as a first polymer formed from one or more monomers of Formula (A); one or more monomers of Formula (B1), (B2), or (B3); and one or more monomers comprising one or more alkyne moieties; and a second polymer formed from one or more monomers of Formula (A); one or more monomers of Formula (B1), (B2), or (B3); and one or more monomers comprising one or more azide moieties. Further, in some cases, a composition described herein comprises an azide-alkyne cycloaddition product, such as a 1,4-triazole ring or 1,5-triazole ring. Such a cycloaddition product can be formed from one or more polymers described herein. For example, in some cases, a first polymer and a second polymer of a composition described herein can form a polymer network by forming one or more azide-alkyne cycloaddition products from monomers comprising one or more alkyne moieties and one or more monomers comprising one or more azide moieties.

As described further hereinbelow, other click chemistry reaction products may also be present in a polymer or polymer network of a composition described herein.

Further, in some embodiments, a polymer or polymer network of a composition described herein is formed from one or more monomers in addition to those described hereinabove. For example, in some cases, a polymer is formed from one or more monomers comprising an isocyanate, an unsaturated polycarboxylic acid or polycarboxylic acid equivalent, an amino acid, a catechol-containing species, or a peptide, polypeptide, nucleic acid, or polysaccharide. Moreover, it is also possible to form a polymer described herein without using a monomer of Formula (A), (B1), (B2), or (B3). In some cases, for instance, a polymer is formed from one or more lactones and one or more monomers comprising an alkyne moiety or an azide moiety.

Additionally, in some instances, a composition described herein further comprises a particulate inorganic material dispersed within a network formed by a polymer described herein. In some cases, the particulate inorganic material comprises hydroxyapatite.

In another aspect, methods of making a polymer network are described herein. In some embodiments, a method of making a polymer network comprises mixing a first polymer and a second polymer, the first and second polymers each comprising a polymer of a composition described herein. For example, in some instances, the first polymer is formed from one or more monomers of Formula (A); one or more monomers of Formula (B1), (B2), or (B3); and one or more monomers comprising one or more alkyne moieties; and the second polymer is formed from one or more monomers of Formula (A); one or more monomers of Formula (B1), (B2), or (B3); and one or more monomers comprising one or more azide moieties. Such a method can further comprise reacting one or more alkyne moieties of the first polymer with one or more azide moieties of the second polymer to form one or more azide-alkyne cycloaddition products.

Moreover, in some embodiments, a method described herein further comprises functionalizing the surface of a polymer network described herein with one or more biofunctional species, such as one or more peptides, polypeptides, nucleic acids, and/or polysaccharides. In some instances, a peptide, polypeptide, nucleic acid, and/or polysaccharide is reacted with a pendant alkyne and/or azide moiety on the polymer network surface to provide a covalent bond between the polymer network and the peptide, polypeptide, nucleic acid, and/or polysaccharide.

In still another aspect, medical implants and medical devices are described herein. The medical implants and devices can comprise or be formed from a composition described herein. In some cases, such a medical implant or device comprises a tissue engineering scaffold forming a blood vessel, a cardiac tissue, a heart valve, a ligament, a tendon, a lung, a bladder, skin, a trachea, or a urethra.

Further, in some embodiments, a medical device or implant comprises a core-shell polymeric scaffold. Such a scaffold, in some cases, can comprise a core component having a first porosity; and a shell component surrounding the core component and having a second porosity, the second porosity differing from the first porosity. In some instances, the core component exhibits a higher porosity than the shell component. Further, the core component can comprise a first polymer network formed from one or more monomers of Formula (A); one or more monomers of Formula (B1), (B2), or (B3); one or more monomers comprising an alkyne moiety; and one or more monomers comprising an azide moiety. In addition, the shell component can comprise a second polymer network also formed from one or more monomers of Formula (A); one or more monomers of Formula (B1), (B2), or (B3); one or more monomers comprising an alkyne moiety; and one or more monomers comprising an azide moiety. In some embodiments, the core component and the shell component are concentric cylinders. Moreover, in some cases, a particulate inorganic material such as hydroxyapatite is dispersed within the first polymer network and/or the second polymer network of a scaffold described herein.

These and other embodiments are described in more detail in the detailed description which follows.

BRIEF DESCRIPTION OF THE FIGURES

FIG. 7 illustrates a table of physical, chemical, and mechanical properties of compositions according to some embodiments described herein.

DETAILED DESCRIPTION

Figure 1:
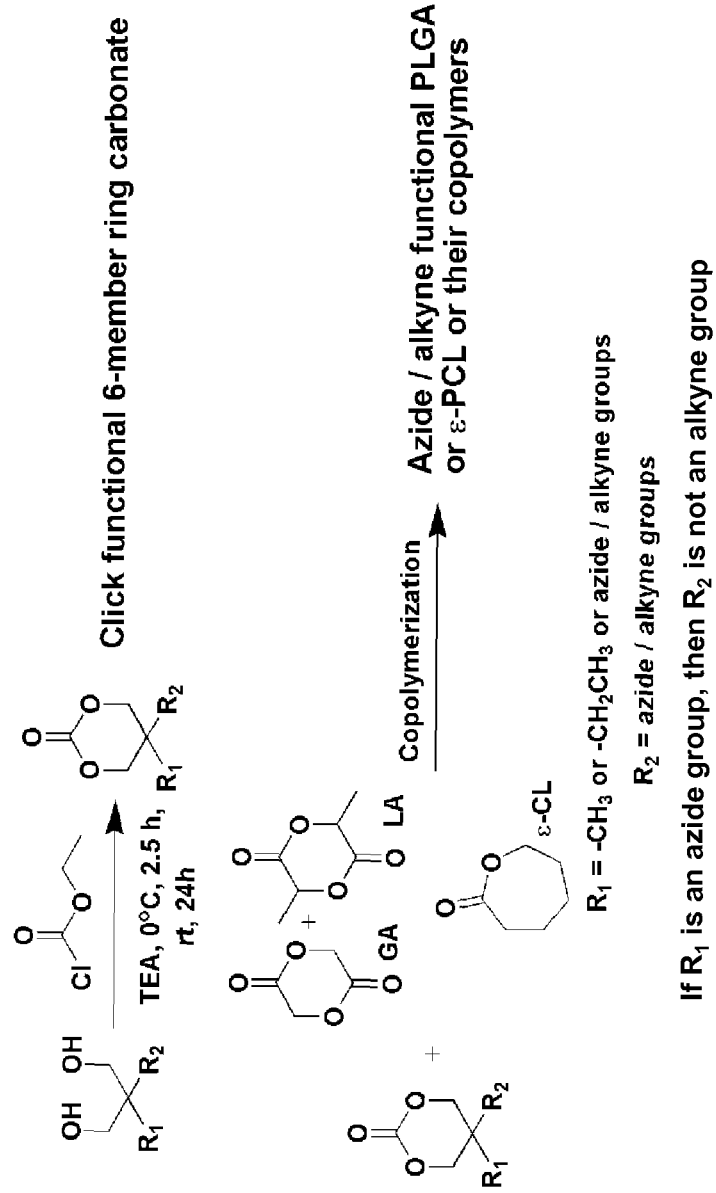
FIG. 1 illustrates a reaction scheme for making a composition according to one embodiment described herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Compositions

In one aspect, compositions are described herein. In some embodiments, a composition comprises the reaction product of (i) citric acid, a citrate, or an ester of citric acid, such as triethyl citrate or another methyl or ethyl ester of citric acid, with (ii) a polyol such as a diol and (iii) a monomer comprising an alkyne moiety and/or an azide moiety. Non-limiting examples of polyols suitable for use in some embodiments described herein include C2-C20, C2-C12, or C2-C6 aliphatic alkane diols, including α,ω-n-alkane diols, or α,ω-alkene diols. For instance, in some cases, a polyol comprises 1,4-butanediol, 1,6-hexanediol, 1,8-octanediol, 1,10-decanediol, 1,12-dodecanediol, 1,16-hexadecanediol, or 1,20-icosanediol. Branched α,ω-alkane diols or α,ω-alkene diols can also be used. Additionally, a polyol can also be an aromatic diol. Further, in some embodiments, a polyol comprises a poly(ethylene glycol) (PEG) or poly(propylene glycol) (PPG). Any PEG or PPG not inconsistent with the objectives of the present disclosure may be used. In some embodiments, for instance, a PEG or PPG has a weight average molecular weight between about 100 and about 5000 or between about 200 and about 1000.

Moreover, in some instances, the polyol above can be at least partially replaced by an alcohol having only one hydroxyl group or by an amine or an amide. Further, in some cases, the polyol can be at least partially replaced by a polymer or oligomer having one or more hydroxyl, amine, or amide groups. Such a polymer or oligomer, in some instances, can be a polyester, polyether, or polyamide. Thus, in some embodiments, a composition described herein comprises the reaction product of (i) citric acid, a citrate, or an ester of citric acid with (ii) an alcohol, amine, amide, polyester, polyether, or polyamide and (iii) a monomer comprising an alkyne moiety and/or an azide moiety.

In some cases, a composition comprises a polymer formed from one or more monomers of Formula (A); one or more monomers of Formula (B1), (B2), or (B3); and one or more monomers comprising one or more alkyne moieties and/or one or more azide moieties:

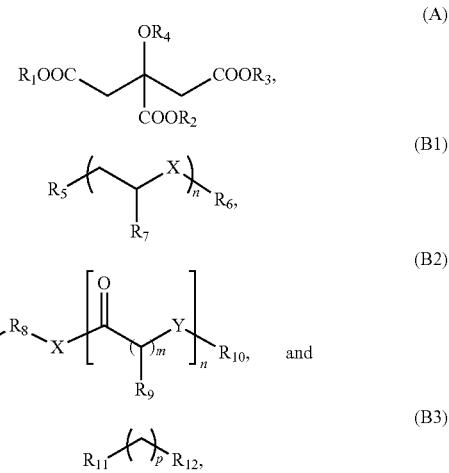

wherein
$R_1$, $R_2$, and $R_3$ are independently —H, —$CH_3$, —$CH_2CH_3$, or $M^+$;
$R_4$ is —H;
$R_5$ is —H, —OH, —$OCH_3$, —$OCH_2CH_3$, —$CH_3$, —$CH_2CH_3$, —$NH_2$, $NHCH_3$, —$CH_2CH_2NHCH_3$, —$N(CH_3)_2$, or —$CH_2CH_2N(CH_3)_2$;
$R_6$ is —H, —$CH_3$, or —$CH_2CH_3$, —$(CH_3)_2$, or —$(CH_2CH_3)_2$;
$R_7$ is —H or —$CH_3$;
$R_8$ is —$(CH_2)_a$—, —$(CH_2CH_2O)_b$— or —$(CH_2OCH_2)_b$—;
$R_9$ is —H, —$CH_3$, or a C2-C20 alkyl;
$R_{10}$ is —H, —$C(O)CH_3$, or —$C(O)CH_2CH_3$;
$R_{11}$ and $R_{12}$ are independently —OH or —$NH_2$;
$M^+$ is a monovalent cation;
X and Y are independently —O— or —NH—;
Z is —H, —$CH_3$, —$(CH_3)_2$, —$(CH_2CH_3)_2$, or

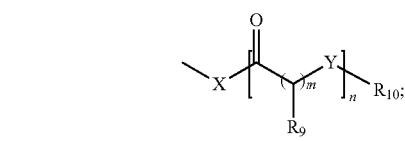

a is an integer from 0 to 20;
b is an integer from 0 to 2000;
n is an integer between 1 and 2000; and
m and p are independently integers ranging from 1 to 20; and
wherein the monomer of Formula (B1) has at least one terminus comprising —OH or —$NH_2$.

In some embodiments, one or more monomers of Formula (B1) is used, and X is —O—. Thus, in some cases, a monomer of Formula (B1) comprises

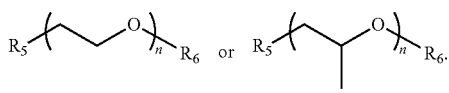

Further in some instances, a monomer of Formula (B3) is used, and $R_{11}$ and $R_{12}$ are each —OH. In some embodiments, a monomer of Formula (B3) comprises

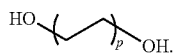

The monomers of Formula (A), (B1), (B2), and (B3) and the monomers comprising one or more alkyne and/or azide moieties can be used in any ratio not inconsistent with the objectives of the present disclosure. In addition, altering the ratios of monomers can, in some embodiments, alter the biodegradability, the mechanical strength, and/or other properties of the polymer formed from the monomers. In some embodiments, the ratio of monomer (A) to monomer (B1), (B2), or (B3) is between about 1:10 and about 10:1 or between about 1:5 and about 5:1. In some embodiments, the ratio of monomer (A) to monomer (B1), (B2), or (B3) is between about 1:4 and about 4:1. In some embodiments, the ratio is about 1:1. The ratio of an alkyne or azide-containing monomer to a monomer of Formula (A), (B1), (B2), or (B3) can be between about 1:20 and 1:2 or between about 1:10 and about 1:3.

Further, a reaction product described herein, in some cases, is a condensation polymerization or polycondensation reaction product of the identified monomer or species. In some such embodiments, the reaction product forms an alternating copolymer or a statistical copolymer of the comonomers. Additionally, as described further herein, species described hereinabove may also form pendant groups or side chains of a copolymer. A "monomer," for reference purposes herein, can comprise a chemical species having at least two functional groups or points of attachment to a polymer backbone, such that the monomer can be used, alone or in combination with a different type of monomer, to provide a polymerization product.

Moreover, it is to be understood that a "polymer" of a composition described herein may be a polymer or an oligomer. Further, in some cases, a polymer of a composition described herein may also be a prepolymer, where a "prepolymer" can refer to a polymerizable species of a relatively low molecular weight that can form a larger polymer or polymer network. Thus, in some embodiments, a "polymer" of a composition described herein has a weight average molecular weight of less than about 5000, less than about 3000, less than about 2000, less than about 1000, or less than about 500. In other cases, a polymer of a composition described herein has a weight average molecular weight greater than about 1000, greater than about 2000, greater than about 3000, or greater than about 5000. In some instances, a polymer of a composition described herein has a weight average molecular weight between about 500 and about 10,000, between about 500 and about 5000, between about 1000 and about 10,000, or between about 2000 and about 10,000. A polymer of a composition described herein can have other molecular weights as well.

In addition, a "citrate-containing" or "citrate-based" polymer can refer to a polymer at least partially formed from a monomer of Formula (A) and/or containing a moiety having Formula (A). When a polymer comprises a moiety of Formula (A), $R_1$, $R_2$, and $R_3$ can further represent a point of attachment to the remainder of the polymer.

Further, in some embodiments, a polymer of a composition described herein is formed from one or more additional monomers in addition to those recited above. For example, in some cases, a polymer of a composition described herein can comprise the reaction product of (i) citric acid, a citrate, or an ester of citric acid with (ii) a polyol, (iii) one or more alkynes and/or azides, and (iv) an amine, an amide, or an isocyanate. In such instances, the polyol can comprise any polyol described above, and the ester of citric acid can comprise any ester of citric acid described above. Further, an amine, in some embodiments, comprises one or more primary amines having two to ten carbon atoms. In other cases, an amine comprises one or more secondary or tertiary amines having two to fifteen carbon atoms. An isocyanate, in some embodiments, comprises a monoisocyanate. In other instances, an isocyanate comprises a diisocyanate such as an alkane diisocyanate having four to twenty carbon atoms. For example, in some embodiments, the polymer of a composition is formed from one or more monomers of Formula (A); one or more monomers of Formula (B1), (B2), or (B3); one or more monomers comprising one or more alkyne moieties and/or one or more azide moieties; and one or more monomers of Formula (C1), (C2), (C3), or (C4):

(C1)

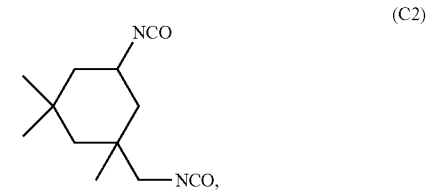

(C2)

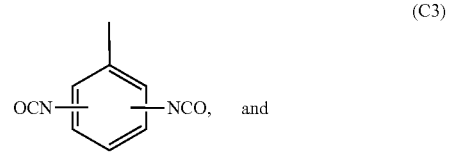

(C3)

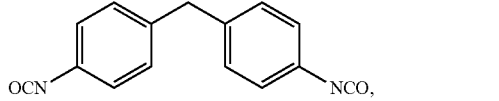

(C4)

wherein
p is an integer ranging from 1 to 10.

Moreover, the monomers of Formula (A), (B1), (B2), (B3), (C1), (C2), (C3), and (C4) and the monomers comprising one or more alkyne and/or azide moieties can be used in any ratio not inconsistent with the objectives of the present disclosure. In addition, altering the ratios of monomers can, in some embodiments, alter the biodegradability, the mechanical strength, and/or other properties of the polymer formed from the monomers. In some embodiments, the ratio of monomer (A) to monomer (B1), (B2), or (B3) is between about 1:10 and about 10:1 or between about 1:5 and about 5:1. In some embodiments, the ratio of monomer (A) to monomer (B1), (B2), or (B3) is between about 1:4 and about 4:1. In some embodiments, the ratio is about 1:1. Further, in some embodiments, the ratio of monomer (A) to monomer (C) is between about 1:10 and about 10:1. In some embodiments, the ratio of monomer (A) to monomer (C1), (C2), (C3), or (C4) is about 1:1. The ratio of an alkyne or azide-containing monomer to a monomer of Formula (A), (B1), (B2), (B3), (C1), (C2), (C3), or (C4) can be between about 1:20 and 1:2 or between about 1:10 and about 1:3.

In addition, in some embodiments described herein, a monomer of Formula (B1), (B2), or (B3) can be replaced by an alcohol that does not have the formula of Formula (B1), (B2), or (B3). For example, in some embodiments, an unsaturated alcohol or an unsaturated polyol can be used. Moreover, in some cases, a monomer of Formula (C) can be at least partially replaced by an amino acid described herein.

Similarly, in other cases, a polymer comprises the reaction product of (i) citric acid, a citrate, or an ester of citric acid with (ii) a polyol, (iii) one or more alkynes and/or azides, and (iv) a polycarboxylic acid such as a dicarboxylic acid or a functional equivalent of a polycarboxylic acid, such as a cyclic anhydride or an acid chloride of a polycarboxylic acid. In such cases, the polyol can comprise any polyol described above, and the ester of citric acid can comprise any ester of citric acid described above. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. A vinyl-containing polycarboxylic acid or functional equivalent thereof may also be used, such as allylmalonic acid, allylmalonic chloride, itaconic acid, or itaconic chloride. Further, in some cases, the polycarboxylic acid or functional equivalent thereof can be at least partially replaced with an olefin-containing monomer that may or may not be a polycarboxylic acid. In some embodiments, for instance, an olefin-containing monomer comprises an unsaturated polyol such as a vinyl-containing diol. In some instances, a polymer of a composition described herein is formed from one or more monomers of Formula (A); one or more monomers of Formula (B1), (B2), or (B3); one or more monomers comprising one or more alkyne moieties and/or one or more azide moieties; and one or more monomers of Formula (D1) or (D2):

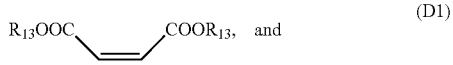

(D1)

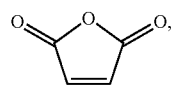

(D2)

wherein
$R_{13}$ is —H, —$CH_3$, or —$CH_2CH_3$.

Further, the monomers of Formula (A), (B1), (B2), (B3), (D1), and (D2) and the monomers comprising one or more alkyne and/or azide moieties can be used in any ratio not inconsistent with the objectives of the present disclosure. In addition, altering the ratios of monomers can, in some embodiments, alter the mechanical properties and/or other properties of the polymer formed from the monomers. In some embodiments, the ratio of monomer (A) to monomer (B1), (B2), or (B3) is between about 1:10 and about 10:1 or between about 1:5 and about 5:1. In some embodiments, the ratio of monomer (A) to monomer (B1), (B2), or (B3) is between about 1:4 and about 4:1. In some cases, the ratio is about 1:1. Further, in some embodiments, the ratio of monomer (A) to monomer (D1) or monomer (D2) is between about 1:10 and about 10:1. In some embodiments, the ratio of monomer (A) to monomer (D1) or monomer (D2) is about 1:1. The ratio of an alkyne or azide-containing monomer to a monomer of Formula (A), (B1), (B2), (B3), (D1) or (D2) can be between about 1:20 and 1:2 or between about 1:10 and about 1:3.

In still other embodiments, the polymer of a composition described herein comprises the reaction product of (i) citric acid, a citrate, or an ester of citric acid with (ii) a polyol, (iii) one or more alkynes and/or azides, and (iv) an amino acid such as an alpha-amino acid. Further, in some cases, a polymer described herein comprises the reaction product of (i) citric acid, a citrate, or an ester of citric acid with (ii) a polyol, (iii) one or more alkynes and/or azides, (iv) an amino acid, and (v) an isocyanate such as a diisocyanate. Additionally, in some instances, an acid anhydride and/or an acid chloride can be used in conjunction with the citric acid, citrate, or ester of citric acid. The polyol can be any polyol described above, the ester of citric acid can be any ester of citric acid described above, and the isocyanate can be any isocyanate described above. Further, the acid anhydride and/or acid chloride can include any acid anhydride and/or acid chloride described above, including, or instance, a polyacid anhydride or a polyacid chloride.

An alpha-amino acid of a polymer described herein, in some embodiments, comprises an L-amino acid, a D-amino acid, or a D,L-amino acid. In some cases, an alpha-amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof. Further, in some instances, an alpha-amino acid comprises an alkyl-substituted alpha-amino acid, such as a methyl-substituted amino acid derived from any of the 22 "standard" or proteinogenic amino acids, such as methyl serine. Additionally, in some cases, an amino acid forms a pendant group or side group of the polymer of a composition described herein. Such an amino acid pendant group can be bonded to the backbone of the polymer in any manner not inconsistent with the objectives of the present disclosure. For example, in some cases, the amino acid is bonded to the backbone through an ester and/or amide bond between the amino acid and the citrate moiety. Moreover, in some instances, the amino acid forms a 6-membered ring with the citrate moiety. Not intending to be bound by theory, it is believed that the formation of a 6-membered ring described herein can provide fluorescence to the polymer. Thus, in some embodiments, the polymer of a composition described herein can be a fluorescent polymer.

In some cases, the polymer of a composition described herein is formed from one or more monomers of Formula (A); one or more monomers of Formula (B1), (B2) or (B3); one or more monomers comprising one or more alkyne moieties and/or one or more azide moieties; and one or more monomers of Formula (E):

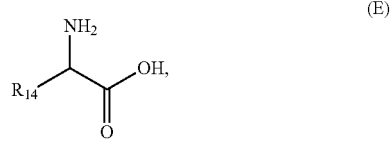

(E)

wherein $R_{14}$ is an amino acid side chain.

Moreover, the monomers of Formula (A), (B1), (B2), (B3), and (E) and the monomers comprising one or more alkyne and/or azide moieties can be used in any ratio not inconsistent with the objectives of the present disclosure. In addition, altering the ratios of monomers can, in some embodiments, alter the mechanical, luminescence, and/or other properties of the polymer formed from the monomers. In some embodiments, the ratio of monomer (A) to monomer (B1), monomer (B2), or monomer (B3) is between about 1:10 and about 10:1 or between about 1:5 and about 5:1. In some embodiments, the ratio of monomer (A) to monomer (B1), monomer (B2), or monomer (B3) is between about 1:4 and about 4:1. In some cases, the ratio is about 1:1. Further, in some embodiments, the ratio of monomer (A) to monomer (E) is between about 1:10 and about 10:1. The ratio of an alkyne or azide-containing monomer to a monomer of Formula (A), (B1), (B2), (B3), or (E) can be between about 1:20 and 1:2 or between about 1:10 and about 1:3.

In other instances, a polymer of a composition described herein comprises the reaction product of (i) citric acid, a citrate, or an ester of citric acid with (ii) a polyol, (iii) one or more alkynes and/or azides, and (iv) a catechol-containing species. The citrate or ester of citric acid can be any citrate or ester of citric acid described above, such as a methyl or ethyl ester of citric acid. Similarly, the polyol can be any polyol described above.

The catechol-containing species can comprise any catechol-containing species not inconsistent with the objectives of the present disclosure. In some cases, a catechol-containing species used to form a polymer described herein comprises at least one moiety that can form an ester or amide bond with another chemical species used to form the polymer. For example, in some cases, a catechol-containing species comprises an amine moiety or a carboxylic acid moiety. Further, in some instances, a catechol-containing species comprises a hydroxyl moiety that is not part of the catechol moiety. In some embodiments, a catechol-containing species comprises dopamine. In other embodiments, a catechol-containing species comprises L-3,4-dihydroxyphenylalanine (L-DOPA) or D-3,4-dihydroxyphenylalanine (D-DOPA). In some cases, a catechol-containing species comprises 3,4-dihydroxyhydrocinnamic acid. Moreover, in some embodiments, a catechol-containing species is coupled to the backbone of the polymer through an amide bond. In other embodiments, a catechol-containing species is coupled to the backbone of the polymer through an ester bond.

In some cases, a polymer of a composition described herein is formed from one or more monomers of Formula (A); one or more monomers of Formula (B1), (B2) or (B3); one or more monomers comprising one or more alkyne moieties and/or one or more azide moieties; and one or more monomers of Formula (F):

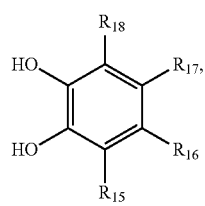

(F)

wherein
$R_{15}$, $R_{16}$, $R_{17}$, and $R_{18}$ are independently —H, —$CH_2(CH_2)_xNH_2$, —$CH_2(CHR_{19})NH_2$, or —$CH_2(CH_2)_xCOOH$;
$R_{19}$ is —COO or —$(CH_2)_yCOO$;
x is an integer ranging from 0 to 20; and
y is an integer ranging from 1 to 20.

Moreover, the monomers of Formula (A), (B1), (B2), (B3), and (F) and the monomers comprising one or more alkyne and/or azide moieties can be used in any ratio not inconsistent with the objectives of the present disclosure. In addition, altering the ratios of monomers can, in some embodiments, alter the mechanical properties and/or other properties of the polymer formed from the monomers. In some embodiments, the ratio of monomer (A) to monomer (B1), (B2), or (B3) is between about 1:10 and about 10:1 or between about 1:5 and about 5:1. In some embodiments, the ratio of monomer (A) to monomer (B1), (B2), or (B3) is between about 1:4 and about 4:1. In some cases, the ratio is about 1:1. Further, in some embodiments, the ratio of monomer (A) to monomer (F) is between about 1:10 and about 10:1. The ratio of an alkyne or azide-containing monomer to a monomer of Formula (A), (B1), (B2), (B3), or (F) can be between about 1:20 and 1:2 or between about 1:10 and about 1:3.

Further, monomers comprising one or more alkyne and/or azide moieties used to form a polymer described herein can comprise any alkyne- and/or azide-containing chemical species not inconsistent with the objectives of the present disclosure. For example, in some instances, one or more such monomers comprises a polyol such as a diol. Such a monomer, in some cases, can be incorporated into the polymer through the reaction of one or more hydroxyl moieties of the monomer with a carboxyl or carboxylic acid moiety of a monomer of Formula (A) or of another carboxyl-containing monomer described herein. Moreover, in some instances, such a monomer can be used instead of the monomer of Formula (B1), (B2), or (B3). In other instances, such a monomer is used in conjunction with one or more monomers of Formula (B1), (B2), or (B3). Further, such a monomer can be a diazido-diol (DAzD) or an alkyne diol (AlD).

In some cases, one or more monomers comprising one or more azide moieties comprises a monomer of Formula (G1) or (G2):

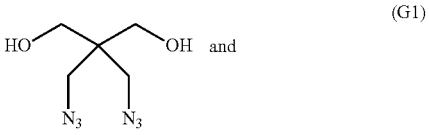

(G1)

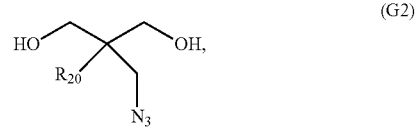

(G2)

wherein
$R_{20}$ is —$CH_3$ or —$CH_2CH_3$.

Further, in some embodiments, one or more monomers comprising one or more alkyne moieties comprises a monomer of Formula (H1), (H2), (H3), (H4), (H5), or (H6):

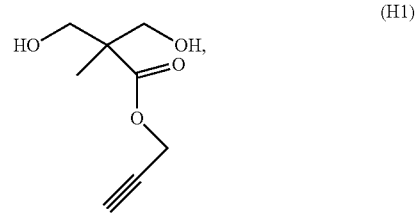

(H1)

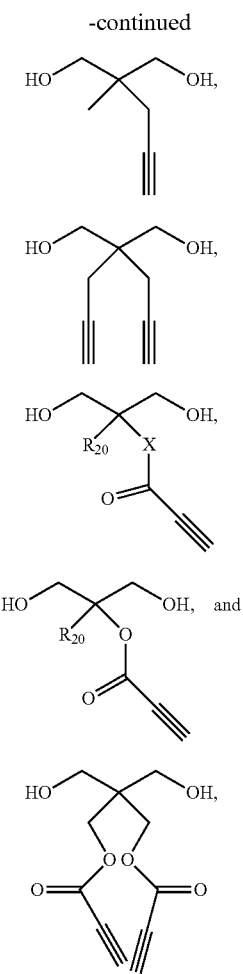

wherein
R$_{20}$ is —CH$_3$ or —CH$_2$CH$_3$; and
X is —NH— or —O—.

Additionally, in some embodiments, a polymer described herein can be functionalized with a bioactive species. In some cases, the polymer is formed from an additional monomer comprising the bioactive species. Moreover, such an additional monomer can comprise one or more alkyne and/or azide moieties. For example, in some instances, a polymer described herein is formed from one or more monomers comprising a peptide, polypeptide, nucleic acid, or polysaccharide, wherein the peptide, polypeptide, nucleic acid, or polysaccharide is functionalized with one or more alkyne and/or azide moieties. In some cases, the bioactive species of a polymer described herein is a growth factor or signaling molecule. Further, a peptide can comprise a dipeptide, tripeptide, tetrapeptide, or a longer peptide. As described further hereinbelow, forming a polymer from such a monomer, in some embodiments, can provide additional biological functionality to a composition described herein.

In addition, in some embodiments, a composition comprises a plurality of polymers described herein. In some instances, the polymers are selected to be reactive with one another through a click chemistry reaction scheme. In some cases, for example, a composition described herein comprises a first polymer formed from one or more monomers of Formula (A); one or more monomers of Formula (B1), (B2), or (B3); and one or more monomers comprising one or more alkyne moieties; and further comprises a second polymer formed from one or more monomers of Formula (A); one or more monomers of Formula (B1), (B2), or (B3); and one or more monomers comprising one or more azide moieties. Thus, in some such embodiments, a composition described herein can comprise an azide-alkyne cycloaddition product, such as a 1,4 or 1,5-triazole ring. In this manner, a first polymer and a second polymer of a composition described herein can form a polymer network by forming one or more azide-alkyne cycloaddition products to serve as cross-links of the polymer network.

Such a polymer network can have a high cross-linking density. "Cross-linking density," for reference purposes herein, can refer to the number of cross-links between polymer backbones or the molecular weight between cross-linking sites, calculated as described hereinbelow. Further, in some embodiments, the cross-links of a polymer network described herein comprise azide-alkyne cycloaddition product cross-links. Cross-links may also include ester bonds formed by the esterification or reaction of one or more pendant carboxyl or carboxylic acid groups with one or more pendant hydroxyl groups of adjacent polymer backbones. In some embodiments, a polymer network described herein has a cross-linking density of at least about 500, at least about 1000, at least about 5000, at least about 7000, at least about 10,000, at least about 20,000, or at least about 30,000 mol/m$^3$. In some cases, the cross-linking density is between about 5000 and about 40,000 or between about 10,000 and about 40,000 mol/m$^3$.

It is also possible to form a polymer network using a click chemistry reaction scheme that does not necessarily form azide-alkyne cycloaddition products. For instance, in some cases, one or more monomers comprising an alkyne and/or azide moiety described herein can be at least partially replaced by one or more monomers comprising a different moiety that can participate in a click chemistry reaction scheme. For example, in some embodiments, a polymer or polymer network is formed from the reaction of one or more monomers comprising a thiol moiety with one or more monomers comprising an alkene (or alkyne) moiety through a thiol-ene/yne click reaction. Such a thiol-ene/yne click reaction can comprise the addition of an S—H bond across a carbon-carbon double bond or triple bond by a free radical or ionic mechanism. More generally, in some cases, a polymer described herein can be formed from one or more monomers of Formula (A); one or more monomers of Formula (B1), (B2), or (B3); and one or more monomers comprising one or more first moieties operable to participate in a click chemistry reaction and/or one or more second moieties operable to participate in the same click chemistry reaction, where the first and second moieties differ. Any click chemistry reaction not inconsistent with the objectives of the present disclosure may be used. In some instances, the click chemistry reaction comprises a [3+2] cycloaddition such as a Huisgen alkyne-azide cycloaddition; a thiol-ene/yne reaction; a Diels-Alder reaction; an inverse electron demand Diels-Alder reaction; a [4+1] cycloaddition such as the cycloaddition reaction of an isocyanide with a tetrazine; or a nucleophilic substitution reaction involving a strained ring such as an epoxy or aziridine ring. Not intending to be bound by theory, it is believed that the use of a click chemistry reaction scheme to provide cross-linking in a polymer network can, in some cases, improve the mechanical strength of a polymer network without sacrificing pendant citric acid carboxyl moieties for other purposes, such as hydroxyapatite (HA) calcium chelation.

Further, it is to be understood that a polymer or polymer network described herein can be formed from monomers that are not necessarily monomers having the structure of Formula (A), (B1), (B2), or (B3). For example, in some cases, a polymer of a composition described herein is formed from one or more monomers comprising a lactone and one or more monomers comprising one or more moieties operable to participate in a click reaction, such as one or more alkyne moieties and/or one or more azide moieties. In some such cases, the one or more monomers comprising a lactone can comprise at least about 60 mol %, at least about 70 mol %, at least about 80 mol %, at least about 90 mol %, at least about 95 mol %, or at least about 99 mol % of the monomers used to form the polymer, based on the total amount of all monomers. Thus, in some instances, a polymer of a composition described herein comprises a polylactone that has been modified to include one or more clickable moieties such as one or more azide moieties and/or one or more alkyne moieties, including as pendant or side groups of the polymer. Any lactone not inconsistent with the objectives of the present disclosure may be used to form such a polymer. For example, in some cases, a lactone comprises L-lactide, D-lactide, D,L-lactide, glycolide, and/or ε-caprolactone. Thus, in some instances, a polymer described herein can be a poly(ε-caprolactone) (PCL), a poly(lactic-co-glycolic acid) (PLGA), or a combination thereof.

Similarly, in other embodiments, a polymer of a composition described herein is formed from one or more monomers comprising a polycarboxylic acid or a functional equivalent of a polycarboxylic acid that differs from a species described by Formula (A). Such a polycarboxylic acid can be a dicarboxylic acid, and a "functional equivalent" of a polycarboxylic acid can be a species that forms the same polymer product as a polycarboxylic acid does in a reaction scheme described herein, such as a cyclic anhydride or an acid chloride of a polycarboxylic acid described herein. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. A vinyl-containing polycarboxylic acid or functional equivalent thereof may also be used, such as allylmalonic acid, allylmalonic chloride, itaconic acid, or itaconic chloride.

In some cases, a polymer is formed from one or more such monomers comprising a polycarboxylic acid or polycarboxylic acid equivalent; one or more monomers comprising a polyol; and one or more monomers comprising one or more clickable moieties, such as one or more alkyne moieties and/or one or more azide moieties. For instance, in some cases, the polycarboxylic acid comprises a dicarboxylic acid such as sebacic acid. Similarly, the polyol can comprise a diol such as a diol provided above or a triol such as glycerol. Further, in some such cases, the one or more monomers comprising one or more clickable moieties such as one or more alkyne and/or azide moieties can comprise up to about 40 mol %, up to about 30 mol %, up to about 20 mol %, up to about 10 mol %, up to about 5 mol %, or up to about 1 mol % of the monomers used to form the polymer, based on the total amount of all monomers. Thus, in some instances, a polymer of a composition described herein comprises a polyester such as poly(glycerol sebacate) (PGS) that has been modified to include one or more azide moieties and/or one or more alkyne moieties, including as a pendant or side group of the polymer.

In addition, a polymer network described herein can be a hydrogel. A hydrogel, in some cases, comprises an aqueous continuous phase and a polymeric disperse or discontinuous phase. Further, in some embodiments, a cross-linked polymer network described herein is not water soluble.

A polymer or polymer network described herein, in some cases, can also have at least one ester bond in the backbone of the polymer. In some instances, a polymer has a plurality of ester bonds in the backbone of the polymer, such as at least three ester bonds, at least four ester bonds, or at least five ester bonds. In some embodiments, a polymer described herein has between two ester bonds and fifty ester bonds in the backbone of the polymer. Further, polymers and polymer networks having a structure described herein, in some cases, can be biodegradable. A biodegradable polymer or polymer network, in some embodiments, degrades in vivo to non-toxic components which can be cleared from the body by ordinary biological processes. In some embodiments, a biodegradable polymer completely or substantially completely degrades in vivo over the course of about 90 days or less, about 60 days or less, or about 30 days or less, where the extent of degradation is based on percent mass loss of the biodegradable polymer, and wherein complete degradation corresponds to 100% mass loss. Specifically, the mass loss is calculated by comparing the initial weight ($W_0$) of the polymer with the weight measured at a pre-determined time point ($W_t$) (such as 30 days), as shown in Equation (1):

$$\text{Mass loss (\%)} = \frac{(W_0 - W_t)}{W_0} \times 100. \qquad (1)$$

Further, a polymer or polymer network described herein can be present in a composition in any amount not inconsistent with the objectives of the present disclosure. In some cases, a composition consists or consists essentially of the polymer or polymer network. In other instances, a composition comprises up to about 95 weight percent, up to about 90 weight percent, up to about 80 weight percent, up to about 70 weight percent, up to about 60 weight percent, up to about 50 weight percent, up to about 40 weight percent, or up to about 30 weight percent polymer or polymer network, based on the total weight of the composition. In some instances, a composition described herein comprises between about 10 weight percent and about 99 weight percent, between about 10 weight percent and about 90 weight percent, between about 10 weight percent and about 80 weight percent, between about 20 weight percent and about 70 weight percent, between about 30 weight percent and about 70 weight percent, between about 30 weight percent and about 60 weight percent, between about 50 weight percent and about 99 weight percent, between about 50 weight percent and about 80 weight percent, or between about 60 weight percent and about 90 weight percent polymer or polymer network, based on the total weight of the composition. Further, in some embodiments, the balance of a composition described herein can be water or an aqueous solution.

Moreover, in some embodiments, a composition described herein comprising a polymer network can further comprise a particulate material dispersed in the polymer network. Any particulate material not inconsistent with the objectives of the present disclosure may be used. In some cases, the particulate material comprises one or more of hydroxyapatite, tricalcium phosphate, biphasic calcium phosphate, bioglass, ceramic, magnesium powder, magnesium alloy, and decellularized bone tissue particles. Other particulate materials may also be used.

In addition, a particulate material described herein can have any particle size and/or particle shape not inconsistent with the objectives of the present disclosure. In some embodiments, for instance, a particulate material has an average particle size in at least one dimension of less than about 1000 μm, less than about 800 μm, less than about 500 μm, less than about 300 μm, less than about 100 μm, less than about 50 μm, less than about 30 μm, or less than about 10 μm. In some cases, a particulate material has an average particle size in at least one dimension of less than about 1 μm, less than about 500 nm, less than about 300 nm, less than about 100 nm, less than about 50 nm, or less than about 30 nm. In some instances, a particulate material has an average particle size recited herein in two dimensions or three dimensions. Moreover, a particulate material can be formed of substantially spherical particles, plate-like particles, needle-like particles, or a combination thereof. Particulate materials having other shapes may also be used.

A particulate material can be present in a composition described herein in any amount not inconsistent with the objectives of the present disclosure. For example, in some cases, a composition comprises up to about 70 weight percent, up to about 60 weight percent, up to about 50 weight percent, up to about 40 weight percent, or up to about 30 weight percent particulate material, based on the total weight of the composition. In some instances, a composition comprises between about 1 and about 70 weight percent, between about 10 and about 70 weight percent, between about 15 and about 60 weight percent, between about 25 and about 65 weight percent, between about 25 and about 50 weight percent, between about 30 and about 70 weight percent, between about 30 and about 50 weight percent, between about 40 and about 70 weight percent, or between about 50 and about 70 weight percent, based on the total weight of the composition. For example, in some cases, a composition comprising a polymer network described herein comprises up to about 65 weight percent hydroxyapatite.

Moreover, in some embodiments, a composition described herein can comprise a high amount of particulate material, such as an amount up to about 70 weight percent, even when the polymers used to form the polymer network have a low weight average molecular weight, such as a weight average molecular weight of less than about 2000, less than about 1000, or less than about 500. For example, in some instances, a composition described herein comprises a polymer network formed from a polymer described herein having a weight average molecular weight of less than about 2000, less than about 1000, or less than about 500, and further comprises hydroxyapatite particles dispersed in the polymer network in an amount up to about 70 weight percent. Additionally, in some cases, the polymer network is not cross-linked or substantially cross-linked, other than by any cross-linking that may be provided by the hydroxyapatite particles.

Further, a particulate material described herein can be dispersed in a polymer network in any manner not inconsistent with the objectives of the present disclosure. In some embodiments, for instance, the particulate material is mixed or ground into the polymer network. In addition, a particulate material described herein, in some cases, can be chelated or otherwise bound by one or more pendant functional groups of the polymer network. For instance, in some cases, a composition comprises hydroxyapatite particles dispersed in a polymer network described herein, wherein the hydroxyapatite is chelated by one or more pendant functional groups of the polymer network. In some embodiments, one or more carboxyl moieties or one or more citrate moieties of the polymer network chelate one or more calcium-containing portions of the hydroxyapatite.

A polymer network described herein can be prepared in any manner not inconsistent with the objectives of the present disclosure. In some cases, a method of making a polymer network comprises mixing and/or reacting a first polymer and a second polymer, the first and second polymer each comprising a polymer of a composition described herein. Moreover, the first and second polymers can comprise complementary functional groups for carrying out a cross-linking reaction, including through a click chemistry reaction scheme. For example, in some instances, the first polymer comprises one or more alkyne moieties, and the second polymer comprises one or more azide moieties. In some cases, the first polymer is formed from one or more monomers of Formula (A); one or more monomers of Formula (B1), (B2), or (B3); and one or more monomers comprising one or more alkyne moieties; and the second polymer is formed from one or more monomers of Formula (A); one or more monomers of Formula (B1), (B2), or (B3); and one or more monomers comprising one or more azide moieties. In such cases, the polymer network may be formed by reacting the one or more alkyne moieties of the first polymer with the one or more azide moieties of the second polymer to form one or more azide-alkyne cycloaddition products.

Reacting the alkyne and azide moieties can be carried out in any manner not inconsistent with the objectives of the present disclosure. In some embodiments, reacting the alkyne and azide moieties comprises heating the mixture of the first and second polymers to a temperature sufficient to induce a cross-linking reaction, such as a temperature of about 80° C. to about 120° C. to induce a thermal click chemistry reaction or an esterification reaction. Alkyne and azide moieties may also be reacted by providing a catalyst to the mixture, such as a metal catalyst. A metal catalyst suitable for use in some embodiments described herein can include one or more of copper, ruthenium, and silver. In other instances, a metal-containing catalyst such as a copper catalyst is not used. Further, reacting the alkyne and azide moieties of first and second polymers described herein can comprise inducing a click chemistry reaction between the azide and alkyne moieties. Such a click chemistry reaction can be a thermal click chemistry reaction or another type of click chemistry reaction, such as a strain promoted alkyne-azide cycloaddition (SPAAC) or a copper-catalyzed alkyne-azide cycloaddition (CuAAC). Moreover, carrying out a reaction between alkyne and azide moieties in a manner described herein can form a cross-linked polymer network, the cross-links of the network being formed by azide-alkyne cycloaddition reaction products such as 1,4- or 1,5-triazole rings. Additionally, in some embodiments, the first and/or second polymers can comprise one or more additional moieties that can form additional cross-links to provide a polymer network. For example, in some cases, the first polymer and/or the second polymer comprises one or more carboxylic acid groups and/or hydroxyl groups. In some such instances, additional cross-linking can occur through the formation of one or more ester bonds between the carboxylic acid and hydroxyl groups.

Moreover, in some embodiments, a method of making a polymer network described herein further comprises functionalizing the surface of the polymer network with one or more biofunctional species, such as one or more peptides, polypeptides, nucleic acids, and/or polysaccharides. Such functionalization can be carried out in any manner not inconsistent with the objectives of the present disclosure. For example, in some instances, a method described herein further comprises reacting one or more of a peptide, polypeptide, nucleic acid, and polysaccharide with a pendant alkyne and/or azide moiety on the cross-linked polymer network to provide a covalent bond between the cross-linked polymer network and the peptide, polypeptide, nucleic acid, and/or polysaccharide. In some cases, the peptide, polypeptide, nucleic acid, and/or polysaccharide comprises an alkyne or azide moiety, and formation of a covalent bond is carried out by inducing a further click chemistry reaction, such as a strain-promoted alkyne-azide cycloaddition reaction, between one or more alkyne and/or azide moieties of the polymer network and one or more alkyne and/or azide moieties of the peptide, polypeptide, nucleic acid, and/or polysaccharide. Such a reaction, in some instances, can be carried out at 37° C. in an aqueous environment. Additionally, a peptide, polypeptide, or other biofunctional species can be modified to be clickable by reacting the peptide, polypeptide, or other species with a reagent such as a Click-easy® BCN N-hydroxysuccinimide ester, commercially available from Berry & Associates.

Various components of compositions have been described herein. It is to be understood that a composition according to the present disclosure can comprise any combination of components and features not inconsistent with the objectives of the present disclosure. Additionally, in some embodiments, such a combination can be selected to provide a composition having any biodegradability, mechanical property, and/or chemical functionality described herein.

II. Medical Implants and Devices

In another aspect, medical implants and devices are described herein. In some embodiments, a medical implant or medical device comprises or is formed from a composition described hereinabove in Section I. Any composition described hereinabove in Section I may be used. Further, in some cases, a medical implant described herein comprises a tissue engineering scaffold. A medical implant described herein can also comprise or form a soft tissue structure, such as a blood vessel, a cardiac tissue, a heart valve, a ligament, a tendon, a lung, a bladder, skin, a trachea, or a urethra. In addition, compositions described herein may also be formed into microfibers or nanofibers having a diameter of less than about 1000 µm or less than about 1000 nm, respectively.

In some embodiments, a composition described herein comprises a biphasic polymeric scaffold. A "biphasic" scaffold, for reference purposes herein, can have a two-component structure, such as a core-shell structure, wherein the two components have differing chemical and/or mechanical properties. In some cases, for instance, a core-shell polymeric scaffold described herein comprises a core component having a first porosity; and a shell component surrounding the core component and having a second porosity, the second porosity differing from the first porosity. Additionally, in some such embodiments, the core component exhibits a higher porosity than the shell component. For example, in some cases, the first porosity is between about 30% and about 99% and the second porosity is between about 0% and about 99%. In some embodiments, the first porosity is between about 65% and about 75% and the second porosity is between about 0% and about 50% or between about 5% and about 50%. Such a pore structure, in some instances, can mimic the bimodal distribution of cancellous and cortical bone, respectively. Other porosity differences between the first porosity and second porosity are also possible. Moreover, in some instances, the core component can exhibit a lower porosity than the shell component. The porosity of a polymeric component can be measured in any manner not inconsistent with the objectives of the present disclosure. In some cases, for instance, porosity is measured by determining the bulk volume of the porous sample and subtracting the volume of the polymer network material. Other methods may also be used.

Additionally, the core component and/or the shell component can exhibit any range of pore sizes not inconsistent with the objectives of the present disclosure. In some cases, for instance, the core component and/or the shell component exhibits an average pore size of about 800 nm to about 1000 µm. In some embodiments, the core component and/or the shell component exhibits an average pore size of about 1 µm to about 800 µm, about 5 µm to about 500 µm, about 10 µm to about 1000 µm, about 10 µm to about 100 µm, about 50 µm to about 500 µm, about 100 µm to about 1000 µm, about 100 µm to about 500 µm, or about 500 µm to about 1000 µm.

Moreover, it is to be understood that both the core component and the shell component of a core-shell scaffold described herein can be formed from a composition described hereinabove in Section I. Any composition described hereinabove may be used for the core and shell components of a scaffold. Thus, in some cases, the core component comprises a first polymer network formed from a polymer described hereinabove in Section I, and the shell component comprises a second polymer network formed from a polymer described hereinabove in Section I. For example, in some instances, the core component comprises a first polymer network formed from one or more monomers of Formula (A) hereinabove; one or more monomers of Formula (B1), (B2), or (B3) hereinabove; one or more monomers comprising an alkyne moiety; and one or more monomers comprising an azide moiety. The shell component of such a scaffold can comprise a second polymer network formed from one or more monomers of Formula (A); one or more monomers of Formula (B1), (B2), or (B3); one or more monomers comprising an alkyne moiety; and one or more monomers comprising an azide moiety. The polymers of the first and second polymer networks can be the same or different in chemical composition.

Similarly, in other embodiments, the first polymer network and/or the second polymer network of a scaffold described herein comprises the reaction product of an amine, an amide, or an isocyanate with the one or more monomers of Formula (A), one or more monomers of Formula (B1), (B2), or (B3), and one or more monomers comprising one or more alkyne moieties and/or azide moieties. In some cases, the first polymer network and/or the second polymer network comprises the reaction product of a polycarboxylic acid or a functional equivalent of a polycarboxylic acid with the one or more monomers of Formula (A), one or more monomers of Formula (B1), (B2), or (B3), one or more monomers comprising an alkyne moiety, and one or more monomers comprising an azide moiety. The first polymer network and/or the second polymer network of a scaffold can also comprise the reaction product of an amino acid with the one or more monomers of Formula (A), one or more monomers of Formula (B1), (B2), or (B3), one or more monomers comprising an alkyne moiety, and one or more monomers comprising an azide moiety.

In addition, in some embodiments, a polymer network of a scaffold described herein can comprise a composite polymer network, including a composite polymer network described hereinabove in Section I. For example, in some cases, a particulate inorganic material is dispersed within the first polymer network and/or the second polymer network. Any particulate inorganic material not inconsistent with the objectives of the present disclosure may be used. In some instances, for example, the particulate inorganic material comprises hydroxyapatite. Further, as described hereinabove in Section I, a particulate inorganic material may be present in a polymer network in various amounts. In some cases, for instance, a particulate inorganic material is present in the first polymer network and/or the second polymer network of a scaffold described herein in an amount up to about 70 weight percent, based on the total weight of the first polymer network and/or the second polymer network, respectively.

Further, a core-shell scaffold described herein can have various core-shell architectures. In some embodiments, for instance, the core component and the shell component are concentric cylinders. In some such cases, the diameter of the core component is about 1 percent to about 90 percent of the diameter of the shell component. Other ratios of diameters are also possible. In addition, a biphasic scaffold described herein can have other structures as well, in addition to concentric cylinder core-shell structures.

Moreover, biphasic scaffolds described herein, in some instances, can be used for the repair of segmental bone defects in vivo. For example, in some cases, a citrate-based polymer-hydroxyapatite composite of a scaffold can provide an osteoconductive surface for bone regeneration and tissue integration, while the biphasic scaffold design can mimic the hierarchical organization of cancellous and cortical bone. Specifically, such a scaffold design, in some instances, can provide both the necessary porosity in the internal (or core) phase for tissue ingrowth and also the reduced porosity in the external (or shell) phase needed to meet mechanical demands for the repair of large segmental bone defects. Therefore, such compositions, in some embodiments, can simulate both the compositional and architectural properties of native bone tissue and also provide immediate structural support for large segmental defects following implantation.

For instance, as described further hereinbelow, biphasic scaffolds described herein can be used in vivo for the repair of 10 mm segmental radius defects in rabbits. Such scaffolds can also exhibit good biocompatibility and extensive osteointegration with host bone. Further, biphasic scaffolds described herein, in some instances, significantly enhance the efficiency of new bone formation with higher bone densities in the initial stages after implantation. Compared to some other materials, biphasic scaffolds described herein can also exhibit increased flexural strength, interfacial bone ingrowth, and periosteal remodeling at early time points after implantation, such as time points prior to 15 weeks. For instance, in some cases, a scaffold described herein exhibits a compressive peak stress between about 1 MPa and about 45 MPa, between about 10 MPa and about 45 MPa, between about 20 MPa and about 45 MPa, between about 25 MPa and about 45 MPa, or between about 30 MPa and about 40 MPa, when measured as described herein. In addition, it is to be understood that the compressive strength of each portion of a scaffold can be controlled at least in part by varying the wall thickness and/or porosity of the given portion. A scaffold described herein can also exhibit an initial modulus between about 50 MPa and about 1500 MPa, between about 100 MPa and about 1500 MPa, between about 100 MPa and about 1000 MPa, between about 300 MPa and about 1500 MPa, between about 500 MPa and about 1500 MPa, between about 500 MPa and about 1000 MPa, between about 750 MPa and about 1500 MPa, or between about 750 MPa and about 1250 MPa, when measured as described herein. Moreover, a scaffold described herein can also exhibit a peak compressive strain at break between about 2% and about 5%, between about 2% and about 4%, or between about 3% and about 5%, when measured as described herein.

Thus, in another aspect, methods of treating a segmental bone defect are described herein. In some cases, such a method comprises disposing a scaffold described herein in the segmental bone defect site. Moreover, in some instances, a method of treating a segmental bone defect further comprises maintaining the scaffold at the segmental bone defect site for up to 15 weeks.

Some embodiments described herein are further illustrated in the following non-limiting examples. In the examples below, the following nomenclature will be used. "Citrate-based biodegradable elastomers" ("CABEs") can include poly(1,8-octanediol citrate) ("POC"), cross-linked urethane-doped polyester ("CUPE") elastomers, poly(alkylene maleate citrate) ("PAMC"), and biodegradable photoluminescent polymers ("BPLPs"). A "functionalized," "functional," or "clickable" CABE can refer to a CABE that has been modified to include one or more clickable moieties, such as one or more alkyne or azide moieties. "POC" refers to a polymer formed from a monomer of Formula (A) and 1,8-octanediol. A functionalized POC (or other polymer, such as BPLP) can be denoted with reference to the type of clickable moiety it contains. For example, "POC-$N_3$" refers to a POC that was formed from an additional azide-containing monomer. "POC-Al" refers to a POC that was formed from an additional alkyne-containing monomer. A mixture of differently functionalized POCs can be referred to as POC-$N_3$, Al (1/1), where the (1/1) parenthetical denotes that the mixture consists of a 1/1 weight ratio of POC-$N_3$ to POC-Al. "CUPE" refers to a polymer formed from the polycondensation of a monomer of Formula (A), a monomer of Formula (B1), (B2), or (B3), a monomer of Formula (C), and, optionally, a monomer of Formula (D1) or (D2). "PAMC" refers to a polymer formed from the polycondensation of a monomer of Formula (A), a monomer of Formula (B1), (B2), or (B3), and a monomer of Formula (D1) or (D2). "BPLP" refers to a polymer formed from the polycondensation of a monomer of Formula (A), a monomer of Formula (B1), (B2), or (B3), and a monomer of Formula (E). Further, "BPLP-Aaa" refers to a BPLP formed from an amino acid Aaa, such that "BPLP-Ser," for instance, refers to a BPLP formed from serine. A "functionalized," "functional," or "clickable" CUPE, PAMC, or BPLP refers to a polymer formed using a further monomer comprising one or more clickable moieties, such as one or more alkyne or azide moieties. Similarly, a "functionalized" or "functional" chemical species, such as a "functional diol," refers to a chemical species, such as a diol, that further comprises a clickable moiety, such as an alkyne or azide moiety. In addition, a "pre-polymer" can refer to a low molecular weight polymer or oligomer described herein.

EXAMPLE 1

Polymer Compositions

Compositions according to some embodiments described herein were prepared as follows. In general, click functional PLGA, PCL, and copolymers thereof were synthesized through a two-step process. First, a functional diol was transformed into a six-membered cyclic carbonate through reaction with ethyl chloroformate, using triethylamine (TEA) as a catalyst. Next, the functional carbonate monomers were copolymerized with lactide (LA), glycolide (GA), or epsilon-caprolactone (ε-PL) through ring-opening polymerization. FIG. 1 illustrates a reaction scheme for such a two-step synthesis of functional PLGA, PCL, and copolymers thereof.

Functionalized POC, CUPEs, PAMCs, BPLPs, and functionalized poly(glycerol sebacate) (PGS) were synthesized through a one-step co-polycondensation of multi-carboxyl monomers (such as citrate-containing monomers), functional (clickable) diols, and aliphatic diols. FIG. 2(a) depicts a scheme for synthesizing pre-polymers including alkyne groups or azide groups. FIG. 2(b) illustrates a scheme for forming a cross-linked elastomer from the pre-polymers. By introducing azide and alkyne functional diols, azide (pre-POC-$N_3$) and alkyne (pre-POC-Al) functional POC pre-polymers can be synthesized, as shown in FIG. 2(a). POC-$N_3$ and POC-Al pre-polymers can be mixed together and cross-linked through a copper catalyzed azide-alkyne cycloaddition (CuAAC) process, or heated to induce a copper-free thermal cross-linking process. In the thermal cross-linking process, a thermal click reaction between azide and alkyne groups occurs. In addition, esterification between pendant —COOH and —OH groups from POC-$N_3$ and POC-Al pre-polymer chains can also take place simultaneously to form thermal synchronous binary (TSB) cross-linked (esterification and thermal click reaction) POC-click elastomers via a one-step post-polymerization process, as shown in FIG. 2(b).

Further, the residual azide groups on the surface of the cross-linked POC-click polymer can enable a convenient route for biomolecule conjugation by another copper-free click reaction, strain-promoted alkyne-azide cycloaddition (SPAAC). Collagen mimetic peptide p15, which can effectively promote the adhesion and proliferation of endothelial cells (ECs), can be conjugated to POC-click elastomeric films and scaffolds through SPAAC (FIG. 2(b)).

As described above, functional POC pre-polymers with azide (pre-POC-$N_3$) or alkyne (pre-POC-Al) groups can be synthesized by co-polycondensation of citric acid (CA), 1,8-octanediol (OD), and azide or alkyne functional diols (diazido-diol [DAzD] or alkyne-diol [AlD] in FIG. 2(a)). The successful introduction of azide or alkyne groups into the pre-polymers can be shown by Fourier transform infrared (FTIR) and nuclear magnetic resonance (NMR) spectroscopy, as indicated by the appearance of the characteristic IR absorption peak of the azide group (2100 cm$^{-1}$ in FTIR) or the $^1$H-NMR peak of the protons on the —$CH_2$— group next to the alkyne groups (around 4.5 ppm in $^1$H-NMR). The intensities of both peaks can be enhanced with increased functional diol to OD monomer feed ratios. For nomenclature purposes, the feed ratio can be denoted as follows: POC-$N_3$-x or POC-Al-x (x=1, 2, or 3), where "x" represents the ratio of DAzD or AlD to OD. Specifically, for a given value of x, the ratio of DAzD or AlD to OD is x/10.

Figure 3:
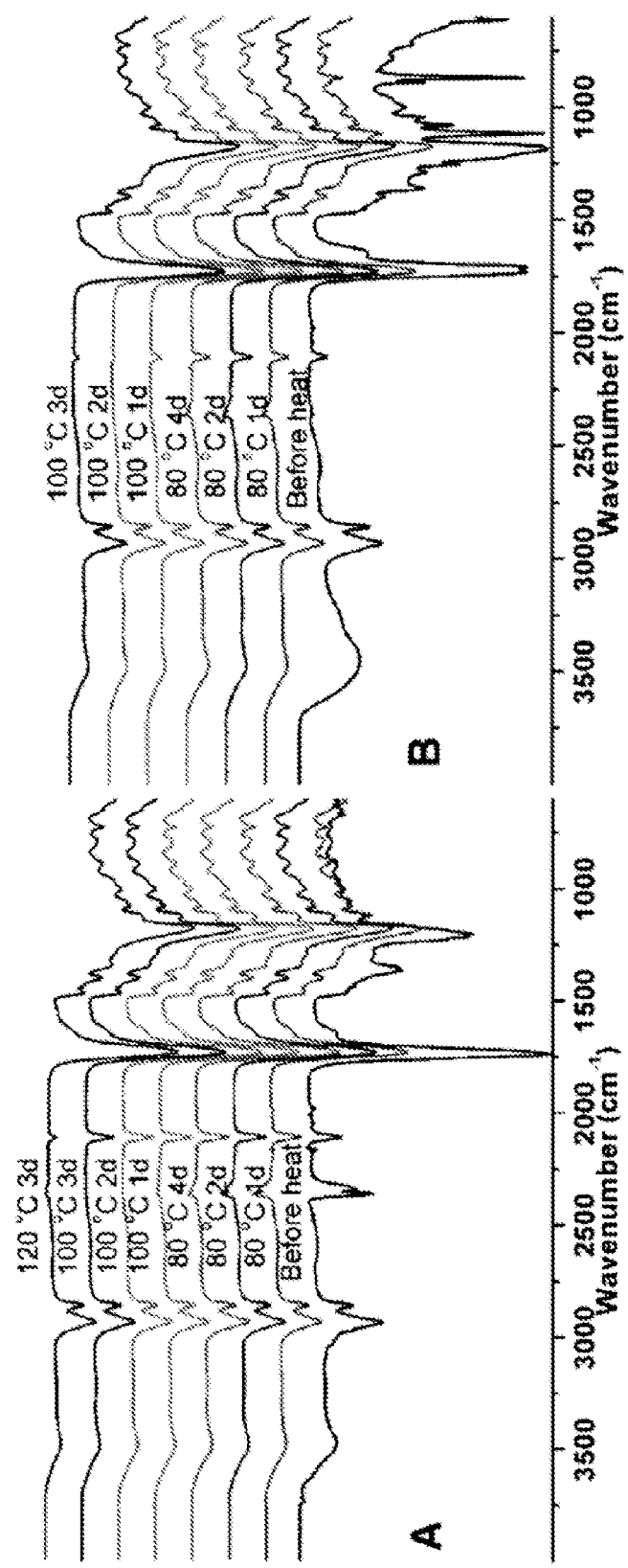
FIGS. 3(a)-3(d) illustrate chemical and physical properties of compositions according to some embodiments described herein.
Figure 3:
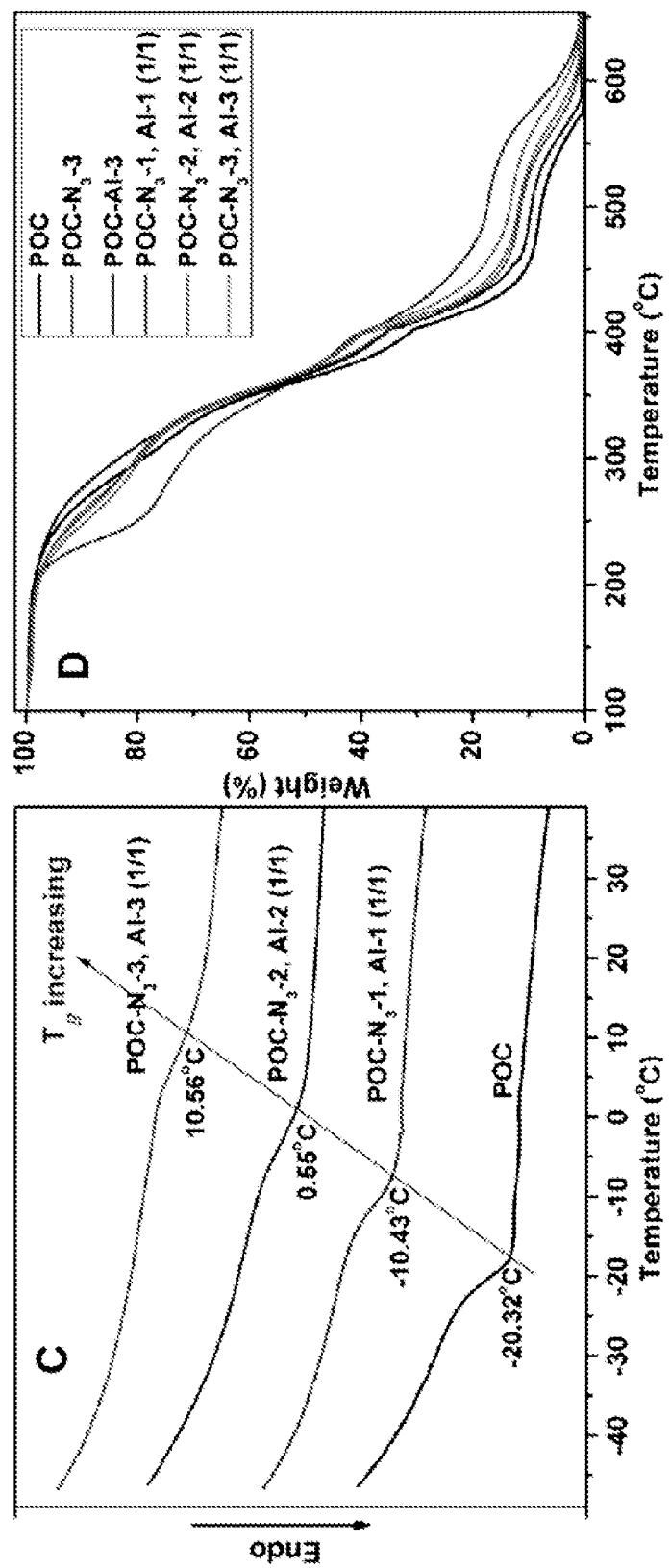

The thermal stability of azide groups was evaluated by heating POC-$N_3$-1 (molar ratio of CA:OD:DAzD was 1:1: 0.1) pre-polymers at 80, 100 or 120° C. for different time periods. The FTIR spectra of the obtained POC-$N_3$-1 films are shown in FIG. 3(a). It can be seen that the characteristic infrared absorption peak of the azide group at 2100 cm$^{-1}$ remain unchanged after heating at 80 or 100° C. for 1, 2, or even 3 days, but decreased after heating at 120° C. for 3 days, indicating that azide group may maintain its stability and reactivity at 80 and 100° C. In another study, an equal-weight blend of POC-$N_3$-1 and POC-Al-1 pre-polymers was heated at either 80 or 100° C. for different durations. From the FTIR spectra of the POC-click films, as shown in FIG. 3(b), the intensity of the azide absorption peak at 2100 cm$^{-1}$ remained unchanged after heating at 80° C. for up to 4 days, but decreased quickly after heating at 100° C. for 1, 2, or 3 days, suggesting that 100° C. is a suitable temperature for the thermal click reaction.

Figure 4:
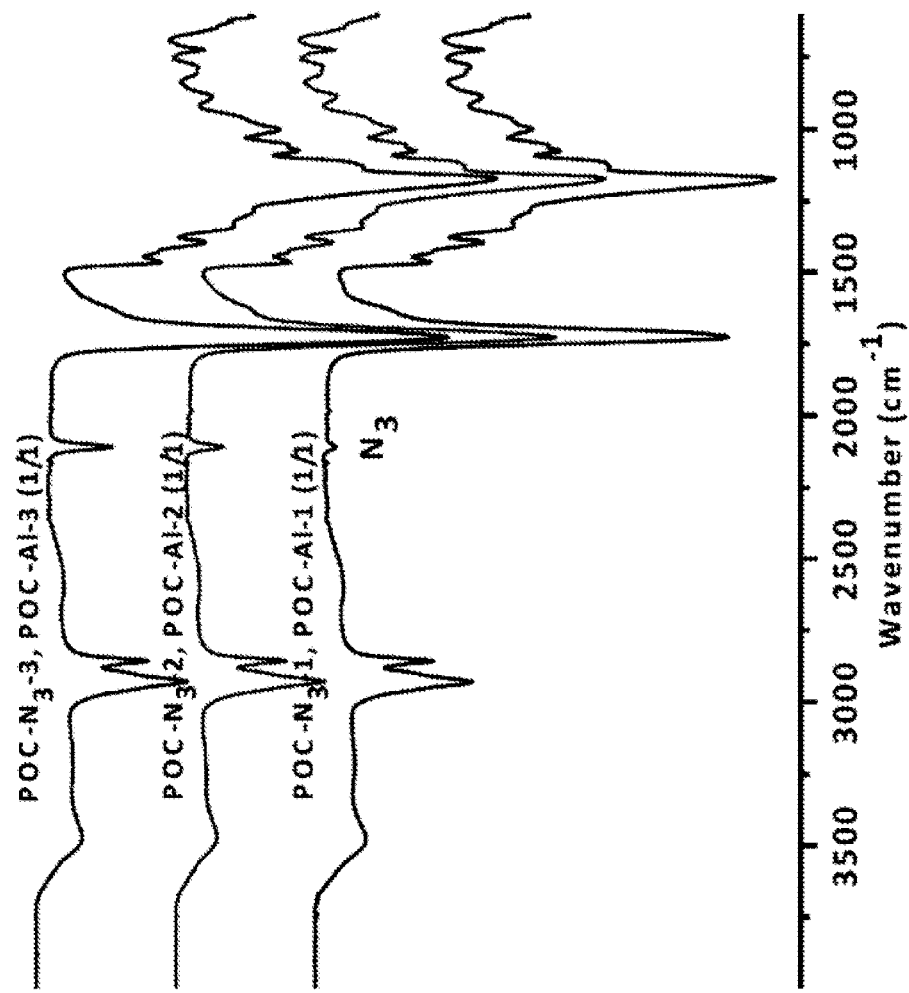
FIG. 4 illustrates absorption spectra of compositions according to some embodiments described herein.

The cross-linking density of polymers and polymer networks described herein could also be controlled by varying cross-linking times and the clickable pre-polymer ratios (pre-POC-$N_3$-x/pre-POC-Al-y (x, y=1, 2 or 3)). In some instances, some azide groups were preserved after completion of click cross-linking (FIG. 4) for further bioconjugation because each DAzD molecule contains two azide groups, while each AlD molecule contains only one alkyne group (FIG. 2(a)).

The thermal properties of POC film (100° C., 3d) and a series of POC-click films (100° C., 3 d, FIG. 3(b)) made by heating the equal-weight mixtures of POC-$N_3$-x and POC-Al-x pre-polymers (x=1, 2, or 3) were also characterized by differential scanning calorimetry (DSC) and thermal gravimetric analysis (TGA). DSC curves in FIG. 3(c) indicated apparent glass transition temperatures ($T_g$) for all polymers. Increasing the amount of click moieties in the cross-linked polymer film resulted in the rapid increase of $T_g$, possibly due to the formation of rigid triazole rings by the thermal click reactions. TGA curves (FIG. 3(d)) showed that all polymers were relatively stable, with thermal decomposition temperatures ($T_d$) higher than 218° C. POC showed a $T_d$ of 241.6° C. POC-Al-3 homopolymer had the highest $T_d$, POC-$N_3$-3 homopolymer had the lowest $T_d$, and the $T_d$ values of the POC-click polymers were in between.

Figure 5:
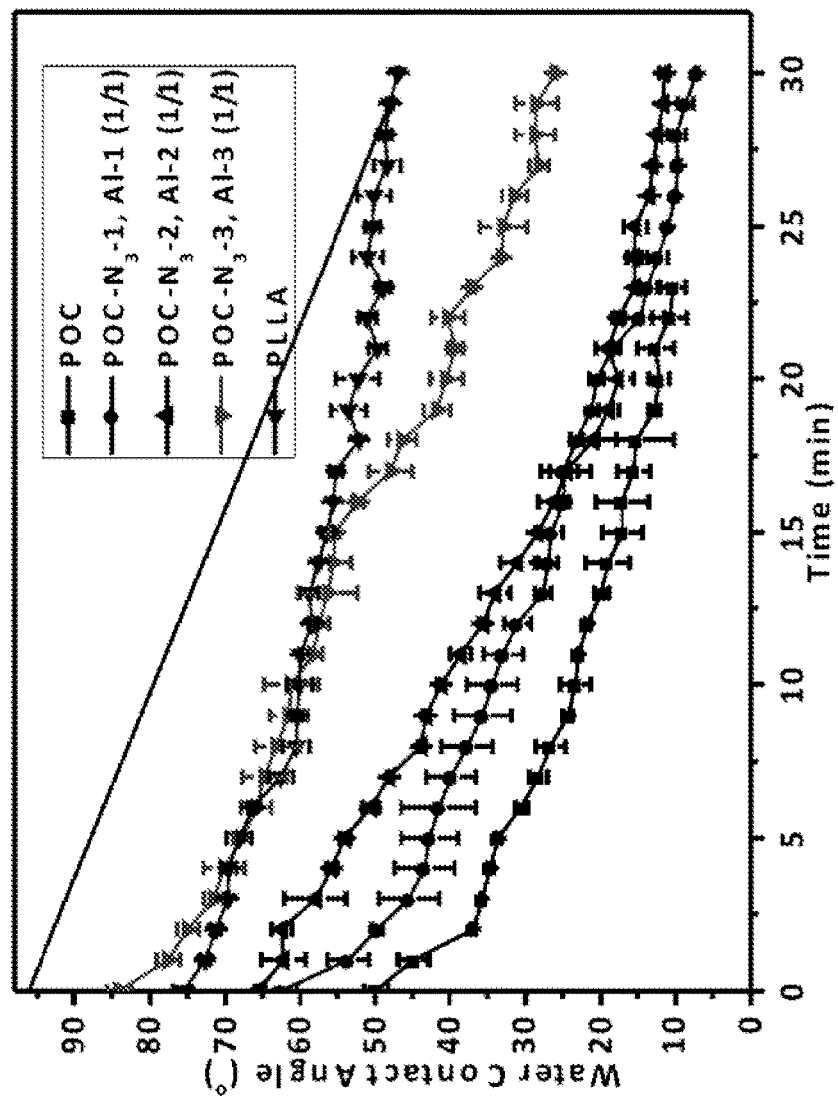
FIG. 5 illustrates water contact angles of compositions according to some embodiments described herein.

The wettability of the series of POC-click polymers was assessed by water-in-air contact angle tests using POC and PLLA as controls. The results are shown in FIG. 5. POC-click1 and POC-click2 showed similar wettability as POC, especially after 30 minutes of water contact. Although the contact angle of POC-click3 was even larger than that of PLLA initially, it became much lower than that of PLLA after 30 minutes, evidence of the hydrophilic nature of the POC backbones.

Figure 8:
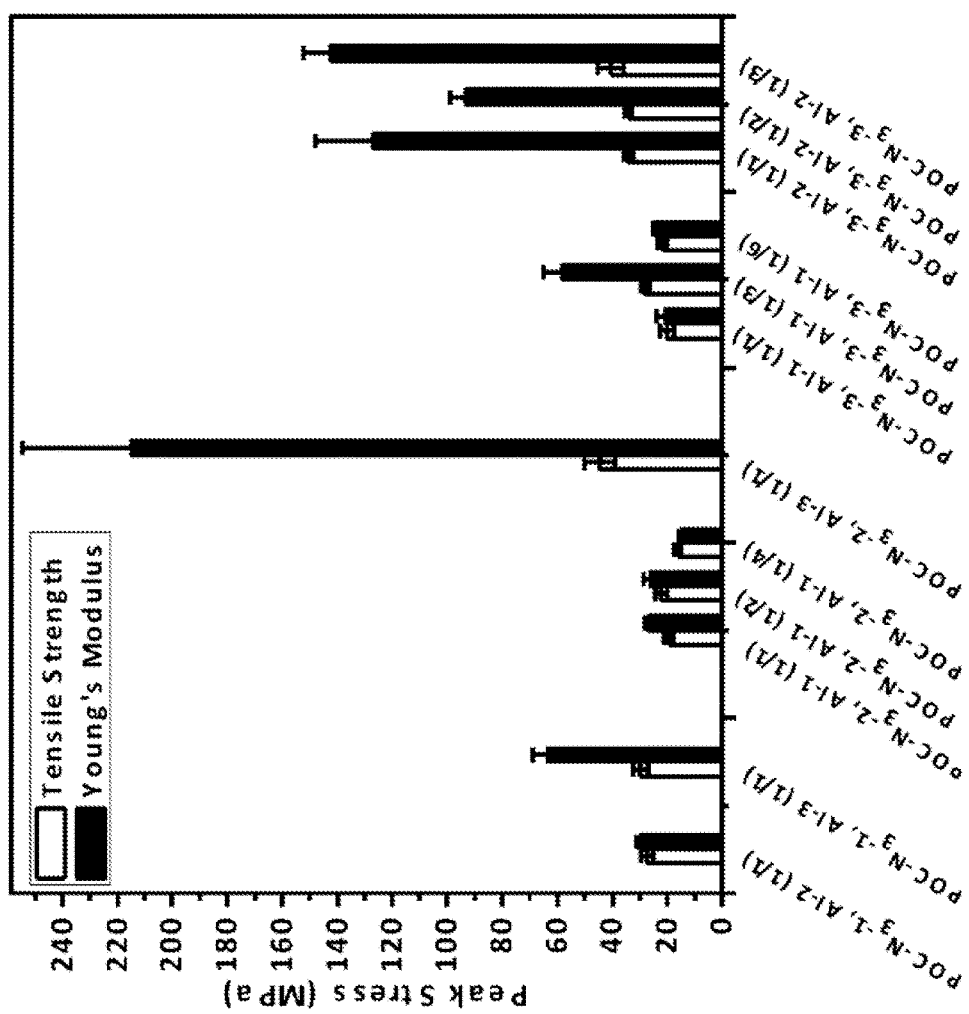
FIG. 8 illustrates plots of mechanical properties of compositions according to some embodiments described herein.

Mechanical properties of the POC and POC-click polymers are shown in FIGS. 6(a)-6(h). The tensile stresses of both POC-$N_3$-x, Al-x (1/1) and POC-$N_3$-x, Al-x (1/2) (x=1, 2, or 3) polymer films were 10-40 MPa higher than that of POC (5 MPa), and 10-20 MPa higher than that of corresponding POC-$N_3$-x and POC-Al-x homopolymer films (FIG. 6(a)). FIG. 7 provides a summary of the cross-linking density (N) and some mechanical properties of various polymers. All cross-linked films were obtained by heating at 100° C. for 3 days. Mechanical properties for other compositions are illustrated in FIG. 8. Specifically, FIG. 8 provides properties for POC-click TSB cross-linked polymers made from mixtures of POC-$N_3$-x and POC-Al-y (x, y=1, 2 or 3 and x≠y) with different weight ratios. The elongations of the films are around 200-300% except for that of POC-$N_3$-3, Al-3 (1/1) and POC-$N_3$-3, Al-3 (1/2), which are all lower than 100%, with an overall inverse correlation to cross-link density (FIG. 6(c) and FIG. 7). POC-$N_3$-1, Al-1 (1/1), and POC-$N_3$-2, Al-2 (1/1) all showed elastomeric properties similar to POC (FIG. 6(d)). Although the stress-strain curve of POC-$N_3$-3, Al-3 (1/1) had a yield point (FIG. 6(d)) that is characteristic of plastic polymers, after immersing the material in PBS for about 24 h, the same polymer showed elastomeric characteristics (FIG. 6(e)), indicating that POC-N3-3, Al-3 (1/1) can still serve as an elastomeric graft in vivo (wet conditions). POC-click wet mechanical strength was even better than that of CUPE. When the cross-linking time was increased from 0.5 day to 3 days, the tensile stresses and Young's modulus of POC-click polymers showed a continuous increase, especially for POC-$N_3$-

Figure 6:
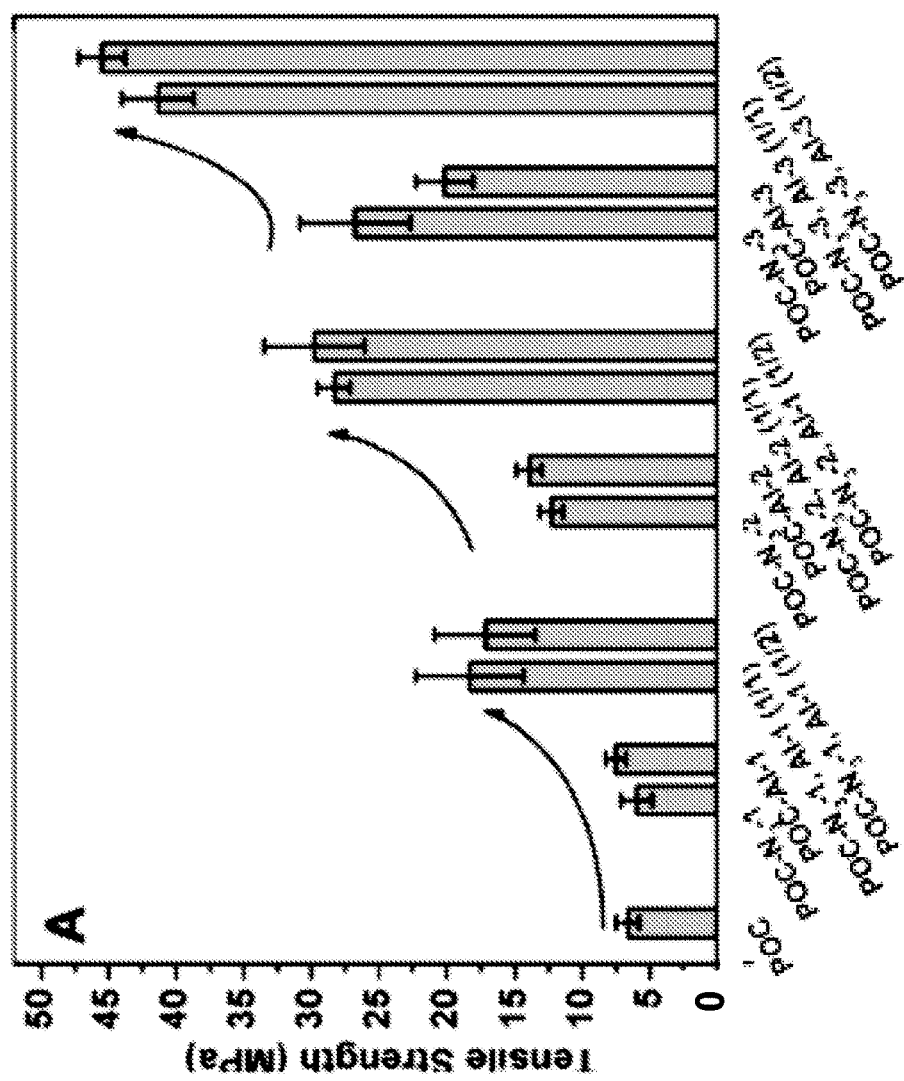
FIGS. 6(a)-6(h) illustrate various mechanical properties of compositions according to some embodiments described herein.
Figure 6:
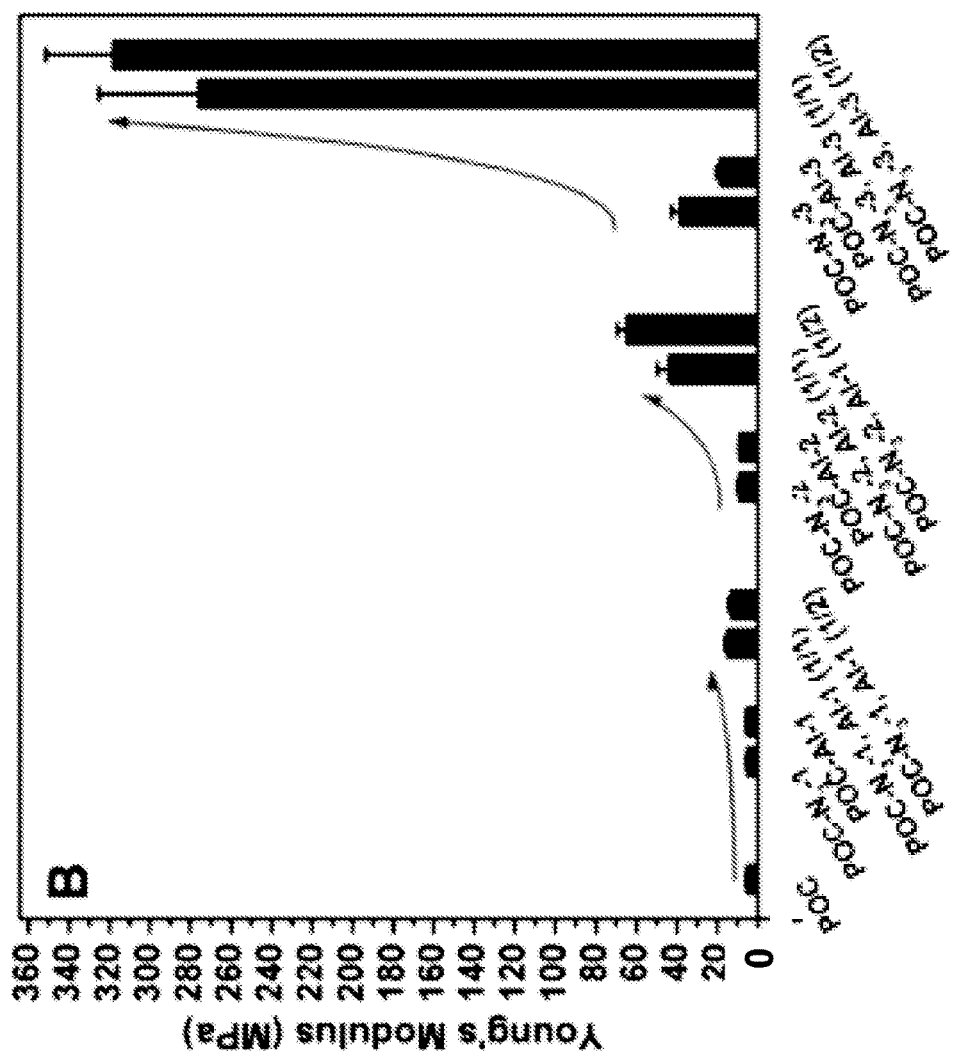
Figure 6:
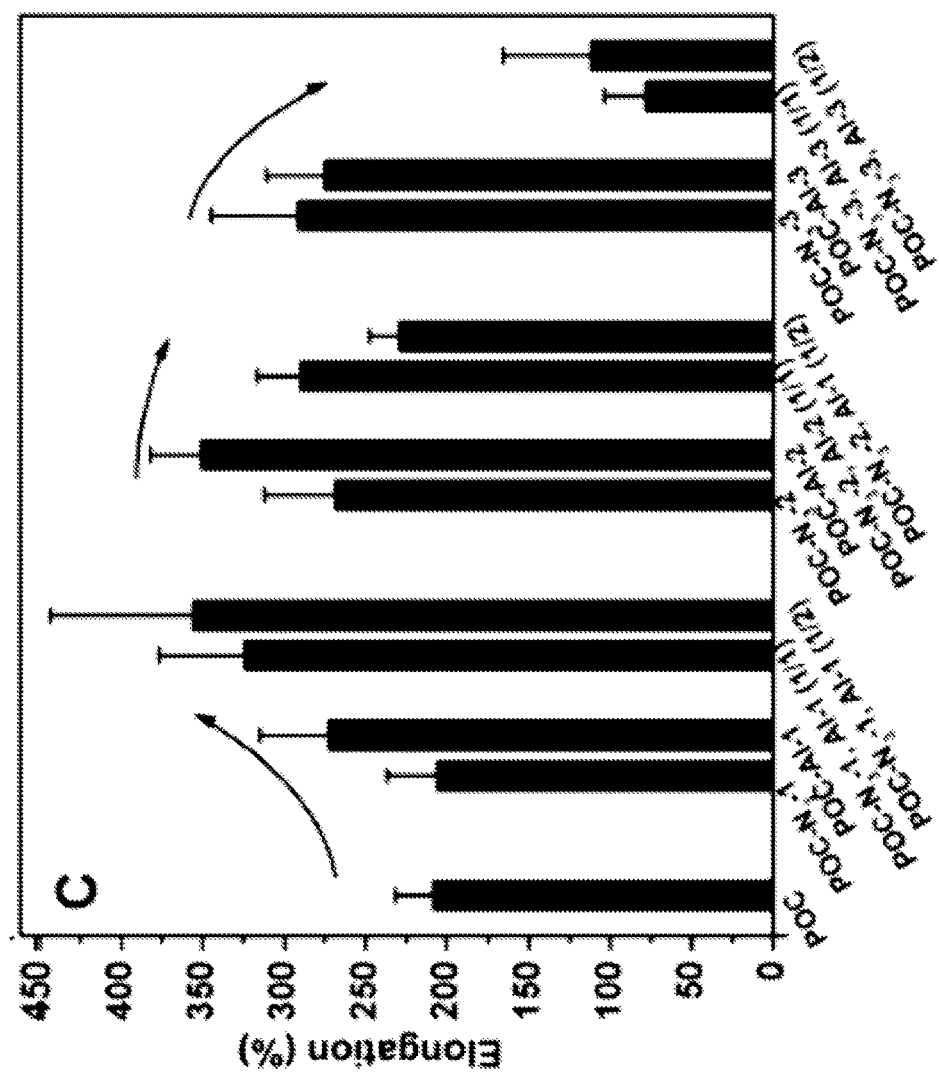
Figure 6:
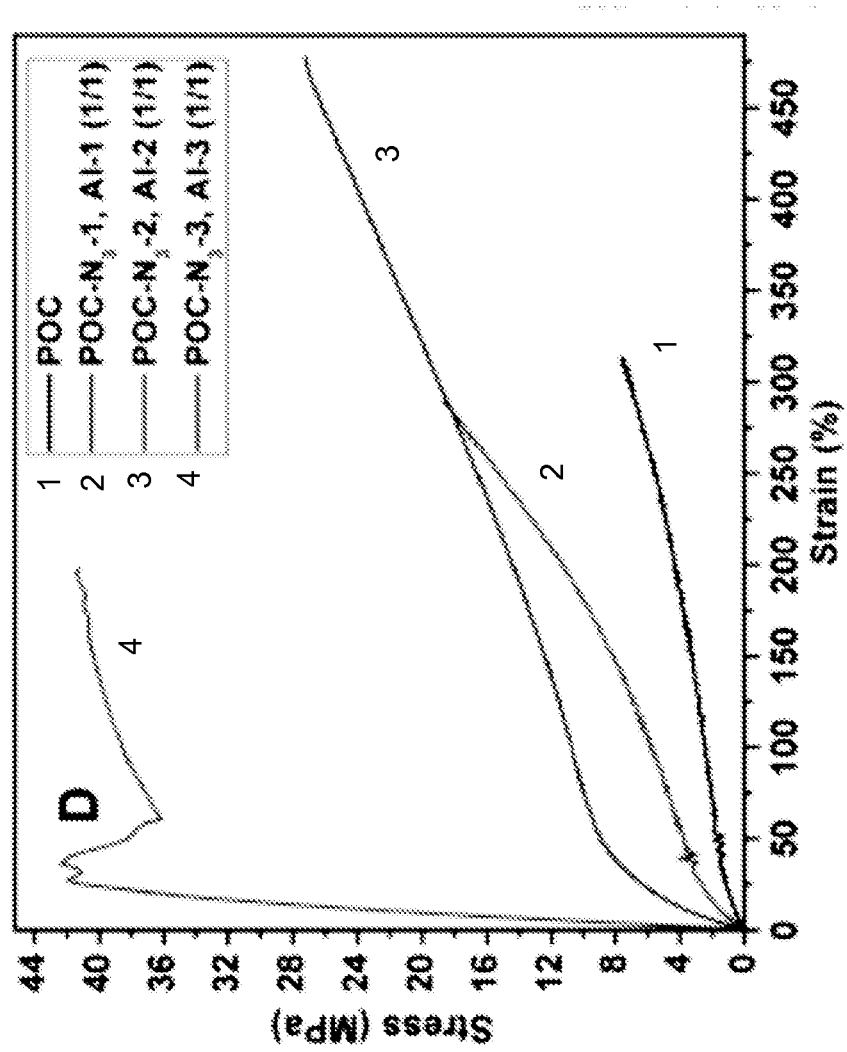
Figure 6:
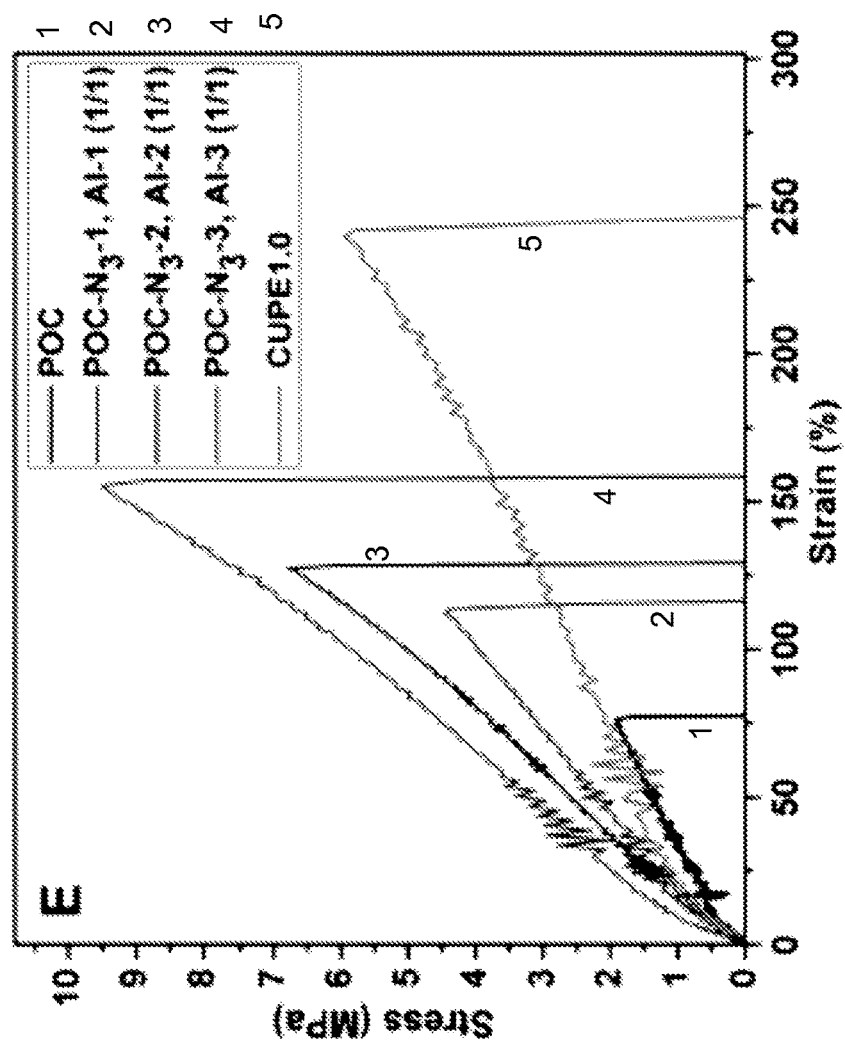
Figure 6:
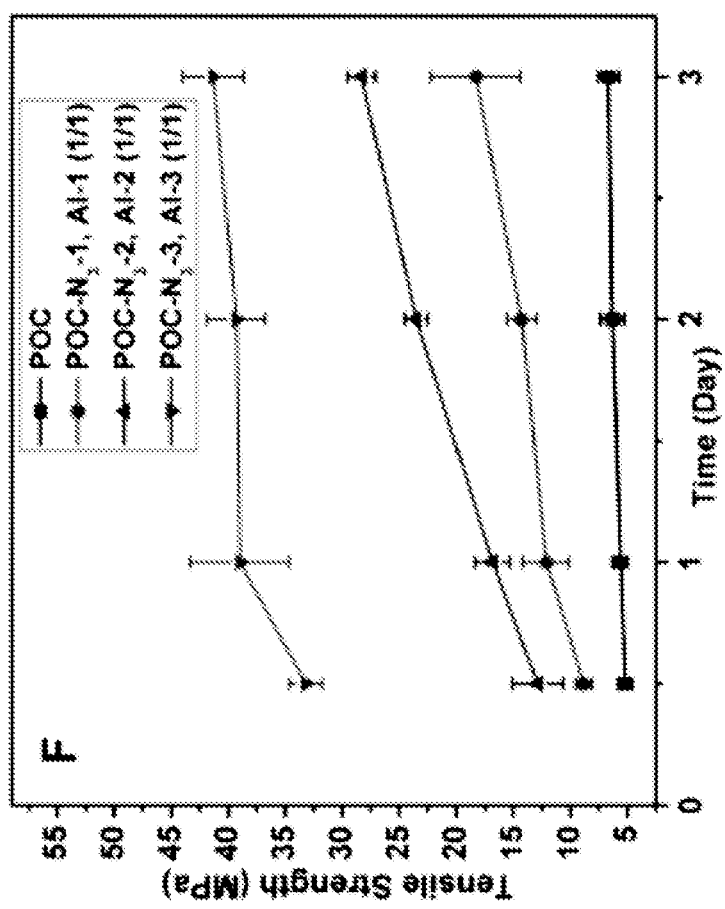
Figure 6:
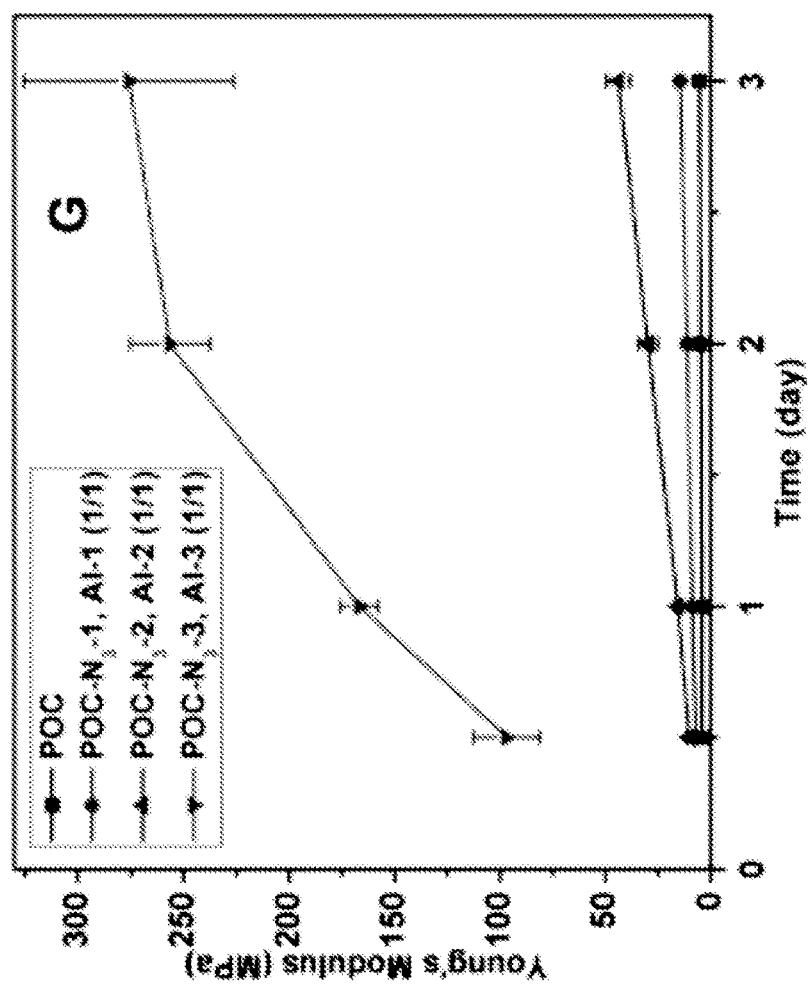
Figure 6:
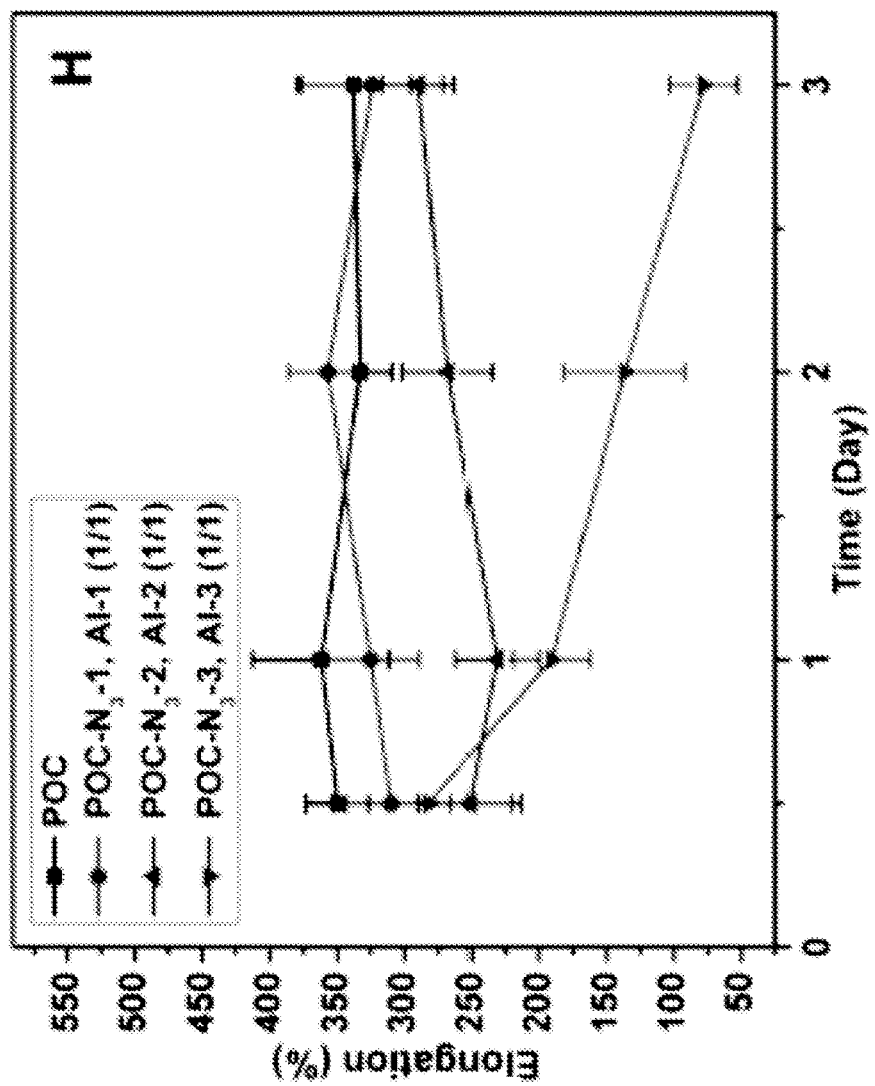
Figure 9:
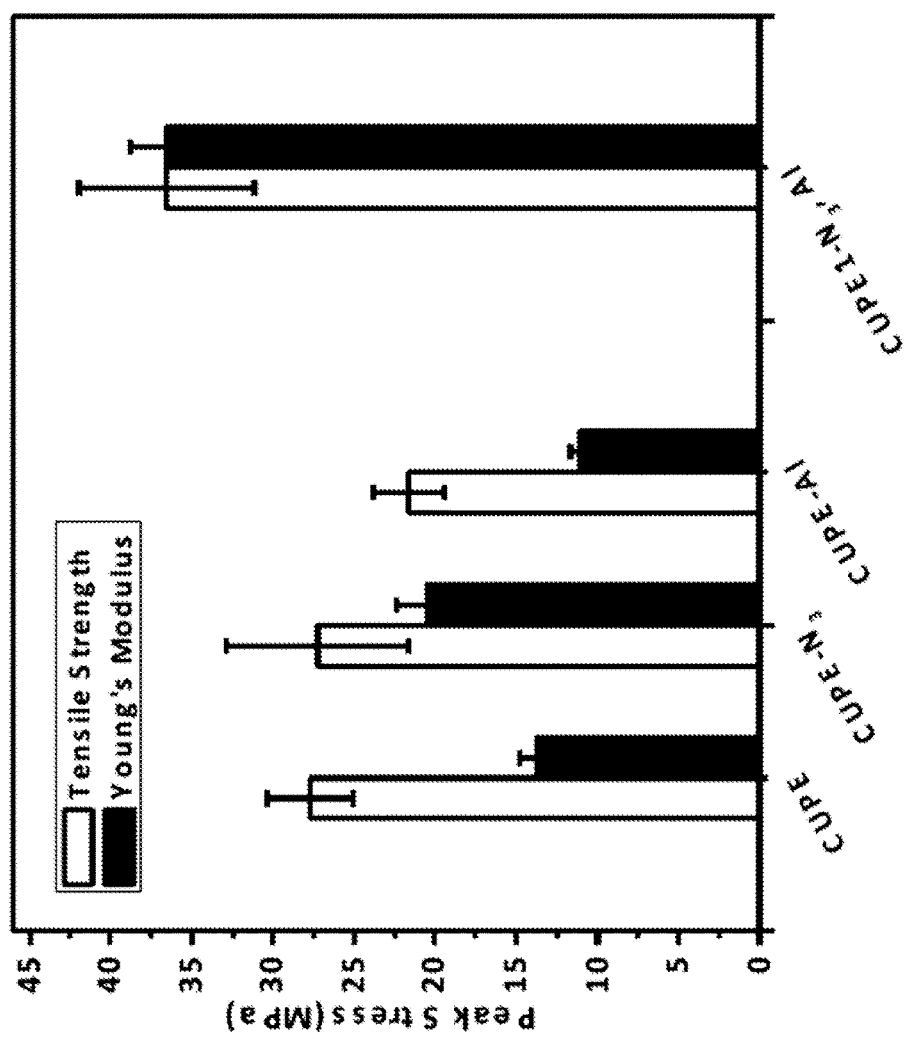
FIG. 9 illustrates plots of mechanical properties of compositions according to some embodiments described herein.

1, Al-1 (1/1) and POC-N$_3$-2, Al-2 (1/1), while POC only showed very limited improvement during this time period (FIGS. 6(*f*) and 6(*g*)). The elongation of the polymer films showed no significant change when the cross-linking time was varied (FIG. 6(*h*)), except in the case of POC-N$_3$-3, Al-3 (1/1). The above investigation suggested that that the introduction of the click reaction could significantly improve mechanical strength of the TSB cross-linked POC-click polymer. The versatility of this method is further evidenced by the enhanced mechanical strength of cross-linked CUPE after the introduction of a thermal click reaction to form CUPE-click polymer films (FIG. 9).

Figure 10:
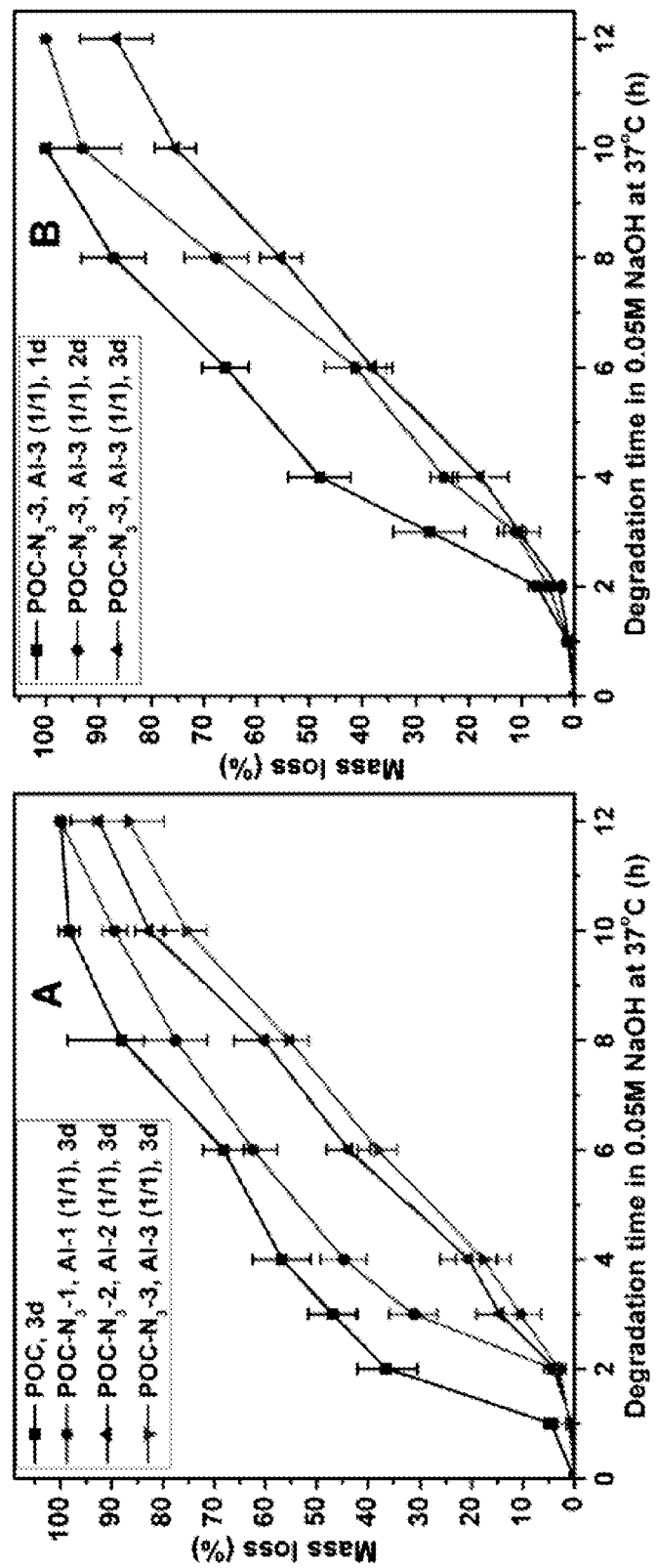
FIGS. 10(a)-10(d) illustrate plots of degradation properties of compositions according to some embodiments described herein.
Figure 10:
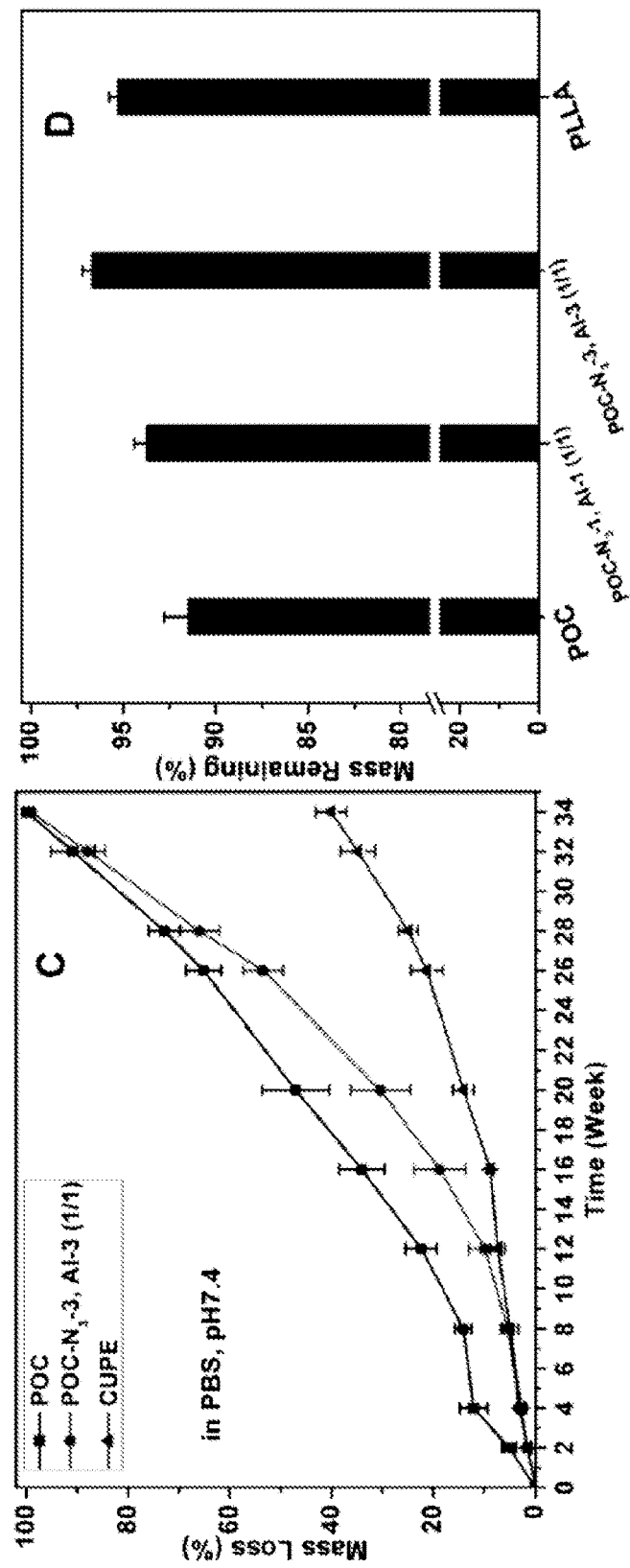
Figure 11:
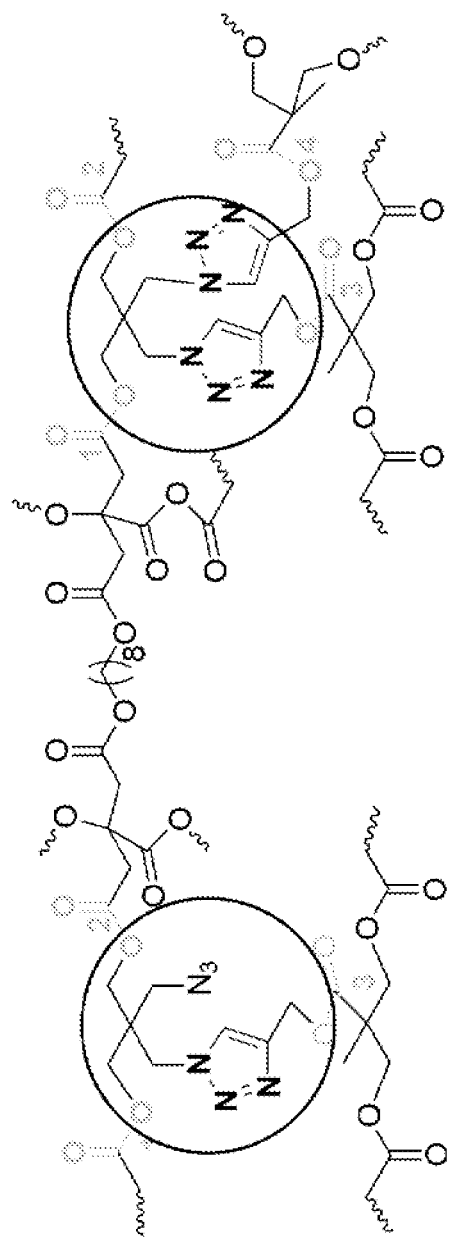
FIG. 11 illustrates the structure of a component of a composition according to one embodiment described herein.

The in vitro and in vivo degradation behaviors of different polymers are shown in FIGS. 10(*a*) and 10(*b*). POC-click polymers degraded more slowly than POC in 0.05M NaOH solution with 100% degradation of POC and POC-click1, but only around 80% degradation of POC-click3 after 12 hrs incubation. The degradation rates decreased as the cross-link density increased (FIG. 10(*a*)). A similar trend was found with the increase of cross-linking time from 1 day to 3 days (FIG. 10(*b*)). The degradation curves of POC-click3, POC, and CUPE in PBS (pH 7.4) are shown in FIG. 10(*c*). During the first 12 weeks, POC-click3 demonstrated a mass loss of no more than 5%, while POC lost around 25% of its initial mass. After the 12th week, POC-click3 entered into a relatively rapid degradation period, and the mass loss of the polymers caught up with that of POC at the 32nd week. POC-click3 and POC were completely degraded at 34 weeks, while no more than 40% of CUPE was degraded. Not intending to be bound by theory, it is believed that the "first slow, then fast" degradation phenomenon of POC-click3 can be explained in terms of its chemical structure (FIG. 11). Both ester bonds and triazole rings existed in the TSB cross-linked POC-click3 films, and ester bonds degraded much faster than triazole rings. Initially, POC-click3 degraded much slower than POC due to the existence of trizole rings in the POC-click 3 network. Once all the ester bonds surrounding DAzD (in the circle in FIG. 11) hydrolyzed, the DAzD cross-link points were totally destroyed. Along with the destruction of the DAzD cross-link points, the degradation rate of POC-click3 became even faster than that of POC, allowing the mass loss of POC-click3 to catch up with that of POC finally. These degradation properties of POC-click polymers are favorable for many biomedical applications, such as tissue engineering, due to the good preservation of mechanical strength in the initial period after implantation before the tissues are regenerated.

After 20 weeks subcutaneous implantation in the back of Sprague Dawley (SD) rats, the mass loss of POC-click1, POC-click3, POC, and PLLA were 6.28%, 3.28%, 9.54% and 5.71% respectively (FIG. 10(*d*)).

Figure 12:
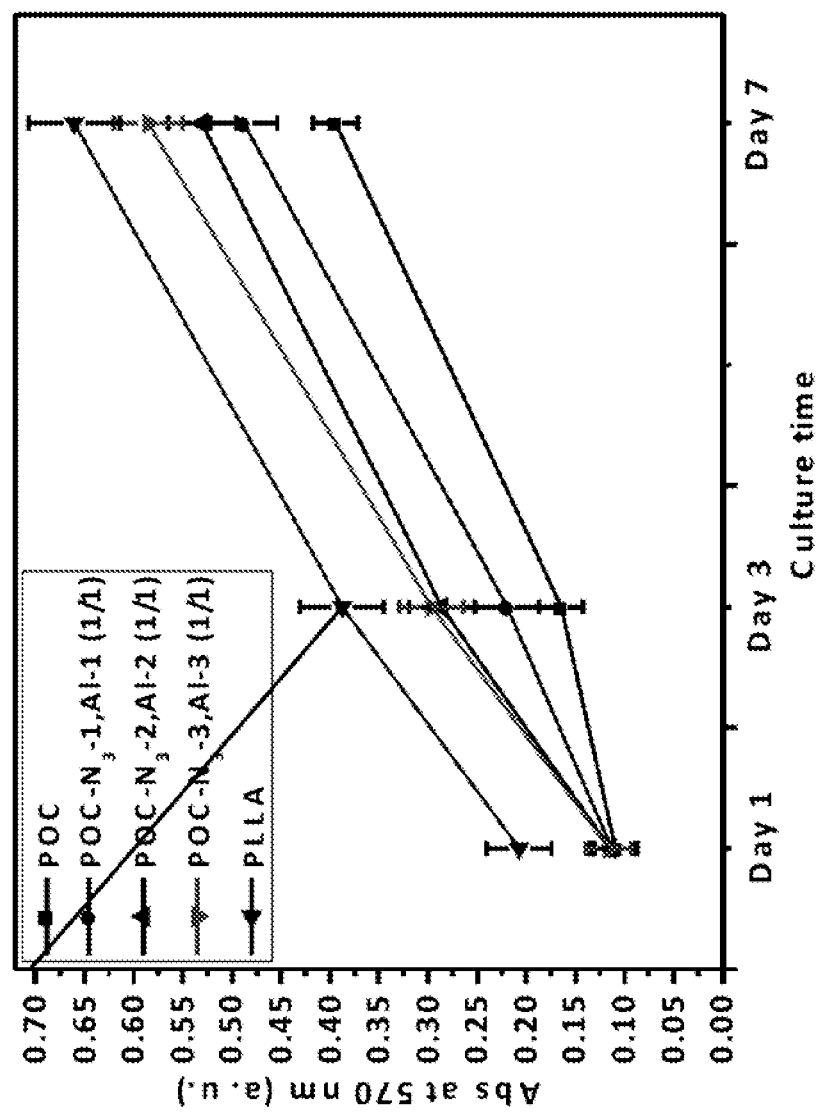
FIG. 12 illustrates plots of biological properties of compositions according to some embodiments described herein.

The cytocompatibility of POC-click polymers was assessed by a methyl tetrazolium (MTT) assay against 3T3 fibroblast cells. POC and PLLA were used as controls. The MTT results are shown in FIG. 12. Although cells did not proliferate on POC-click polymers and POC as well as on PLLA, they did display a similar growth pattern. The proliferation of 3T3 cells on POC-click polymers was also found to be better than that on POC. The MTT result suggested that the introduction of click moieties into polyester elastomers does not reduce the cytocompatibility of the so-obtained polymers.

Figure 13:
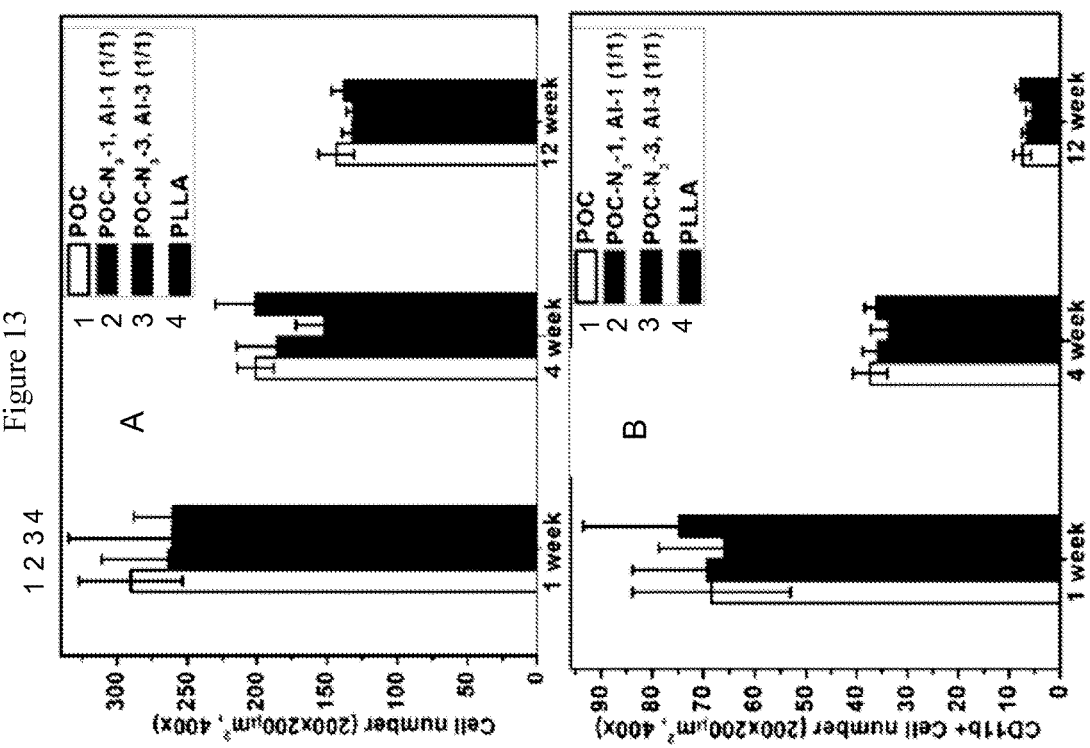
FIGS. 13(a) and 13(b) illustrate plots of biological properties of compositions according to some embodiments described herein.

Foreign body response was assessed by a subcutaneous implantation of POC-click1 and POC-click3 films in SD rats with POC and PLLA as controls. All samples implanted for one week produced a slight acute inflammatory response, a general process that is expected and consistent with the introduction of a foreign material into the body, which can be confirmed by the appearance of leukocytes and macrophages (H & E staining) as well as CD11b positive cells (CD11b staining) in the tissues surrounding the polymer films. The cell-count results are shown in FIGS. 13(*a*) and 13(*b*). Few macrophages and CD11b positive cells in the surrounding tissues could still be observed after 4 weeks of implantation, but the cell numbers were much lower than after one week of implantation. After 12 weeks of implantation, most of the cells surrounding the samples were fibroblast cells, and the cell density decreased as well. CD11b positive cells were rarely seen after 12 weeks, indicating that no chronic inflammatory reaction took place. The mild inflammatory response suggested that POC-click polymers and their degradation products were as cytocompatible as POC and PLLA, further indicating that the introduction of click moieties does not compromise the biocompatibility of the so-obtained polymers.

Figure 2:
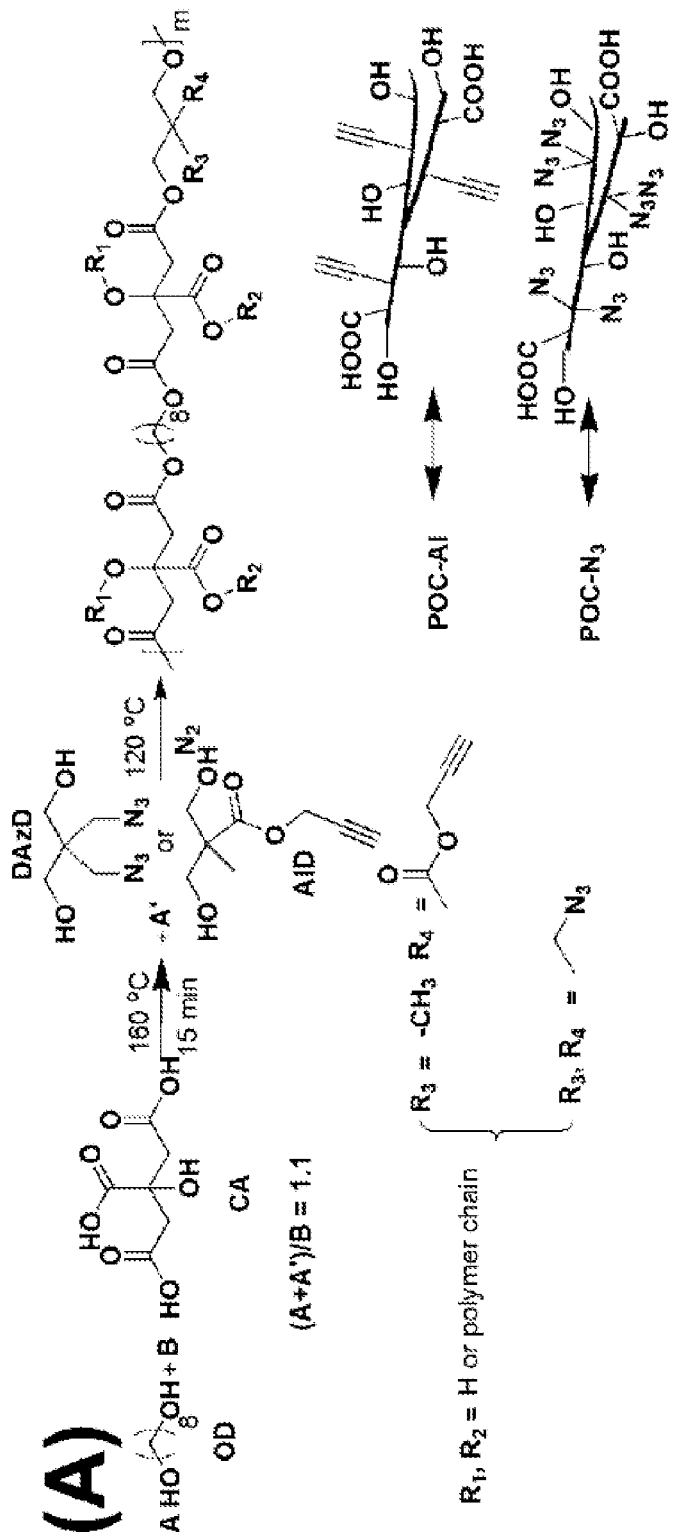
FIGS. 2(a) and 2(b) illustrate reaction schemes for making compositions according to some embodiments described herein.
Figure 2:
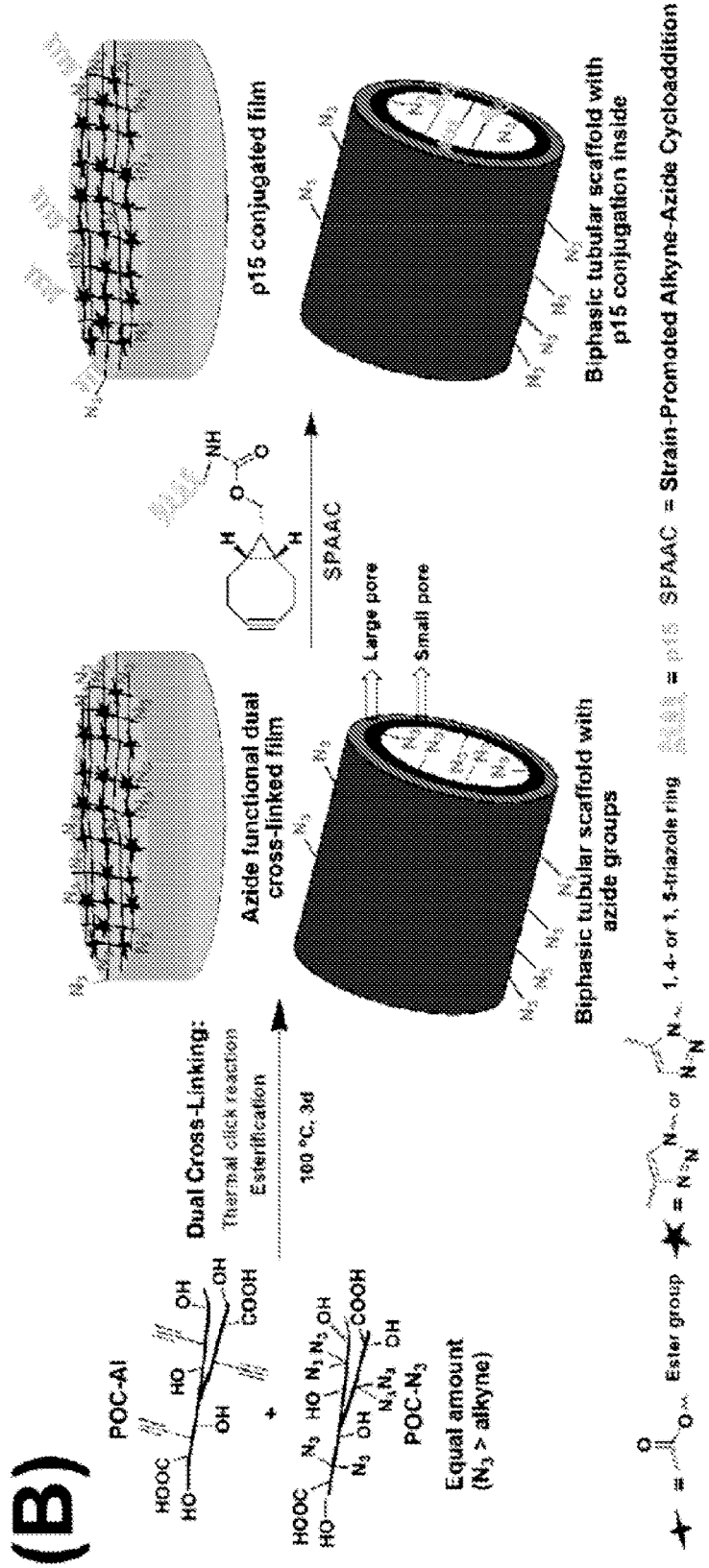
Figure 14:
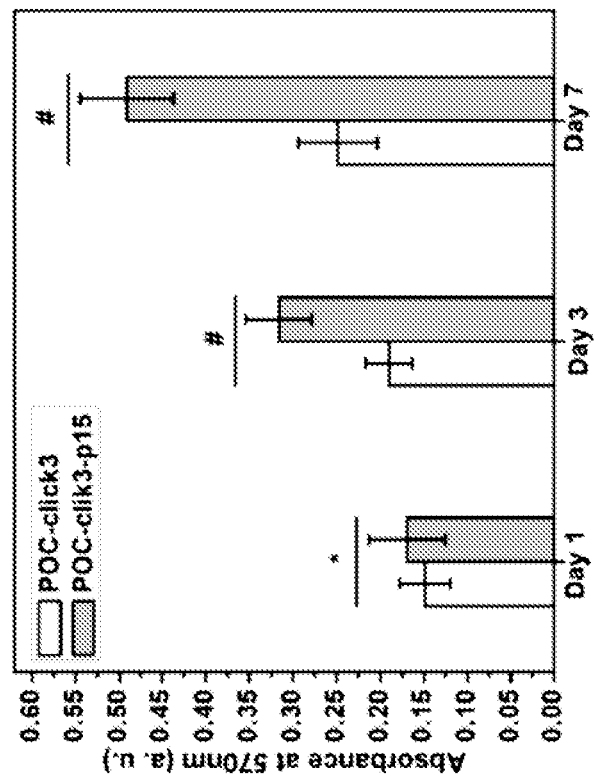
FIG. 14 illustrates plots of biological properties of compositions according to some embodiments described herein.
Figure 15:
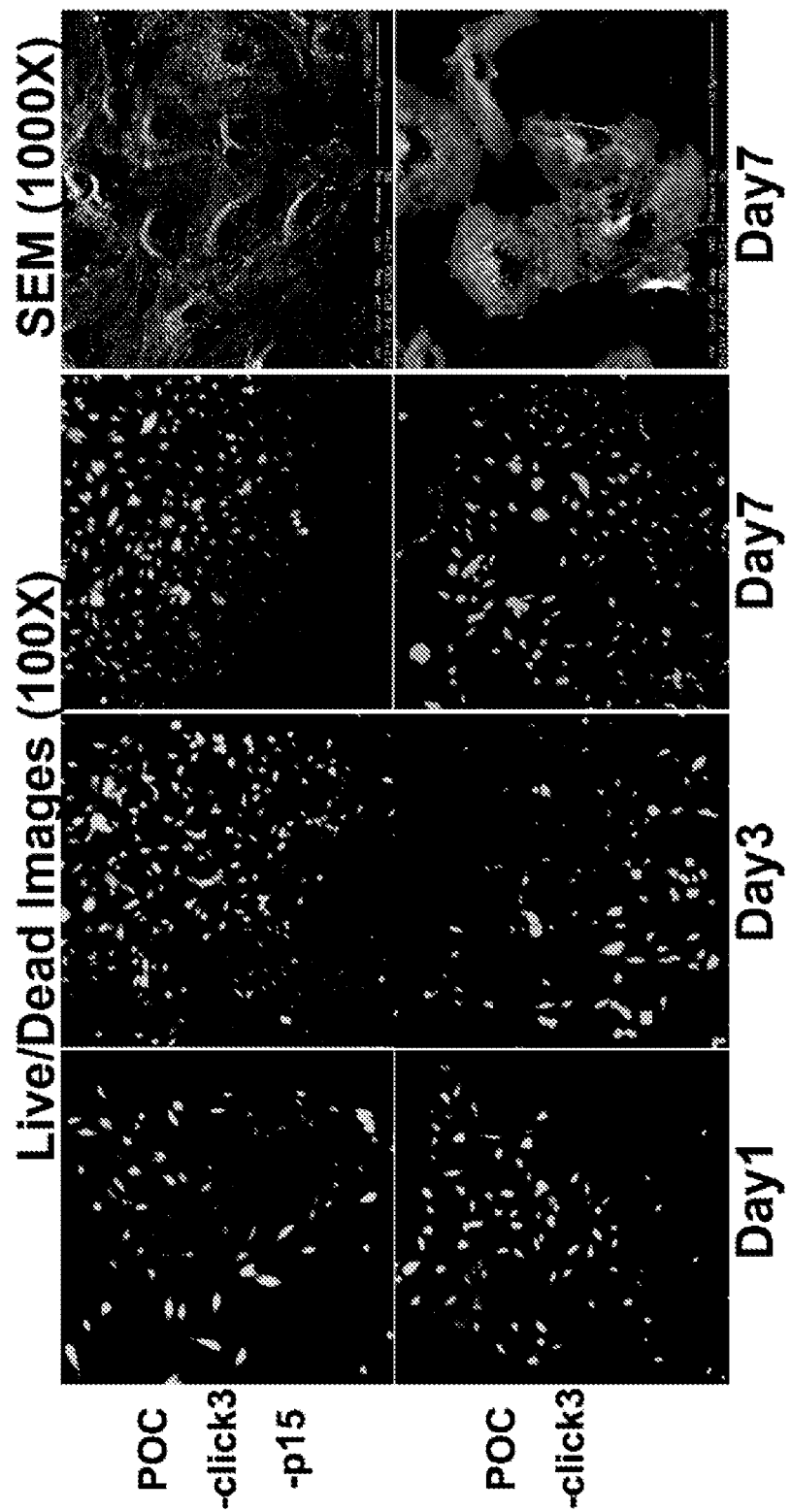
FIG. 15 illustrates microscopy images of compositions according to some embodiments described herein.

As described above, the residual azide groups on POC-click polymers provided convenient conjugation of bioactive molecules to the surface of POC-click films or scaffolds via a second copper-free click reaction, SPAAC (FIG. 2(*b*)). As one example, collagen mimetic peptide p15 was conjugated onto the surface of POC-click3 film by SPAAC, and the viability/proliferation of human umbilical vein endothelial cells (HUVEC) on POC-click3-p15 films were also investigated. The successful conjugation of p15 onto the surface of POC-click3 film was confirmed negatively by the decrease of the azide absorption peak (2100 cm$^{-1}$) after p15 conjugation in the FTIR spectra of the films, and positively by the appearance of the characteristic peak of guanidine group in the UV-vis curves of the films after the Sakaguchi reaction (for quantification, each p15 molecule contains one guanidine group). The effect of p15 conjugation on HUVEC proliferation properties was investigated by MTT assay, Live/Dead assay and SEM, using untreated POC-click3 films as control. The results are shown in FIG. 14 and FIG. 15. From the MTT result (FIG. 14), it could be seen that with the same seeding density (5000 cells/well), the initial HUVEC cell number (day 1) on p15 conjugated POC-click3 (POC-click3-p15) films was higher than that on untreated POC-click3 films. After the initial cell adhesion, the HUVEC proliferation rate on POC-click3-p15 films was obviously faster than that on untreated POC-click3 films. The HUVEC cell density on POC-click3-p15 films at day 7 was nearly doubled compared to the data of POC-click3 films. The Live/Dead images (FIG. 15) show the same growth tendency. Both Live/Dead assay images and SEM images (FIG. 15) showed the characteristic cobblestone morphology of live cells. Few dead cells were found in the Live/Dead images. The number of dead HUVEC cells on POC-click3-p15 films was less than that on POC-click3 films (FIG. 14). The HUVEC cell proliferation results showed that the p15 conjugation on POC-click3 surfaces could promote HUVEC cell adhesion and proliferation.

To further evaluate the POC-click polymers for tissue engineering, especially for tissue engineering vascular graft (TEVG) applications, POC-click3 was chosen as a representative to be molded into a tubular triphasic scaffold (TTS). The mechanical properties of the scaffold were tested and compared with TTS's formed from POC and CUPE. Furthermore, the conjugation of p15 onto the inner surface of POC-click3 TTS was also carried out.

The TTS was composed of a rough inner lumen surface, a middle layer of porous scaffold material with a pore size of 1-20 μm, and an outer layer of porous scaffold with a pore size of 150-250 μm. This design corresponded to the microstructure of native vessels. A rough surface is more favorable for the growth of endothelial cells, and a pore size of 1-20 μm is preferable for the compartmentalization of endothelial cells and smooth muscle cells simulating the elastic lamina in native vessels. A pore size of 150-250 μm is suitable for the growth of fibroblasts and the formation of extracellular matrix (ECM).

Figure 16:
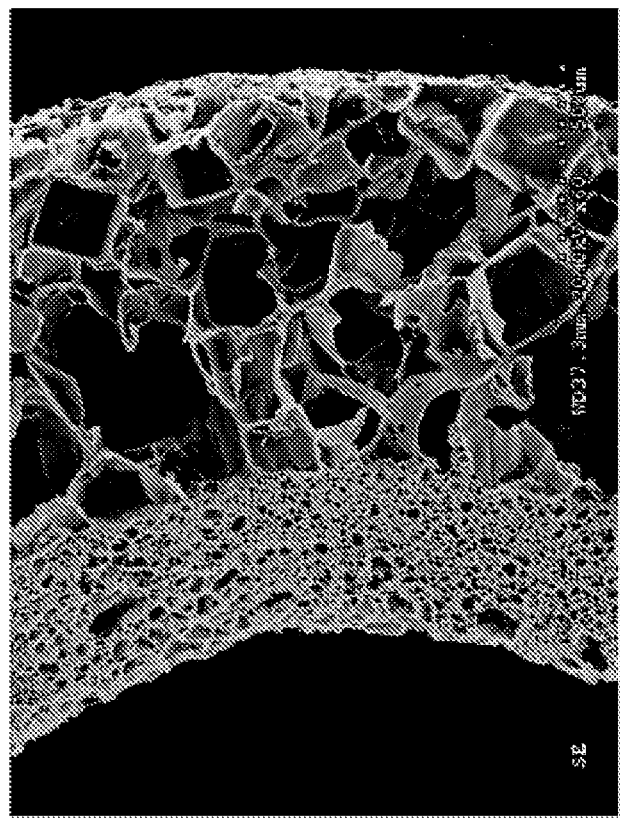
FIG. 16 illustrates a microscopy image of a scaffold according to one embodiment described herein.
Figure 17:
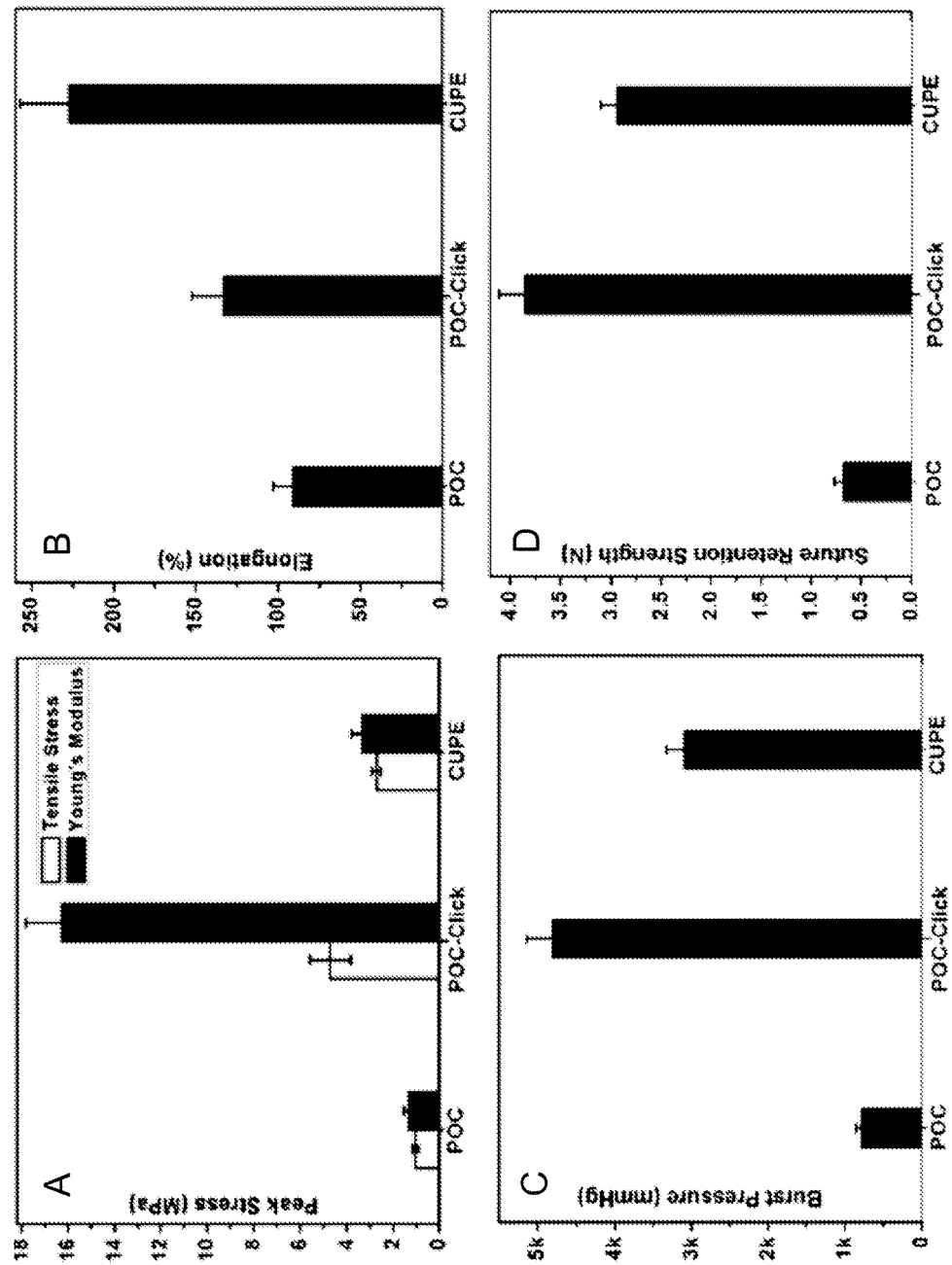
FIGS. 17(a)-17(d) illustrate plots of mechanical properties of compositions according to some embodiments described herein.

FIG. 16 illustrates a scanning electron microscope (SEM) image of the POC-click3 TTS. FIGS. 17(a)-17(d) illustrate some mechanical properties of the TTS. The tensile strength and Young's modulus of POC-click3 TTS (around 5 and 17 MPa respectively) in uniaxial tension were much higher than for a POC TTS (~1 and 1.2 MPa respectively), and even a little higher than for a CUPE TTS (~3.8 and 4 MPa respectively), indicating that the POC-click3 porous scaffold is strong enough to be used as a vascular graft. The burst pressure of POC-click3 TTS was around 5000 mm Hg, which is higher than that of parallel POC (less than 1000 mm Hg) and CUPE (around 3500 mmHg) TTS's, and also higher than that of both saphenous veins and mammary arteries (1599±877 and 4225±1368 mm Hg. respectively), which are currently used as the "gold standard" of vascular prostheses. By adjusting the thickness and porosities of POC-click3 TTS components, the burst pressure of a target vessel could be matched.

For implantation, in addition to suitable burst pressure, it is also desirable for a conduit such as a TTS to be sutured. The suture retention strength value of POC-click3 TTS was around 3.75 N, which is higher than both POC TTS (~0.75 N) and CUPE TTS (~3.0 N) controls, and also significantly higher than the reported value of 1.20±0.23 N required for suturing arterial vascular graft.

Through SPAAC, p15 was conjugated onto the surface of the inside layer of POC-click3 TTS, confirmed negatively by the change of FTIR spectra, and positively by the change of UV-vis spectra of the inside layers after Sakaguchi reaction. Not intending to be bound by theory, it is believed that the existence of pores may decrease the density of the functional groups (here, azide groups) on the surface of the POC-click scaffold, but should have no significant effect on the reactivity of the functional groups, thus allowing bioactive molecules to be conjugated to the surface easily.

Although described in detail in this Example primarily for POC-based elastomers, it is to be understood that other citrate-based elastomeric polymers (such as PAMC, CUPE, and BPLP) as well as other elastomeric polymers (such as PCL and PGS) may also be used. Bioelastomers provided herein can be used in biomedical applications such as tissue engineering, drug delivery, orthopedic fixation devices (such as bone screws, plates, and pins) and other medical implants. In addition, bioelastomers provided herein, such as POC-click biodegradable elastomers, can be used to directly composite with HA to form biodegradable bone putty for bone regeneration. Additional experimental details are provided below.

Materials 2,2-Bis(azidomethyl)propane-1,3-diol (diazido-diol monomer, DAzD) was synthesized as described in Zhang et al., *Macromolecules* 2011, 44, 1755-1759, and Xu et al., *Macromolecules* 2011, 44, 2660-2667. Propargyl 2,2-bis (hydroxylmethyl) propionate (alkyne-diol monomer, AlD) was synthesized according to Lu et al., *J. Polym. Sci. Part A: Polym. Chem.* 2007, 45, 3204-3217, and Shi et al., *Biomaterials* 2008, 29, 1118-1126. The synthesis of other azide/alkyne functional diol monomers described herein is provided below. The syntheses and purification procedures of 2-(azidomethyl)-2-methylpropane-1,3-diol and 2-(az-idomethyl)-2-ethylpropane-1,3-diol are the same as that of DAzD. The p15 peptide ($NH_2$-Gly-Thr-Pro-Gly-Pro-Gln-Gly-Ile-Ala-Gly-Gln-Arg-Gly-Val-Val-$CONH_2$) was purchased from United Peptide Corp. (Rockville, Md.). Click-easy® BCN N-hydroxysuccinimide ester I (used for SPAAC) was purchased from Berry & Associates, Inc. All other reagents were from Sigma-Aldrich and were used without further purification.

General Measurements $^1$H-NMR spectra of pre-polymers were recorded on a JNM ECS 300 spectrometer (JEOL, Tokyo, Japan) in DMSO-$d_6$. Attenuated total reflection Fourier transform infrared (ATR-FTIR) spectra were measured with a Nicolet 6700 FTIR spectrometer using films of pre-polymer in 1,4-dioxane solution or cross-linked polymer films directly. The morphology of tubular scaffolds was observed by SEM (Hitachi 3500 N, EPIC). UV-vis spectra were recorded using a UV-2450 spectrometer (Shimadzu, Japan) with a minimum wavelength resolution of 0.2 nm.

Polymer Synthesis and Film Making

POC was synthesized according to Yang et al., *Adv. Mater.* 2004, 16, 511-516; Yang et al., *Biomaterials* 2006, 27, 1889-1898; Dey et al., *Biomaterials* 2008, 29, 4637-4649; Dey et al., *J. Biomed. Mater. Res. A* 2010, 95A, 361-370; and Yang et al., *Tissue Eng.* 2005, 11, 1876-1886. Briefly, a mixture of citric acid (CA) and 1,8-octanediol (OD) (molar ratio of CA:OD was 1:1.1) was melted at 160° C. for about 20 min. Then the temperature was reduced to 140° C. and the reaction was continued for another ~1 hour until the stir bar twitched at a stir speed of 60 rpm. The crude product was purified by precipitating the oligomer/1,4-dioxane solution in water followed by freeze-drying. $^1$H NMR (300 MHz; DMSO-$d_6$; δ, ppm) of pre-POC: 1.15 (s, —$OCH_2CH_2$ ($CH_2)_4$— from OD), 1.50 (s, —$OCH_2CH_2$—), 2.50-2.90 (m, —OCO—$CH_2$—C(OH)(COO—)— from CA), 3.60 (br, —$CH_2$—OH from OD), 3.90-4.05 (br, —$COOCH_2$— from OD). FTIR of pre-POC (thin film, $cm^{-1}$): 1733 (COOR).

The POC pre-polymer was post-polymerized by heating in an oven at 100° C. for 3 days to create POC film. In this process, part of the unreacted —COOH and —OH groups of pre-POC were cross-linked. In addition, POC samples with cross-linking times of 1 or 2 days were also prepared keeping the temperature unchanged. FTIR of POC film ($cm^{-1}$): 1735 (COOR).

POC-Click

Functional POC pre-polymers with azide (POC-$N_3$) or alkyne (POC-Al) groups were synthesized by the copolymerization of CA, OD, and azide or alkyne functional diols (DAzD or AlD in FIG. 2(a)). After melting the mixture of CA and OD at 160° C., the reaction temperature was reduced to 120° C., followed by the addition of functional monomer (DAzD or AlD). Then the reaction was continued at 120° C. with nitrogen purging using a vent plug until the stir bar twitched at 60 rpm. The reactions often took more than 2 hours. The purification processes are the same as that of POC pre-polymer. For the POC-$N_3$ series, the molar ratios of CA:OD:DAzD for POC-$N_3$-1, POC-$N_3$-2, and POC-$N_3$-3 pre-polymers were 1:1:0.1, 1:0.9:0.2, and 1:0.8:0.3, respectively. $^1$H NMR (300 MHz; DMSO-$d_6$; δ, ppm) of pre-POC-$N_3$: 1.15 (s, —$OCH_2CH_2(CH_2)_4$— from OD), 1.50 (s, —$OCH_2CH_2$—), 2.60-2.90 (m, —OCO—$CH_2$—C(OH)(COO—)— from CA), 3.20-3.50 (br, —$CH_2$—$N_3$ from DAzD, —$CH_2$—OH from OD and DAzD), 3.80-4.05 (br, —$COOCH_2$— from OD and DAzD). FTIR of pre-POC-$N_3$ (thin film, $cm^{-1}$): 2109 (—$N_3$, strong), 1735 (COOR). Similarly, for POC-Al series, the monomer ratios of CA:OD:AlD for POC-Al-1, POC-Al-2, and POC-Al-3 pre-polymers were also 1:1:0.1, 1:0.9:0.2 and 1:0.8:0.3, respectively. $^1$H NMR (300 MHz; DMSO-d$_6$; δ, ppm) of pre-POC-Al: 1.05 (s, CH$_3$— from AlD), 1.20 (s, —OCH$_2$CH$_2$(CH$_2$)$_4$— from OD), 1.55 (s, —OCH$_2$CH$_2$— from OD), 2.60-2.90 (m, —OCO—CH$_2$—C(OH)(COO—)— from CA), 3.20-3.65 (br, —CH$_2$—OH from OD and AlD, —CCH from AlD), 3.85-4.15 (br, —COOCH$_2$— from OD and AlD), 4.60-4.70 (br, —CH$_2$—CCH from AlD). FTIR of pre-POC-Al (thin film, cm$^{-1}$): 2130 (—C≡CH, weak), 1735 (COOR).

Synchronous binary (SB) cross-linked POC films (POC-Click) were formed by heating the mixture of pre-POC-N$_3$ and pre-POC-Al at 100° C. for 3 days. In the process, post-esterification between unreacted —COOH and —OH groups of both pre-polymers as well as thermal alkyne-azide cycloaddition (AAC, or thermal click reaction) between alkyne groups of pre-POC-Al and azide groups of pre-POC-N$_3$ took place in the same post-polymerization process, thus leading to the name synchronous binary (SB) cross-linked POC, or POC-click for convenience.

POC-click samples with different cross-linking densities were obtained by adjusting the weight ratios between POC-N$_3$ and POC-Al pre-polymers (from 1/1 to 1/2, 1/4, and 1/6). The functional group content in POC-N$_3$ (from POC-N$_3$-1, POC-N$_3$-2, to POC-N$_3$-3) and POC-Al (from POC-Al-1, POC-Al-2, to POC-Al-3) pre-polymers, as well as heating times (from 1, 2, to 3 days), are shown in FIG. 7. FTIR of POC-Click film (cm$^{-1}$): 2109 (—N$_3$, still have), 1736 (COOR).

CUPE and CUPE-Click

Cross-linked urethane-doped polyester pre-polymer (pre-CUPE) was synthesized using 1,6-hexamethyl diisocynate (HDI) as chain-extender as described in Liu et al., *Prog. Polym. Sci.* 2012, 37, 715-765; Serrano et al., *Adv. Funct. Mater.* 2010, 20, 192-208; Wu et al., *Nat. Med.* 2012, 18, 1148-1153. The weight ratio between pre-POC and HDI was 1:0.22. Similarly, pre-CUPE-N$_3$ and pre-CUPE-Al were also synthesized using POC-N$_3$-1 and POC-Al-1 pre-polymers, respectively, to replace POC pre-polymer. The weight ratio between the pre-polymer and HDI was the same as for pre-CUPE. CUPE film was prepared by heating pre-CUPE at 100° C. for 3 days. Similarly, CUPE-N$_3$, CUPE-Al and CUPE-N$_3$, Al (equal-weight mixture of pre-CUPE-N$_3$ and pre-CUPE-Al) films were also formed under the same conditions.

CBPLP-Ser and CBPLP-Ser-Click

BPLP-Ser was synthesized using CA, OD, and L-Ser with a ratio of 1.0:1.1:0.2, as described in Avci-Adali et al., *Biomaterials* 2008, 29, 3936-3945. Similarly, BPLP-Ser-N$_3$ and BPLP-Ser-Al were also synthesized using CA, OD, DAzD or AlD (N$_3$ or alkyne functional monomer) and L-Ser with the molar ratio of 1.0:1.0:0.1:0.2. Cross-linked BPLP-Ser (cBPLP-Ser) film was formed by heating BPLP-Ser at 100° C. for 3 days. Also, cBPLP-Ser-N$_3$, cBPLP-Ser-Al, as well as cBPLP-Ser-N$_3$, Al (equal-weight mixture of BPLP-Ser-N$_3$ and BPLP-Ser-Al) films were prepared by cross-linking the corresponding polymers under the same condition as cBPLP-Ser.

Polymer Characterization

The thermal properties of cross-linked polymers were characterized by differential scanning calorimetry (DSC, −50° C. to ~150° C.) and thermal gravimetric analysis (TGA, 20° C. to ~800° C.) at a heating rate of 10° C./min under nitrogen atmosphere. The glass transition temperature (T$_g$) was determined by the first heating run to avoid the effect of further cross-linking in the measurement process. The decomposition temperature (T$_d$) was defined as the temperature with 5% weight loss of the samples.

The water-in-air contact angles of POC; POC-N$_3$-1, Al-1 (1/1); POC-N$_3$-2, Al-2 (1/1); POC-N$_3$-3, Al-3 (1/1) and PLLA films were measured at room temperature using the sessile drop method by a Rame-Hart goniometer and imaging system (Rame-Hart Inc., Mountain Lake, N.J.) within 10 s after dropping. See Yang et al., *Biomaterials* 2002, 23, 2607-2614. Four independent measurements at different sites were averaged. The change of water-in-air contact angle with time was also monitored from 0 to 30 minutes after water being dropped on the surface of the films. Elastomer densities were measured by a Mettler Toledo balance with a density determination kit (Greifense, Switzerland) based on Archimedes' principle. Distilled water was used as auxiliary liquid.

Mechanical tests were conducted with an MTS Insight 2 machine fitted with a 500 N load cell. The samples were cut into a narrow rectangle shape and elongated to failure. The Young's modulus was calculated by measuring the gradient at 10% of elongation of the stress-strain curve. Eight specimens per sample were tested and averaged.

Cross-linking density and molecular weight between cross-linking sites were evaluated according to the theory of rubber elasticity using Equation (2):

$$n = \frac{E_0}{3RT} = \frac{\rho}{M_c}, \qquad (2)$$

where n represents the number of active network chain segments per unit volume (mol/m$^3$); M$_c$ represents the molecular weight between cross-linking sites (g/mol); E$_0$ represents Young's modulus (Pa); R is the universal gas constant (8.3144 J/mol K); T is the absolute temperature (K); and ρ is the elastomer density (g/m$^3$) as measured via the method mentioned above.

Wet mechanical properties of the films were measured after immersing the films in PBS (pH 7.4) for about 24 hrs until the wet weight of the films stopped increasing.

In Vitro and In Vivo Degradation

For in vitro degradation, disk-shaped specimens (7 mm in diameter, with thickness around 0.15-0.30 mm) were placed in a tube containing 10 mL of phosphate buffered saline (PBS, pH 7.4) or NaOH solution (0.05 M) and incubated at 37° C. for pre-set times. Specimens were washed thoroughly with deionized (DI) water (more than 3 times) to remove any residual salt before freeze-drying, especially for the PBS degradation. Mass loss was calculated by Equation (1) hereinabove. Here, W$_0$ and W$_t$ are the initial weight and the weight after degradation, respectively. Four (NaOH degradation) or six (PBS degradation) specimens were performed and averaged for every sample. Results are presented as means±standard deviation.

For in vivo degradation, disk-shaped specimens of POC; POC-N$_3$-1, Al-1 (1/1); POC-N$_3$-3, Al-3 (1/1) and PLLA samples (8 mm in diameter, with thickness around 0.75-0.95 mm) were implanted subcutaneously in the back of healthy, 3 month old, female Sprague Dawley (SD) rats (Harlan Sprague Dawley Inc., Indianapolis, Ind.) after being sterilized by treating with 70% ethanol, sterilized PBS (pH 7.4), and UV light in sequence followed by drying in the cell culture hood overnight. Four specimens were used for each sample, and 4 rats were used in total.

After 20 weeks, the samples were removed from the rats, washed thoroughly with PBS solution and DI water, and then freeze-dried. The mass loss was also calculated using the mass loss equation above.

In Vitro Cell Cytotoxicity

The relative cytotoxicity of POC-N$_3$-1, Al-1 (1/1); POC-N$_3$-2, Al-2 (1/1); POC-N$_3$-3, Al-3 (1/1) was assessed with a MTT (methylthiazolyldiphenyl-tetrazolium bromide) assay against 3T3 fibroblast. POC and PLLA were used as the positive and negative control respectively. Samples were cut into discs (7 mm) to fit the inner diameter of 96-well plates. Then the samples were sterilized by treating with 70% ethanol, sterilized PBS (pH 7.4), and UV light in sequence. Subsequently, 200 μL of 3T3 cells in Dulbecco's modified eagle's medium (DMEM, with 10% fetal bovine serum (FBS)) at a density of 5×10$^4$ cells/mL was added to each well in a 96-well plate with disk-shaped specimens on the bottom. Specimens without seeding cells were used as control. MTT assay analysis was performed after incubating for 1, 3, and 7 days in an incubator (37° C., 5% CO$_2$) as described in previous work. See Tran et al., *Soft Matter* 2010, 6, 2449-2461.

Foreign Body Response

To assess the safety of dual cross-linked POC-Click polymer films in vivo, POC-N$_3$-1, Al-1 (1/1) and POC-N$_3$-3, Al-3 (1/1) were chosen as the representatives of POC-click polymers to do foreign body response studies using H & E staining and H & C (CD11b) staining POC and PLLA films were used as positive and negative control respectively. Disk-shaped films (8 mm in diameter, with thickness around 0.75-0.95 mm) were implanted subcutaneously randomly in the upper or lower back of healthy 3 month old female Sprague Dawley (SD) rats (Harlan Sprague Dawley Inc., Indianapolis, Ind.) after being sterilized and dried in the cell-culture hood as described above. Nine SD rats were divided into 3 groups with 3 rats each for 3 different time points (1, 4 and 12 weeks) of the study. At the end of each time point, 3 rats were sacrificed with excess CO$_2$, and polymer films with surrounding tissues were harvested and fixed by soaking in 10% formalin for 2 days. The samples were processed on an automated tissue processor. Then embedded in paraffin wax and sectioned into 4-μm sections. Six slides from different areas of the explants were stained with hematoxylin and eosin staining See Gyawali et al., *Biomaterials* 2010, 31, 9092-9105. To evaluate inflammatory cells, another 6 slides were stained with inflammatory cell marker CD11b (rat anti-mouse MAC-1, Santa Cruz Biotechnology) and peroxidase-conjugated goat anti-rat secondary antibodies (Jackson ImmunoResearch Laboratories, PA). See Zhou et al., *Biomaterials* 2011, 32, 9383-9390. Then the CD11b staining slides were treated with 3, 3-diaminobenzidine substrate system and counterstained with hematoxylin. The positive immunoreactions appeared as dark brown staining on a blue background. The cross-sections were examined using a Leica DMLP microscope (Leica Microsystems Inc., Bannockbum, Ill.) fitted with a Nikon E500 CCD camera (Nikon Corp., Japan). For quantitative analysis, all the cells in a 200×200 μm$^2$ region of the skin-side tissue near the implant films from 400× images of H & E staining were counted. For one sample, at least 8 different square regions from different specimens (implanted in different rats) were analyzed and the numbers were averaged. The CD11b+cells (with dark brown staining on a blue background) from the 400× images of H & C staining were also counted using the same method.

p15 Conjugation on POC-N$_3$-3, Al-3 (1/1) (POC-Click3) Film and Endothelial Cell (EC) Attachment and Proliferation P15 was first modified by copper-free clickable moieties to obtain clickable p15. Briefly, p15 was reacted with Click-easy® BCN N-hydroxysuccinimide ester I in DMSO solution at room temperature for 24 hrs to obtain clickable p15. Then a designated amount of DMSO solution of clickable p15 was diluted with DI water (v/v of water/DMSO=1/1) and used directly for strain-promoted alkykyne-azide cycloaddition (SPAAC) with POC-click3 films (37° C., 3*d*). P15 conjugated POC-click3 films were obtained after being washed with DI water followed by freeze-drying. The p15 conjugated POC-click3 film was characterized by FTIR and UV-vis spectra (using Weber's modified Sakaguchi reaction of guanidine group on p15). See Zhang et al., *Biomaterials* 2010, 31, 7873-7882. The amount of p15 conjugated on the film was also determined by UV-vis spectra (each p15 molecule contains one guanidine group) to be 10.6 nmol/cm$^2$, which is sufficient for endothelial cell attachment according to the literature. See *J. Biomater. Sci. Polymer Ed.* 2005, 16, 875-891.

P15 conjugated POC-click3 along with pure POC-click3 (100° C., 3*d*, used as control) samples were die-cut into discs with a diameter of 7 mm that matches the inner diameter of 96-well plates. The samples were all sterilized by treating with 70% ethanol, sterilized PBS (pH 7.4), and UV light in sequence and incubated in Dulbecco's Modified Eagle's Medium (DMEM) at 37° C. for 3-7 days prior to cell seeding. Primary human umbilical vein endothelial cells (HUVECs) were cultured in Endothelial Cell Growth Medium Bulletkit from Lonza (EGM-2 BulletKit) according to the manufacturer's instructions. The EGM-2 BulletKit contains a 500 mL EBM-2 Basal Medium and a set of supplements, EGM-2 SingleQuot Kit Suppl. & Growth Factors. All supplements were added to the 500 mL of EBM-2 Basal Medium before use. Cells were incubated at 37° C. with 98% humidity and 5% CO$_2$. The media was changed every other day. Frozen primary HUVEC cells from Lonza (first passage, P1) were first cultured on tissue culture polystyrene (PS) flasks (75 cm$^2$, Corning Acton, Mass. USA) at a loading density of 2500-5000 cells/cm$^2$. After cells reached around 75-90% confluence level (usually after about 6-7 days), they were harvested using 0.05% Trypsin/EDTA (Lonza) and frozen in liquid nitrogen for storage. The procedure was repeated to culture P2 cells to P3 cells. P3 HUVEC cells were seeded on the films in a 96-well plate (5000 cells/well) and incubated for 1, 3, and 7 days, then MTT reagent (5 mg/mL, 20 uL/well) was added to studied wells and the mixture was incubated at 37° C. for another 4 hours. The absorbance of the samples after MTT assay was measured via micro-plate reader at 570 nm. At the same time for each time point (day 1, 3, and 7), HUVECs on both p15 conjugated POC-click3 samples and POC-click3 samples were stained by Live/Dead Viability/Cytotoxicity Kit (Invitrogen, molecular probes, Eugene, Oreg.) for the observation of cell morphology and spreading using an inverted light microscope (Nikon Eclipse Ti—U) equipped with a ANDOR DL-604M-#VP camera and Prior Lumen 200. In addition, the morphology and spreading of HUVEC on p15 conjugated POC-click3 and POC-click3 samples at day 7 was imaged by scanning electron microscopes (SEM, FEI, Quanta 200) after the cells being fixed with 2.5% (wt/v) glutaraldehyde-PBS solution, followed by sequential dehydration by treatment with a graded series of ethanol (50%, 75%, 95% and 100%) and freeze-drying.

Tubular Triphasic Scaffold (TTS) Preparation and p15 Conjugation

Triphasic small diameter vascular graft scaffolds of POC-click3 (mixed POC-N$_3$-3 and POC-Al-3 with a w/w=1/1), POC, and CUPE composed of a rough inner lumen surface, a middle porous layer with pore size of 1-20 μm, and an outer porous layer with pore size of 150-250 μm, to replicate the stratified architecture of native blood vessels. See Yang et al., *Tissue Eng.* 2005, 11, 1876-1886; Dey et al., *J. Biomed. Mater. Res. A,* 2010, 95A, 361-370; and Zhang et al., *Biomaterials* 2013, 34, 4048-4056. Briefly, steel rods with 3 mm outer diameter were dip coated with a pre-polymer solution (30% w/w for POC and POC-click3, 3% w/w for CUPE) in 1,4-dioxane, and coated with NaCl (99% purity) with an average size of 1-20 μm. Next, NaCl with a size of 1-20 μm was mixed with a pre-polymer solution in a 1:5 polymer to salt weight ratio, and mixed until a viscous paste was formed. The paste was then transferred onto the steel rods to create a 200 μm thick layer. The entire construct was allowed to air dry and then cross-linked at 100° C. for 1 day. Next, another viscous pre-polymer-salt paste, made from a mixture NaCl (150-250 μm) and pre-polymer solution in a 1:10 polymer to salt weight ratio, was transferred over the previous layer to create an 800 μm thick layer. The steel rod/material assemblies were placed in a laminar flow hood overnight to remove all the solvent, and then transferred to an oven maintained at 100° C. for another 3 days for crosslinking After crosslinking, salt leaching was conducted by immersing the rod/material assemblies in DI water with completed water changes every 6 hours. The complete removal of salt was determined by testing with silver nitrate. The scaffolds were de-molded by swelling in 50% (v/v) ethanol solution in water followed by freeze-drying. Scaffold morphology was examined by scanning electron microscopy (SEM) (Hitachi S-3000N, Hitachi Science System, Ibaaki, Japan).

The mechanical properties, including peak loads, suture retentions, and burst pressures of POC-click3, POC and CUPE PTBSs were measured according to literature methods. See Dey et al., *J. Biomed. Mater. Res. A,* 2010, 95A, 361-370. P15 conjugated POC-click3 TTS was obtained by SPAAC between clickable p15 and the inside layer of POC-click3 PTBS by adding clickable p15 solution in DMSO into the inside hole of the biphasic scaffold with one end clipped. After reacting at 37° C. for 3 days, the scaffold was washed with DI water and then freeze-dried. So-obtained p15 conjugated POC-click3 scaffold was characterized by FTIR as well as UV-vis spectrometer (to verify p15 conjugation by Weber's modified Sakaguchi reaction of guanidine group on p15).

Example 2

Biphasic Scaffolds

Figure 18:
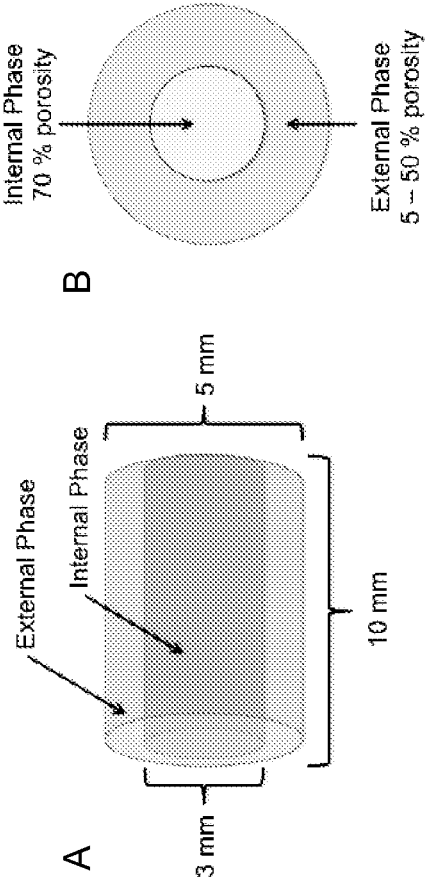
FIGS. 18(a) and 18(b) illustrate a perspective view and a sectional view, respectively, of a scaffold according to one embodiment described herein.

Biphasic scaffolds according to some embodiments described herein were prepared as follows.
A. Materials and Methods
Materials
Hydroxyapatite [Mw: 502.32, assay >90% (as $Ca_3(PO_4)_2$); particle size: >75 μm (0.5%), 45-75 μm (1.4%), <45 μm (98.1%)] was purchased from Fluka (St. Louis, Mo., USA). 1,8-octanediol (98%), citric acid (99.5%), and all remaining chemicals were purchased from Sigma-Aldrich (St. Louis, Mo., USA) and used as received unless stated otherwise.
Poly (Octanediol Citrate)-Click (POC Click) Synthesis
2,2-Bis(azidomethyl)propane-1,3-diol (diazido-diol monomer, DAzD) and propargyl 2,2-bis(hydroxyl-methyl) propionate (alkyne-diol monomer, AlD) were synthesized as described previously. POC Click pre-polymers with azide functionality (POC Click-$N_3$) were synthesized by the copolymerization of citric acid, 1,8-octanediol, and AlD in a 1.0:0.7:0.3 molar ratio, respectively. Briefly, a mixture of citric acid and 1,8-octanediol were added to a 100 mL three-necked round bottom flask fitted with an inlet and outlet adapter. The mixture was melted under a flow of nitrogen gas by stirring at 160° C. in a silicone oil bath. The temperature of the system was subsequently lowered to 120° C. followed by the addition of the AlD monomer, and allowed to react for 2 h to create the POC Click-$N_3$ pre-polymer. To remove any of the unreacted monomers and oligomers, the pre-polymer was dissolved in 1,4-dioxane, and purified by dropwise precipitation in deionized water produced from a Direct-Q 5Water Purification System (Millipore, Billerica, Mass.). The precipitate containing the undissolved pre-polymer was collected and lyophilized in a Freezone 6 Freeze Dryer (Labconco, Kansas City, Mo.) to obtain the purified pre-POC Click-$N_3$. POC Click pre-polymers with alkyne functionality (POC Click-Al) were synthesized as described above using citric acid, 1,8-octanediol, and DAzD in a 1.0:0.7:0.3 molar ratio, respectively.
Biphasic Scaffold Fabrication Biphasic scaffolds consisting of similar internal phase porosities and various external phase porosities were fabricated (FIG. 18). To create the external phase, equimolar amounts of pre-POC Click-$N_3$ and pre-POC Click-Al were dissolved in 1,4-dioxane and mixed with hydroxyapatite (65 wt. %). Sodium chloride salt with an average size in the range of 200-400 μm was added to the mixture in various concentrations (5-50 wt. %) to control the porosity of the external phase. To further control the porosity, it is also possible to use sodium chloride crystals having an average size between about 800 nm and about 1000 μm. Moreover, the concentration could also be from 0-50 wt. % or, in some cases, greater than 50 wt. %. The mixture was stirred in a Teflon dish until a homogenous viscous paste was formed. Next, cylindrically shaped scaffolds were formed by inserting the viscous paste into Teflon tubes (5×10 mm; inner diameter×length) purchased from McMaster-Carr (Aurora, Ohio, USA). Following solvent evaporation, the scaffolds were post-polymerized in an oven maintained at 100° C. for 1 day.

To create the internal phase, a 3 mm hole was lathed into the center of the scaffolds, and a paste similar to the above mentioned procedure was created with a 70 wt. % salt concentration. Other concentrations of salt could also be used, such as a concentration between about 50 wt. % and about 80 wt. %. The resulting paste was inserted into the lumen of the external phase and allowed to dry overnight in a laminar flow hood. After solvent evaporation, the scaffolds were post-polymerized in an oven maintained at 100° C. for 2 days followed by heating at 120° C. under 2 Pa vacuum for 1 day. Salt was leached out from the scaffolds by immersion in deionized water for 72 hours with water changes every 12 hours. Finally, the scaffolds were dried using lyophilization to obtain the final biphasic scaffolds (5×10 mm; diameter× length). Biphasic scaffolds are referred to as biphasic-X, where X denotes the salt weight percentage used to create the external phase during fabrication.
Single-Phase Scaffold Fabrication To fabricate scaffolds of uniform porosity (70%), a paste similar to the inner phase fabrication was inserted into Teflon tubes (5×10 mm; inner diameter×length). Following solvent evaporation, the scaffolds were post-polymerized in an oven maintained at 100° C. for 3 days followed by 120° C. under 2 Pa vacuum for 1 day and processed as mentioned above.
Biphasic Scaffold Morphology and Porosity Characterization To view the scaffold cross-sectional morphology, samples were sputter coated with gold and viewed under a FEI Quanta 200 Environmental Scanning Electron Microscope (SEM) (FEI, Hillsboro, Oreg., USA). To characterize the scaffold geometries, 3 random locations were selected and a total of 30 measurements were recorded using NIH Image J analysis software (National Institute of Health, Md., USA).

Scaffold Mechanical Characterization

Unconfined compression tests were performed using a 5900 series advanced electromechanical testing system (Instron, Norwood, Mass., USA). Briefly, cylindrical shaped scaffolds 5×10 mm (diameter×height) were compressed at a rate of 2 mm min$^{-1}$ to failure. Values were converted to stress-strain and the initial modulus (MPa) was calculated from the initial gradient of the resulting curve (0-10% compressive strain). The peak stress (MPa) and compressive strain at break (%) were also recorded.

Biphasic Scaffold In Vivo Evaluation

New Zealand white rabbits (2.0-2.2 kg in weight) from the Laboratory Animal Center of Southern Medical University (Guangzhou, China) were used to evaluate the ability of the scaffolds to repair a 10 mm segmental bone defect in vivo. All animal experiments were carried out in compliance with a protocol approved by Southern Medical University's Institutional Animal Care and Use Committee. The rabbits were first anesthetized with an ear vein injection of 3% sodium pentobarbital (1.5 mL/kg). A 20 mm incision was made over the middle third of the left radius, and the overlying tissues were dissected to expose the radial diaphysis. Next, a 10 mm segmental defect was created with a low-speed electric saw and immediately treated with the following experimental groups: 1. Single-phase scaffolds (70% uniform porosity) (the "Single-phase" group) and 2. Biphasic-50 scaffolds (70% internal phase porosity; 50% external phase porosity) (the "Biphasic-50" group). For controls, animals were also treated with autologous bone grafts (positive control; the "Autologous bone" group) or left empty as an untreated defect (negative control; the "Empty defect" group). Since no specific osteoinductive or osteogenic factors were incorporated into the tested graft substitutes (except those inherent in the positive control), a more demanding 20 mm critical-sized defect model was not used, and healing of a 10 mm defect was employed to allow for better characterization of the osteoconductive and osteoinductivepotential of the graft substitutes. Rabbits were sacrificed at 5, 10, and 15 weeks after surgery and subjected to the following assessments.

Radiographic Examination

All samples were analyzed by computer tomography analysis using a Micro-CT imaging system (ZKKS-MCT-Sharp-III scanner, Caskaisheng, CHINA). The images were reconstructed using ZKKS-MicroCT 3.0 software to generate gray scale images ranging from 0 to 255, which is equivalent to the density range of 0.81-3.34 g cm$^{-3}$. New bone formation was defined by the density difference between scaffold (2.5 g cm$^{-3}$) and newly forming osteoids or native bone remodeling (1.2-1.7 g cm$^{-3}$). Specifically, optical density was used to measure the percentage of newly formed bone in the total area of implantation. Since newly formed bone could not be separated from the autograft implant, the reported bone optical density data includes both the regenerated bone as well as the remodeled autograft. Total bone formation within the defect spaces was also measured, which included the calcified interosseoussyndesmosis but excluded the ulna. Bone-to-implant areas were calculated as the surface border length of the newly formed bone in direct contact with the implant divided by the total implant perimeter based on the micro-CT images.

Histological Analysis

For histological analysis, paraffin-embedded decalcified tissues were cut into 4 μm thick sections, which were then deparaffinated, hydrated, and stained with hematoxylin and eosin (H&E) and Goldner's Trichrome. After microscopic examination, computer-assisted histomorphometric measurements of newly formed bone were obtained using an automated image analysis system (FreeMaxver 3.0, Zhongrui, Taiwan) equipped with a CCD camera (Kodak DCS, Atlanta, Ga., USA) on a light microscope.

Biomechanical Testing

Rabbits from each group were sacrificed at 15 weeks post-implantation. The soft tissue of the forearm, including the periosteum, was carefully dissected from the radii to reveal the area of the bone defect without touching the bone. The explanted radius was then assessed for healing. The two cutting ends of the specimens (four radii) were fixed with clamps with an average span of 20 mm. The maximal bending strength of the radial segment was measured with an ElectroForce 3510 Universal Material Testing Machine (Bose, Eden Prairie, Minn., USA). The test was motion-controlled with a speed of 2 mm min$^{-1}$. Values were converted to stress-strain and the initial modulus was calculated from the initial gradient of the resulting curve (0-10% compressive strain).

Statistical Analysis

Data are expressed as the mean±standard deviation. The statistical significance between two sets of data was calculated using a two-tail Student's t-test. Analysis of variance (ANOVA) with Newman-Keuls multiple comparisons test post-hoc analysis was used to determine significant differences among three or more groups. Data analysis was performed using SPSS software (SPSS, Chicago, Ill., USA). Data was considered to be significant when a P-value of 0.05 or less was obtained.

B. Results

Biphasic Scaffold Morphology

Figure 19:
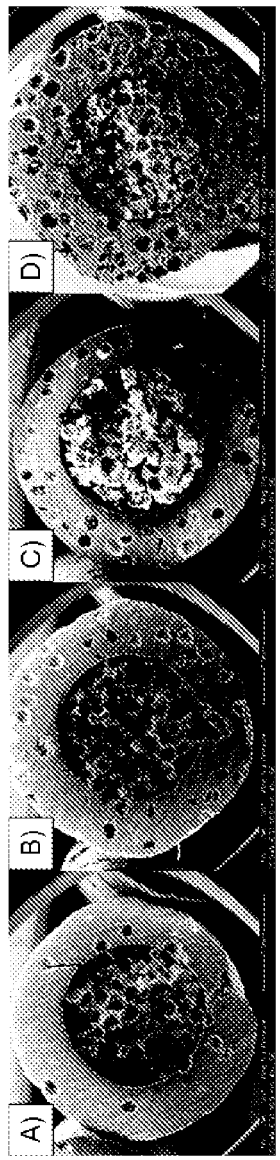
FIGS. 19(a)-19(d) illustrate microscopy images of scaffolds according to some embodiments described herein.

SEM images of the biphasic POC-Click-HA scaffold fabricated with various external phase porosities are shown in FIG. 19, which show the presence of two distinct scaffold architectures. The external phases in FIG. 19 correspond to biphasic-5 (FIG. 19(*a*)), biphasic-10 (FIG. 19(*b*)), biphasic-24 (FIG. 19(*c*)), and biphasic-50 (FIG. 19(*d*)). Biphasic internal and external phase diameters were measured to be 2.96±0.05 mm and 5.02±0.07 mm, respectively. The average pore size for all scaffolds was measured to be 338.12±42.06 μm.

Biphasic Scaffold Mechanical Properties

Figure 20:
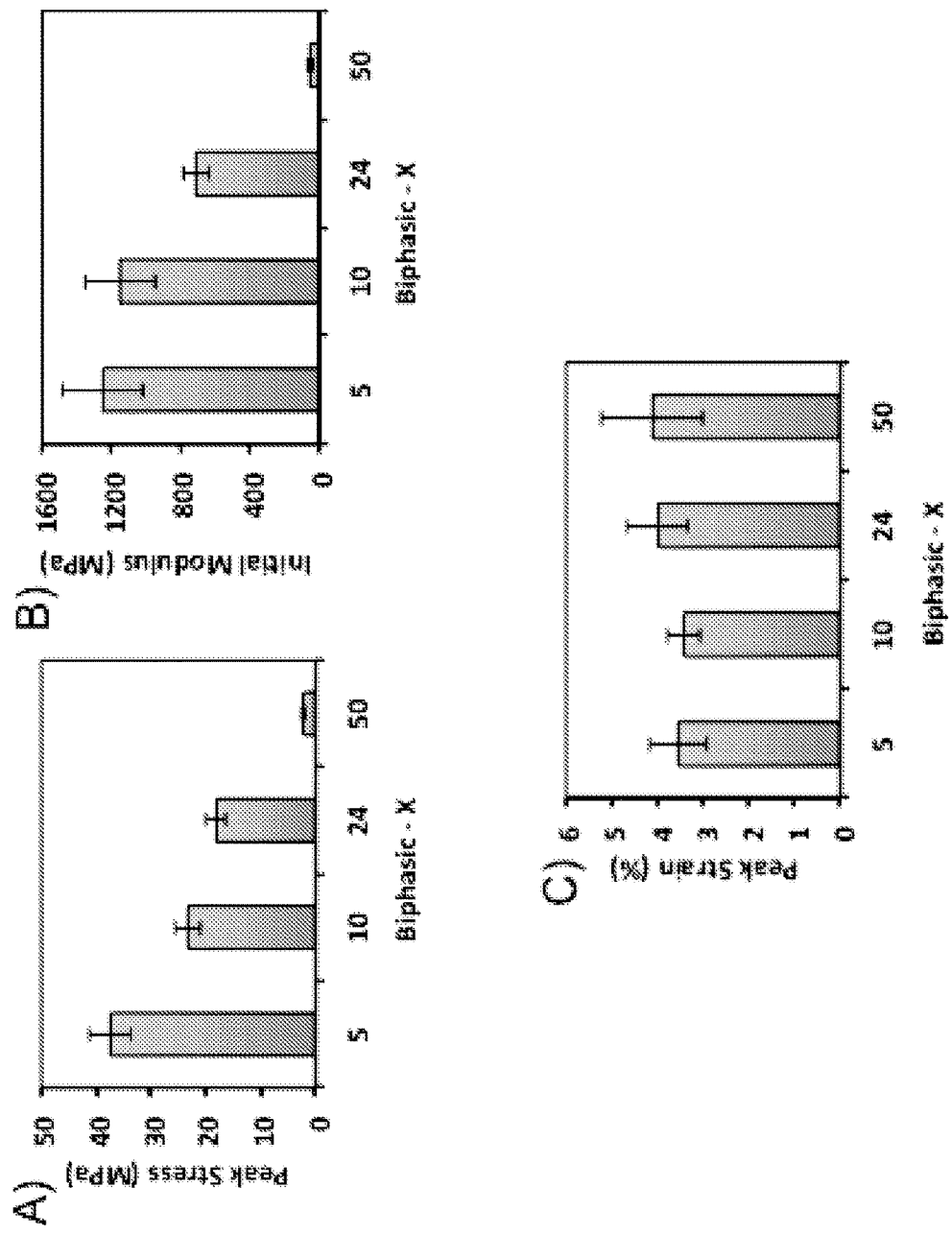
FIGS. 20(a)-20(c) illustrate plots of mechanical properties of scaffolds according to some embodiments described herein.

The fabricated scaffolds were evaluated for their compressive peak stress, initial modulus, and peak strain at break. As shown in FIGS. 20(*a*) and 20(*b*), a decreasing trend in peak stress and initial modulus was seen as the porosity of the external phase was increased. Compressive peak stress values significantly decreased from 37.45±3.83 down to 2.26±0.27 MPa for biphasic-Sand 50 scaffolds, respectively (p<0.05). A similar inverse relationship was seen for the initial modulus, which shows a decrease from 1250.01±230.60 down to 55.15±15.83 MPa as the external phase porosity was increased from 5 to 50% (FIG. 20(*b*)). In contrast, FIG. 20(*c*) shows that the compressive strain at break increased in correlation with the external phase porosity, but was not significantly different (p >0.05).

Gross Evaluation

To assess efficacy of POC-Click-HA biphasic scaffolds in the repair of long bone defects, biphasic-50 scaffolds were implanted in a 10 mm segmental left radial diaphysis defect of rabbits. No operative or postoperative complications were encountered for all experimental groups. There was no evidence of wound infection at the implant site, and all rabbits recovered well without any signs of erythema, swelling, or sinus tract formation. After 15 weeks of implantation, macroscopic evaluation revealed that the implant positioning was maintained in the defect site throughout the experimental time frame for both single-phase and biphasic scaffolds. New bone ingrowth was prominent in the experimental and positive control groups. POC-Click-HA scaffolds showed close-to-complete resorption. However, an obvious defect was present in the negative control group.

Radiographic Examination

Figure 21:
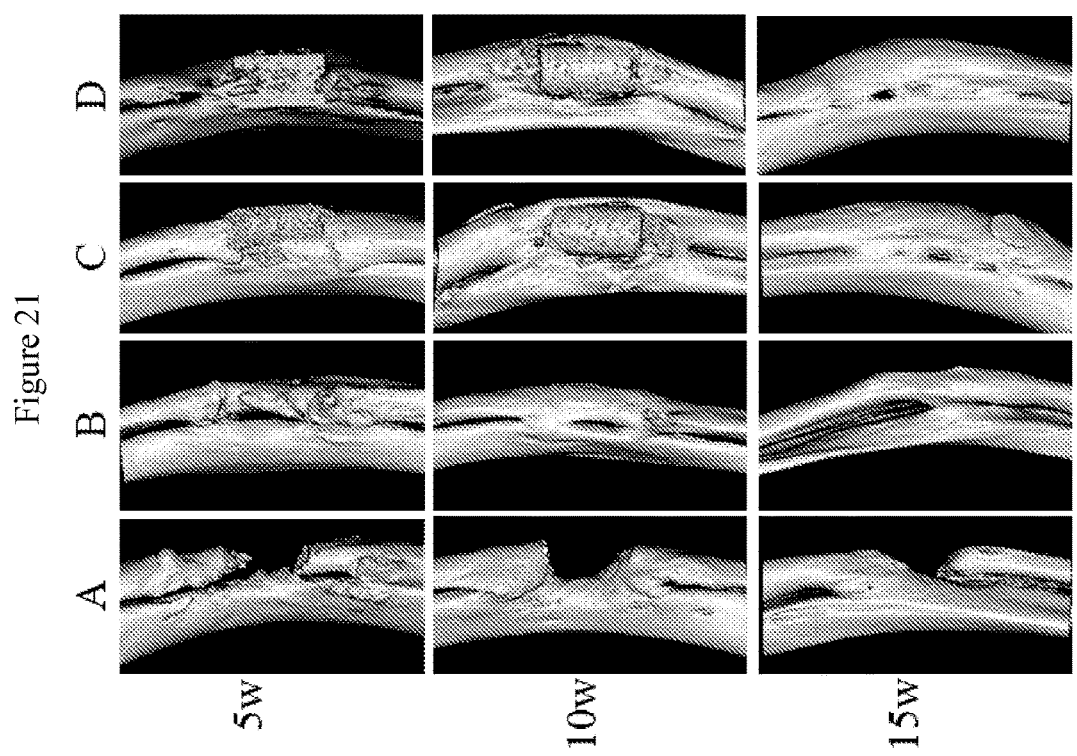
FIGS. 21(a)-21(d) illustrate CT images of bone defects treated by scaffolds according to some embodiments described herein.

Micro-CT images were used to evaluate the extent of new bone growth at each time point. FIG. 21(a) shows CT images for empty defect (untreated negative control), FIG. 21(b) shows autologous bone grafts (positive control), FIG. 21(c) shows POC-Click-HA single-phase scaffold, and FIG. 21(d) shows POC-Click-HA biphasic-50 scaffold. As shown in FIG. 21, when the radial defects were left alone and not treated with any filling material, the medullary cavity remained unrepaired without any observable bone regeneration after 15 weeks (FIG. 21(a)). In contrast, autologous bone graft treated animals displayed dense newly formed bone by 5 weeks with an increase in bone regeneration at 10 weeks post-surgery. By 15 weeks, the bone defects were repaired, and the medullary cavity was bridged. However, the diameter of the regenerated radius was smaller when compared to experimental groups (FIG. 21(b)). Animals treated with single-phase scaffolds displayed a periosteal reaction with new bone regeneration seen after 5 weeks of implantation. The periosteal callus became thicker throughout the study and surrounded the periphery of the scaffold with bone-to-implant contact (BIC) values of 70%. By 15 weeks, the defects were mostly repaired, and the medullary cavity was partially bridged (FIG. 21(b)). In the case of biphasic-50 scaffolds, a high density of transplanted bone was observed after 5 weeks of implantation with signs of obvious resorption of the internal phase. The biphasic scaffolds were surrounded with newly formed bone and successfully anchored to the host bone tissue. After 10 weeks, the bone defects were largely repaired, and the originally disconnected medullary bone cavity was bridged. The defects were completely repaired after 15 weeks with close-to-complete resorption of the scaffolds (FIG. 21(c)). Quantitative analysis of BIC showed significantly higher values in the experimental groups when compared to autologous bone grafts at the 5-week time point (Table 1).

Histological Analysis

Figure 22:
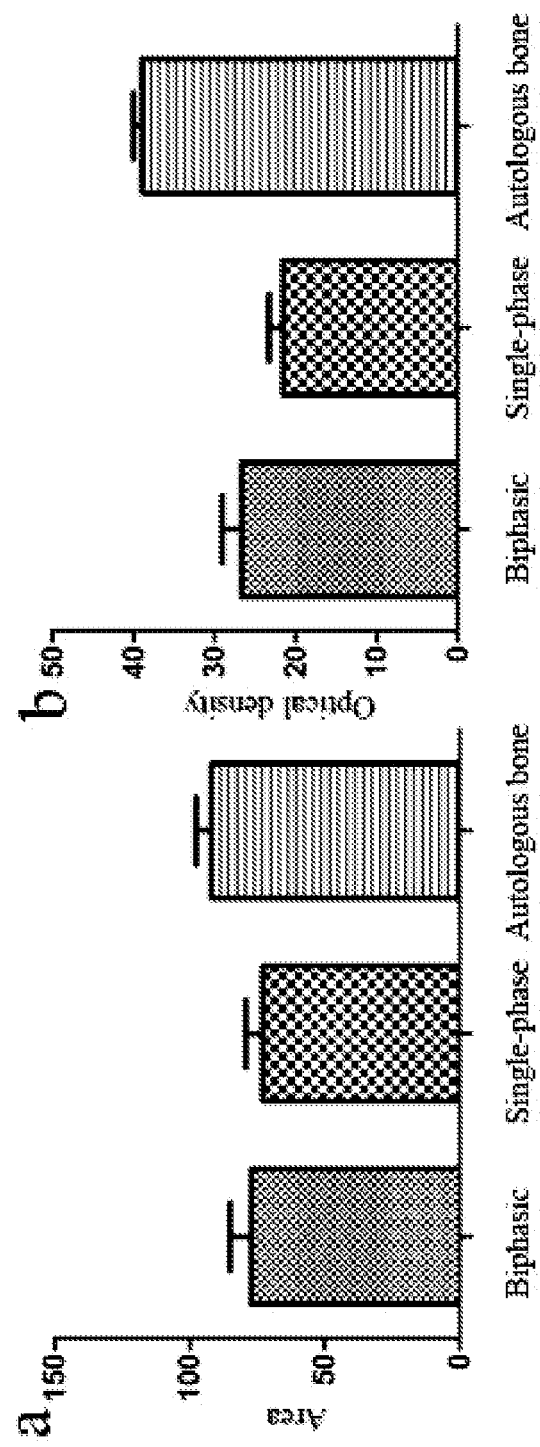
FIGS. 22(a) and 22(b) illustrate plots of properties of scaffolds according to some embodiments described herein.

Upon histological evaluation, no inflammation or the presence of macrophages or giant cells was observed at the implant-bone interface. Fibrous tissue was present within the single-phase scaffolds and at the implant-bone interface, while little fibrous tissue was present within the biphasic-50 scaffolds, which showed that biphasic scaffold architectures could reduce fibrous infiltration. New bone ingrowth was prominent in the experimental groups, and, notably, the animals treated with both single-phase and biphasic scaffolds showed periosteal remodeling after 5 weeks of implantation. Quantitative determination of histology demonstrated comparable results among experimental treatment groups (single-phase and biphasic-50 scaffold treated groups) and autologous bone graft treated animals at 15 weeks (FIG. 22). In FIG. 22, the reported areas represent the percentages of the bone-to-implant contact areas. The reported optical densities represent the percentages of new bone in the implant areas.

Biomechanical Testing

Figure 23:
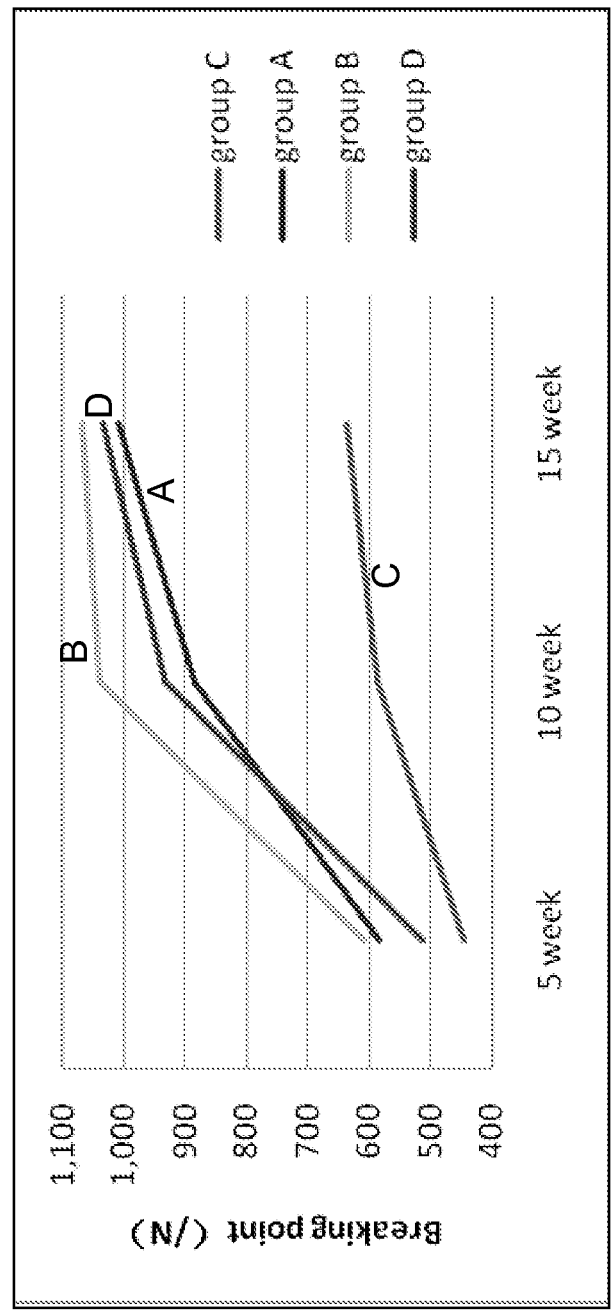
FIG. 23 illustrates plots of properties of scaffolds according to some embodiments described herein.

There was a significant increase in compression properties of radius treated with single-phase and biphasic-50 scaffolds after 5 weeks when compared to control groups (no treatment and autologous bone). Additionally, the load bearing ability of radii treated with the biphasic scaffolds was higher than those treated with single-phase scaffolds, but was not statistically significant at 15 weeks. The biomechanical testing showed breaking points of 582.8±45.1 N, 608.0±53.6 N, 445.2±3 8.2 N, and 514.0±60.9 N for the single-phase scaffolds, biphasic-50 scaffolds, negative control (no treatment), and positive control (autograft), respectively, after 5 weeks of implantation. At the end of the 15-week study period, breaking points of 1008.8±54.2 N, 1066.4±69.2 N, 637.0±29.6 N, and 1034.6±84.4 N were recorded, respectively. Flexural testing of the rabbit radius-ulna complex at 5 weeks revealed significantly better elastic modulus and flexural strength recovery in the biphasic scaffolds when compared to the single-phase scaffolds and autograft groups (Table 2, FIG. 23).

TABLE 1

Quantification of bony analysis (mean ± SD).

| | 5 weeks | | 10 weeks | | 15 weeks | |
|---|---|---|---|---|---|---|
| | BMC (mg) | BMD (mg/cm$^3$) | BMC (mg) | BMD (mg/cm$^3$) | BMC (mg) | BMD (mg/cm$^3$) |
| Single-phase | 2.95 ± 0.13$^a$ | 776.5 ± 43.1$^a$ | 3.21 ± 0.20$^a$ | 792.1 ± 67.2$^a$ | 3.04 ± 0.17$^a$ | 850.9 ± 50.9$^a$ |
| Biphasic | 3.17 ± 0.16$^{ac}$ | 808.7 ± 36.6$^a$ | 3.24 ± 0.19$^a$ | 850.6 ± 65.1$^a$ | 3.07 ± 0.16$^a$ | 873.8 ± 55.3$^a$ |
| Empty defect | 2.20 ± 0.19 | 574.1 ± 19.9 | 2.65 ± 0.21 | 684.3 ± 31.1 | 3.36 ± 0.20 | 743.4 ± 64.7 |
| Autologous bone | 3.05 ± 0.15$^a$ | 798.7 ± 50.3$^a$ | 3.17 ± 0.21$^a$ | 858.7 ± 86.8$^a$ | 3.03 ± 0.19$^a$ | 838.2 ± 51.6$^a$ |

$^a$statistically different from Empty defect (untreated negative control) at the same time point (P < 0.05), $^c$statistically different between Single-phase group and Biphasic-50 group at the same time point (P < 0.05).

TABLE 2

Results of biomechanical testing (mean ± SD).

| | 5 weeks | | 10 weeks | | 15 weeks | |
|---|---|---|---|---|---|---|
| | Flexural Strength (N) | Elastic modulus (N/m$^2$) | Flexural Strength (N) | Elastic modulus (N/m$^2$) | Flexural Strength (N) | Elastic modulus (N/m$^2$) |
| Single-phase | 517.5 ± 26.4$^{ab}$ | 155.7 ± 25.8$^a$ | 735.0 ± 29.7$^a$ | 195.0 ± 29.6$^{ab}$ | 896.1 ± 38.2$^a$ | 229.9 ± 40.4$^a$ |
| Biphasic | 697.6 ± 24.8$^{abc}$ | 162.7 ± 30.3$^a$ | 852.1 ± 27.2$^{abc}$ | 205.2 ± 34.9$^{ab}$ | 911.5 ± 29.0$^a$ | 240.1 ± 32.2$^a$ |
| Empty defect | 343.9 ± 24.2 | 93.7 ± 19.3 | 444.7 ± 32.7 | 117.9 ± 24.7 | 536.2 ± 31.4 | 143.7 ± 20.8 |
| Autologous bone | 613.8 ± 30.1$^a$ | 175.4 ± 23.7$^a$ | 771.6 ± 39.8$^a$ | 252.6 ± 41.8$^a$ | 870.0 ± 23.0$^a$ | 241.3 ± 42.8$^a$ |

$^a$significantly different from empty defect group at the same time point ($p < 0.05$),
$^b$significantly different from autologous bone graft group at the same time point ($p < 0.05$),
$^c$significantly different between Single-phase group and Biphasic-50 group at the same time point ($p < 0.05$).

C. Discussion

Biomimetic citrate-based biphasic scaffolds are described herein to replicate the native compositional and architectural properties of native bone tissue, which can provide immediate structural support and long-term tissue regeneration for large segmental bone defects. In addition, as described herein, the following has been discovered. 1) The use of a citrate-based material can provide a highly effective means to replicate the organic cell niche found in natural bone to improve biocompatibility and enhance bone formation. 2) Citrate located in the bulk of the material provides pendant carboxyl chemistry to chelate with HA particles and allow for the incorporation of up to 65 wt. % to match the native inorganic mineral content. 3) POC-Click biomaterials can be composited with HA and crosslinked through clickable moieties to preserve valuable citrate carboxyl chemistry for HA binding resulting in strong composites. 4) A biphasic scaffold design can better simulate the bimodal distribution of highly porous cancellous bone and dense compact structure of cortical bone and provide immediate structural support following implantation. 4) To impart porosity into the grafts, a cost-efficient and facile solvent casting particulate leaching technique can be used. One major advantage to this approach is that the overall dimensions, geometry, and phase porosities can be controlled using various Teflon mold and lathe drill bit dimensions to fine-tune the resulting scaffold architecture and resulting mechanical properties to meet the requirements for various anatomical locations.

SEM analysis of the POC-Click-HA biphasic scaffolds shows the clear presence of a dense external phase surrounding a porous internal phase to replicate the native cortical and cancellous bone, respectively (FIG. 19). The resulting porosities were chosen in order to match the respective porosities of native bone, which have been found to be 10% for cortical bone and 50-90% for trabecular bone. The size of the pores was chosen to be in the range of 200-400 μm. Native bone tissue is highly dynamic and rigid tissue. The mechanical properties of the POC-Click-HA biphasic scaffolds fabricated in this study were highly dependent upon the resulting porosity of the external phase. Not intending to be bound by theory, FIG. 20 shows a corresponding increase in compressive strength as the porosity of the external phase was reduced, indicating that the mechanical strength of the scaffolds was primarily due to the external phase.

In addition to mechanical testing, the fabricated POC-Click-HA biphasic scaffolds were compared with single-phase scaffolds and autologous bone grafts in vivo using a 10 mm rabbit radius defect to determine their ability to regenerate large segmental bone defects. POC-Click-HA scaffolds of uniform porosity (70%) were fabricated with porosities similar to the internal phase of the biphasic scaffolds, and POC-Click-HA biphasic-50 scaffolds were selected for implantation due to the balance between external phase porosity and strength. Histological results show the presence of new bone ingrowth into both single-phase and biphasic POC-Click-HA scaffolds. Not intending to be bound by theory, combined with micro-CT analysis, the results show that citrate-based scaffolds significantly increased BMC after 5 weeks of implantation when compared to autologous bone grafts, possibly emphasizing the importance of a porous component in the scaffold architecture, which may provide the appropriate space for the migration of bone-forming cells and promotes the bone bridge connection to ultimately shorten recovery times (Table 1). By the end of the study, both single-phase and biphasic scaffold architectures were able to completely repair the defect and showed close-to-complete resorption.

In addition, comprehensive biomechanical analysis of the two experimental groups described herein revealed that the restoration of flexural strength, BMC, and toughness of the biphasic group were all significantly greater than the single-phase group. Not intending to be bound by theory, it is believed that the low porosity external phase of the biphasic scaffold design not only serves to mimic native cortical to withstand the biomechanical forces traversing the defect, but also prevents fibrous tissue ingrowth by functioning as a barrier similar to collagen membranes. It is worthy to note that the in vivo results presented above on long bone regeneration were based on bare POC-Click-HA scaffolds without any supplements or growth factors.

In conclusion, biomimetic citrate-based biphasic scaffolds were fabricated to replicate the native architecture of cortical and cancellous bone using a simple and cost-effective sodium chloride particulate leaching technique. Using this design, various biphasic scaffolds can be produced with tunable architectural geometries and strength. The resulting scaffolds were evaluated based on their geometry, mechanical properties, and in vivo performance. Such architecturally and compositionally biomimetic citrate-based scaffolds can serve as off-the-shelf implants to provide immediate structural support for large bone defects.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

That which is claimed is:

1. A composition comprising a polymer formed from one or more monomers of Formula (A); one or more monomers of Formula (B1), (B2), or (B3); and one or more monomers comprising one or more alkyne moieties and/or one or more azide moieties:

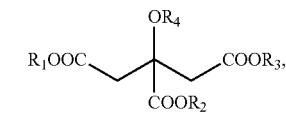
(A)

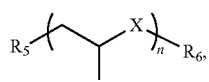
(B1)

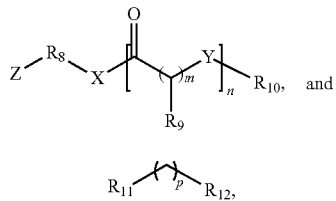
(B2)

(B3)

wherein $R_1$, $R_2$, and $R_3$ are independently —H, —CH$_3$, —CH$_2$CH$_3$, or M$^+$;

$R_4$ is —H;

$R_5$ is —H, —OH, —OCH$_3$, —OCH$_2$CH$_3$, —CH$_3$, —CH$_2$CH$_3$, —NH$_2$, NHCH$_3$, —CH$_2$CH$_2$NHCH$_3$, —N(CH$_3$)$_2$, or —CH$_2$CH$_2$N(CH$_2$CH$_3$)$_2$;

$R_6$ is —H, —CH$_3$, or —CH$_2$CH$_3$;

$R_7$ is —H or —CH$_3$;

$R_8$ is —(CH$_2$)$_a$, —(CH$_2$CH$_2$O)$_b$—, or —(CH$_2$OCH$_2$)$_b$—;

$R_9$ is —H, —CH$_3$, or a C2-C20 alkyl;

$R_{10}$ is —H, —C(O)CH$_3$, or —C(O)CH$_2$CH$_3$;

$R_{11}$ and $R_{12}$ are independently —OH or —NH$_2$;

M$^+$ is a monovalent cation;

X and Y are independently —O— or —NH—;

Z is —H or —CH$_3$, or

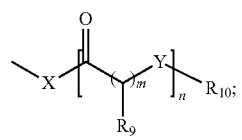

a is an integer from 0 to 20;

b is an integer from 0 to 2000;

n is an integer between 1 and 2000; and m and p are independently integers ranging from 1 to 20; and wherein the monomer of Formula (B1) has at least one terminus comprising —OH or —NH$_2$; and wherein, in the alternative, either:

(a) the one or more monomers comprising one or more azide moieties comprises a monomer of Formula (G1) or (G2):

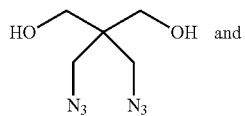
(G1)

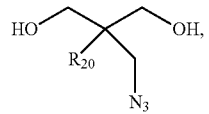
(G2)

wherein $R_{20}$ is —CH$_3$ or —CH$_2$CH$_3$, or (b) the one or more monomers comprising one or more alkyne moieties comprises a monomer of Formula (H1), (H2), (H3), (H4), (H5), or (H6):

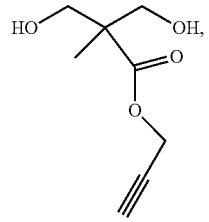
(H1)

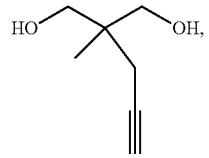
(H2)

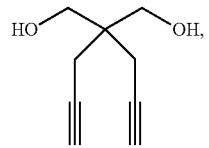
(H3)

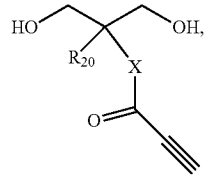
(H4)

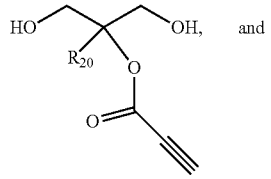
(H5)

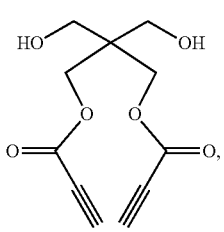 (H6)

wherein
R$_{20}$ is —CH$_3$ or —CH$_2$CH$_3$; and
X is —NH—.

2. The composition of claim 1, wherein one or more monomers of Formula (B1) are used and X is —O—.

3. The composition of claim 1, wherein the one or more monomers comprising one or more alkyne and/or azide moieties comprises a polyol.

4. The composition of claim 1, wherein the composition comprises a first polymer formed from one or more monomers of Formula (A); one or more monomers of Formula (B1), (B2), or (B3); and one or more monomers comprising one or more alkyne moieties; and a second polymer formed from one or more monomers of Formula (A); one or more monomers of Formula (B1), (B2), or (B3); and one or more monomers comprising one or more azide moieties.

5. The composition of claim 4, wherein the composition comprises an azide-alkyne cycloaddition product.

6. The composition of claim 1, wherein the polymer is formed from one or more monomers of Formula (A); one or more monomers of Formula (B1), (B2), or (B3); one or more monomers comprising one or more alkyne moieties and/or one or more azide moieties; and one or more monomers of Formula (C1), (C2), (C3), or (C4):

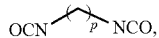 (C1)

(C2)

(C3)

(C4)

wherein p is an integer ranging from 1 to 10.

7. The composition of claim 1, wherein the polymer is formed from one or more monomers of Formula (A); one or more monomers of Formula (B1), (B2), or (B3); one or more monomers comprising one or more alkyne moieties and/or one or more azide moieties; and one or more monomers of Formula (D1) or (D2):

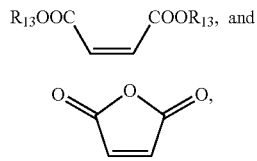 (D1)

(D2)

wherein
R$_{13}$ is —H, —CH$_3$, or —CH$_2$CH$_3$.

8. The composition of claim 1, wherein the polymer is formed from one or more monomers of Formula (A); one or more monomers of Formula (B1), (B2) or (B3); one or more monomers comprising one or more alkyne moieties and/or one or more azide moieties; and one or more monomers of Formula (E):

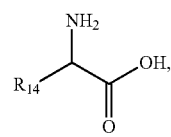 (E)

wherein
R$_{14}$ is a side chain of an amino acid or an alkyl-substituted amino acid.

9. The composition of claim 1, wherein the polymer is formed from one or more monomers of Formula (A); one or more monomers of Formula (B1), (B2) or (B3); one or more monomers comprising one or more alkyne moieties and/or one or more azide moieties; and one or more monomers of Formula (F):

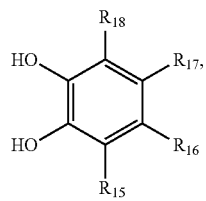 (F)

wherein
R$_{15}$, R$_{16}$, R$_{17}$, and R$_{18}$ are independently —H, —CH$_2$(CH$_2$)$_x$NH$_2$, —CH$_2$(CHR$_{19}$)NH$_2$, or —CH$_2$(CH$_2$)COOH;
R$_{19}$ is —COOH or —(CH$_2$)$_y$COOH;
x is an integer ranging from 0 to 20; and
y is an integer ranging from 1 to 20.

10. The composition of claim 1, wherein the one or more monomers comprising one or more azide moieties comprises a monomer of Formula (G1) or (G2).

11. The composition of claim 1, wherein the one or more monomers comprising one or more alkyne moieties comprises a monomer of Formula (H1), (H2), (H3), (H4), (H5), or (H6).

12. The composition of claim 1, further comprising a particulate inorganic material dispersed within a network formed by the polymer.

13. The composition of claim 12, wherein the particulate inorganic material comprises hydroxyapatite.

14. The composition of claim 12, wherein the particulate inorganic material is present in the polymer network in an amount up to about 70 weight percent, based on the total weight of the polymer network.

15. A core-shell polymeric scaffold comprising:
a core component having a first porosity; and
a shell component surrounding the core component and having a second porosity, the second porosity differing from the first porosity,
wherein the core component comprises a first polymer network formed from one or more monomers of Formula (A); one or more monomers of Formula (B1), (B2), or (B3); one or more monomers comprising an alkyne moiety; and one or more monomers comprising an azide moiety:

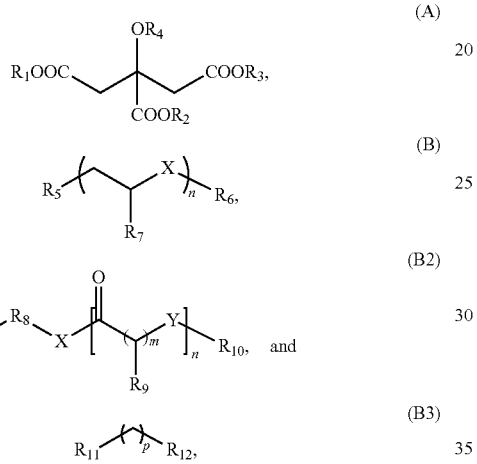

wherein
R$_1$, R$_2$, and R$_3$ are independently —H, —CH$_3$, —CH$_2$CH$_3$, or M$^+$;
R$_4$ is —H;
R$_5$ is —H, —OH, —OCH$_3$, —OCH$_2$CH$_3$, —CH$_3$, —CH$_2$CH$_3$, —NH$_2$, NHCH$_3$, —CH$_2$CH$_2$NHCH$_3$, —N(CH$_3$)$_2$, or —CH$_2$CH$_2$N(CH$_2$CH$_3$)$_2$;
R$_6$ is —H, —CH$_3$, or —CH$_2$CH$_3$,
R$_7$ is —H or —CH$_3$;
R$_8$ is —(CH$_2$)$_a$—, —(CH$_2$CH$_2$O)$_b$—, or —(CH$_2$OCH$_2$)$_b$—;
R$_9$ is —H, —CH$_3$, or a C2-C20 alkyl;
R$_{10}$ is —H, —C(O)CH$_3$, or —C(O)CH$_2$CH$_3$;
R$_{11}$ and R$_{12}$ are independently —OH or —NH$_2$;
M$^+$ is a monovalent cation;
X and Y are independently —O— or —NH—;
Z is —H, —CH$_3$, or

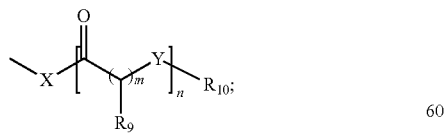

a is an integer from 0 to 20;
b is an integer from 0 to 2000;
n is an integer between 1 and 2000; and
m and p are independently integers ranging from 1 to 20; and wherein the monomer of Formula (B1) has at least one terminus comprising —OH or —NH2; and
wherein the shell component comprises a second polymer network formed from one or more monomers of Formula (A); one or more monomers of Formula (B1), (B2), or (B3); one or more monomers comprising an alkyne moiety; and one or more monomers comprising an azide moiety; and
wherein, in the alternative, either:
(a) the one or more monomers comprising one or more azide moieties comprises a monomer of Formula (G1) or (G2):

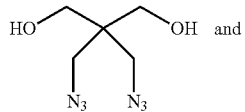

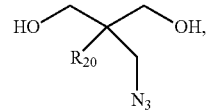

wherein
R$_{20}$ is —CH$_3$ or —CH$_2$CH$_3$, or
(b) the one or more monomers comprising one or more alkyne moieties comprises a monomer of Formula (H1), (H2), (H3), (H4), (H5), or (H6):

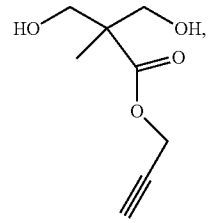

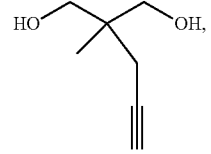

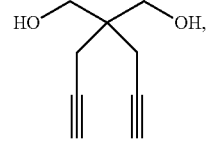

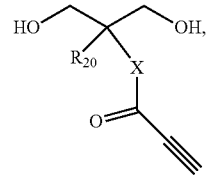

-continued

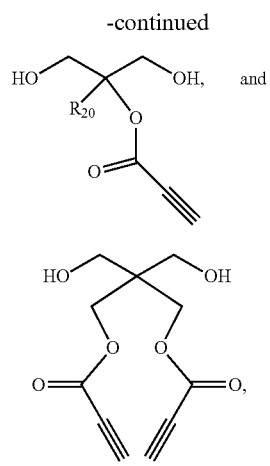

wherein
R$_{20}$ is —CH$_3$ or —CH$_2$CH$_3$; and
X is —NH—.

16. The scaffold of claim 15, wherein the core component exhibits a higher porosity than the shell component.

17. The scaffold of claim 15, wherein the first porosity is between about 30% and about 99% and the second porosity is between about 0% and about 99%.

18. The scaffold of claim 15, wherein a particulate inorganic material is dispersed within the first polymer network and/or the second polymer network.

19. The scaffold of claim 18, wherein the particulate inorganic material comprises hydroxyapatite.

20. The scaffold of claim 18, wherein the particulate inorganic material is present in the first polymer network or the second polymer network in an amount up to about 70 weight percent, based on the total weight of the first polymer network or the second polymer network, respectively.

21. The scaffold of claim 15, wherein the first polymer network and the second polymer network exhibit an average pore size of about 800 nm to about 1000 μm.

22. The scaffold of claim 15, wherein the core component and the shell component are concentric cylinders.

23. The scaffold of claim 15, wherein the diameter of the core component is about 1 percent to about 90 percent of the diameter of the shell component.

24. The scaffold of claim 15, wherein the first polymer network and/or the second polymer network comprises the reaction product of an amine, an amide, or an isocyanate with the one or more monomers of Formula (A), one or more monomers of Formula (B1), (B2), or (B3), one or more monomers comprising one or more alkyne moieties, and one or more monomers comprising one or more azide moieties.

25. The scaffold of claim 15, wherein the first polymer network and/or the second polymer network comprises the reaction product of a polycarboxylic acid or a functional equivalent of a polycarboxylic acid with the one or more monomers of Formula (A), one or more monomers of Formula (B1), (B2), or (B3), one or more monomers comprising an alkyne moiety, and one or more monomers comprising an azide moiety.

26. The scaffold of claim 15, wherein the first polymer network and/or the second polymer network comprises the reaction product of an amino acid with the one or more monomers of Formula (A), one or more monomers of Formula (B1), (B2), or (B3), one or more monomers comprising an alkyne moiety, and one or more monomers comprising an azide moiety.

27. The scaffold of claim 15, wherein the scaffold exhibits one or more of a compressive peak stress between about 1 MPa and about 45 MPa, an initial modulus between about 50 MPa and about 1500 MPa, and a peak compressive strain at break between about 2% and about 5%.

28. The composition of claim 8, wherein the amino acid is selected from the group consisting of alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan and valine.

29. The composition of claim 8, wherein R$_{14}$ is an alpha-amino acid side chain.

30. The composition of claim 7, wherein the polymer is formed from one or more monomers of Formula (A); one or more monomers of Formula (B1), (B2), or (B3); one or more monomers comprising one or more alkyne moieties and/or one or more azide moieties; and one or more monomers of Formula (D2):

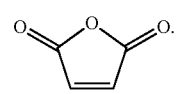 (D2)

31. The composition of claim 1, wherein the polymer is a reaction product of (i) citric acid, a citrate, or an ester of citric acid with (ii) a polyol, (iii) one or more alkynes and/or azides, and (iv) a catechol-containing species.

32. The composition of claim 31, wherein the catechol-containing species comprises L-3,4-dihydroxyphenylalanine (L-DOPA) of D-3,4-dihydroxyphenylalanine (D-DOPA).

* * * * *